(12) United States Patent
Antonia

(10) Patent No.: US 10,995,140 B2
(45) Date of Patent: May 4, 2021

(54) GM-CSF/CD40L VACCINE AND CHECKPOINT INHIBITOR COMBINATION THERAPY

(71) Applicant: H. LEE MOFFITT CANCER CENTER AND RESEARCH INSTITUTE, INC., Tampa, FL (US)

(72) Inventor: Scott Antonia, Land O'Lakes, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 72 days.

(21) Appl. No.: 15/579,311

(22) PCT Filed: Jun. 3, 2016

(86) PCT No.: PCT/US2016/035922
§ 371 (c)(1),
(2) Date: Dec. 4, 2017

(87) PCT Pub. No.: WO2016/197067
PCT Pub. Date: Dec. 8, 2016

(65) Prior Publication Data
US 2018/0162943 A1    Jun. 14, 2018

Related U.S. Application Data

(60) Provisional application No. 62/171,829, filed on Jun. 5, 2015.

(51) Int. Cl.
| | | |
|---|---|---|
| C07K 16/28 | (2006.01) | |
| A61K 39/00 | (2006.01) | |
| A61K 39/395 | (2006.01) | |
| A61P 31/00 | (2006.01) | |
| A61P 11/00 | (2006.01) | |
| A61P 35/00 | (2006.01) | |
| A61K 45/00 | (2006.01) | |

(52) U.S. Cl.
CPC ...... *C07K 16/2818* (2013.01); *A61K 39/0011* (2013.01); *A61K 39/001139* (2018.08); *A61K 39/39541* (2013.01); *A61K 39/39558* (2013.01); *A61K 45/05* (2013.01); *A61P 11/00* (2018.01); *A61P 31/00* (2018.01); *A61P 35/00* (2018.01); *A61K 2039/505* (2013.01); *A61K 2039/5152* (2013.01); *A61K 2039/5156* (2013.01); *A61K 2039/545* (2013.01); *A61K 2039/572* (2013.01); *A61K 2300/00* (2013.01); *C07K 2317/76* (2013.01)

(58) Field of Classification Search
CPC ............ C07K 16/2896; C07K 2317/76; A61K 2039/505; A61K 2309/5152; A61K 2309/5156

USPC ............................................. 424/133.1, 178.1
See application file for complete search history.

(56) References Cited

U.S. PATENT DOCUMENTS

| | | |
|---|---|---|
| 5,192,537 A | 3/1993 | Osband |
| 6,960,648 B2 | 11/2005 | Bonny |
| 8,008,449 B2 | 8/2011 | Korman et al. |
| 8,552,154 B2 | 10/2013 | Freeman et al. |
| 8,617,546 B2 | 12/2013 | Kang et al. |
| 2002/0035243 A1 | 3/2002 | Imfeld et al. |
| 2002/0120100 A1 | 8/2002 | Bonny |
| 2003/0032594 A1 | 2/2003 | Bonny |
| 2011/0059137 A1* | 3/2011 | Antonia ............ A61K 39/0011 424/277.1 |
| 2013/0251752 A1* | 9/2013 | Antonia ............ A61K 39/0011 424/277.1 |
| 2013/0309250 A1 | 11/2013 | Cogswell et al. |
| 2015/0125463 A1 | 5/2015 | Cogswell et al. |
| 2020/0102538 A1* | 4/2020 | Borriello .............. C07K 16/18 |

OTHER PUBLICATIONS

Clinicaltrials.gov ("Study of Nivolumab in Combination With GM.CD40L Vaccine in Adenocarcinoma of the Lung"; Identifier: NCT02466568; pp. 1-7 (Nov. 18, 2019))*
Dessureault et al. (Annals of Surgical Oncology 14(2):869-884 (Nov. 14, 2006)).*
Gray et al. (Cancer Immunology, Immunotherapy 67:1853-1862 (Sep. 12, 2018)).*
Clinicaltrials.gov (NCT02466568, pp. 1-7, posted Jun. 9, 2015).*
International Search Report for international application No. PCT/US2016/035922, dated Sep. 19, 2016 (2 pages).
Laura QM Chow, "Exploring Novel Immune-Related Toxicities and Endpoints with Immune-Checkpoint Inhibitors in Non-Small Cell Lung Cancer," 2013 ASCO Educational Book, p. e280-e286.

(Continued)

*Primary Examiner* — Lynn A Bristol
(74) *Attorney, Agent, or Firm* — Meunier Carlin & Curfman LLC

(57) ABSTRACT

A method is disclosed for treating a cancer in a subject. The method comprises administering to the subject a composition comprising a therapeutically effective amount of a checkpoint inhibitor and a therapeutically effective amount of a tumor vaccine. In some embodiments, the tumor vaccine comprises radiated autologous tumor cells and a cell line engineered to express GM-CSF and CD40 ligand. In some embodiments, the checkpoint inhibitor comprises an anti-PD-1 antibody (e.g., BMS 936558), anti-PD-L1 antibody (e.g., cloneM1H1), anti-CTLA-4 antibody (e.g., Ipilimumab, BMS), or any combination thereof.

4 Claims, 11 Drawing Sheets

(56) References Cited

OTHER PUBLICATIONS

J. Duraiswamy et al., "Dual Blockade of PD-1 and CTLA-4 Combined with Tumor Vaccine Effectively Restores T-Cell Rejection Function in Tumors," Cancer Res, (2013) vol. 73, No. 12, p. 3591-3603.
J. Kleponis et al., "Fueling the engine and releasing the break: combinational therapy of cancer vaccines and immune checkpoint inhibitors," Cancer Biol Med, (2015) vol. 12, p. 201-208.
M. A. Postow et al., "Immune Checkpoint Blockade in Cancer Therapy," Journal of Clinical Oncology, (2015) vol. 33, 10 pages.

\* cited by examiner

GM-CSF/CD40L VACCINE AND CHECKPOINT INHIBITOR COMBINATION THERAPY

CROSS-REFERENCE TO RELATED APPLICATIONS

This application claims the benefit of U.S. Provisional Application No. 62/171,829, filed Jun. 5, 2015, which is hereby incorporated herein by reference in its entirety.

BACKGROUND

It has been shown that cancers have multiple mechanisms of preventing the activation of and evading an immune response. Therefore, a single manipulation such as immunization with a vaccine will not likely be adequate for clinical efficacy.

SUMMARY

A method is disclosed for treating a cancer in a subject. The method comprises administering to the subject a composition comprising a therapeutically effective amount of a checkpoint inhibitor and a therapeutically effective amount of a tumor vaccine. In some embodiments, the tumor vaccine comprises radiated autologous tumor cells and a cell line engineered to express GM-CSF and CD40 ligand.

In some cases, the vaccine comprises a mixture of one, two, or more human lung adenocarcinoma cell lines and a bystander cell line engineered to secrete GM-CSF and express CD40 ligand (GM.CD40L). GM-CSF secretion at the vaccine site is expected to recruit and differentiate dendritic cells (DCs), which will be activated by their encounter with CD40 ligand on the surface of the bystander cells. These activated and antigen-loaded DCs will then migrate to the draining lymph nodes and activate tumor antigen-specific T cells (CD4 and CD8). These activated T cells will then recirculate to metastatic sites and kill tumor cells.

The cell line can be further engineered to express one more factors selected from the group consisting of IL-1, IL-2, IL-3, IL-4, IL-5, IL-6, IL-7, IL-8, IL-9, IL-10, IL-11, IL-15, erythropoietin, GCSF, M-CSF, platelet derived growth factor (PDGF), MSF, FLT-3 ligand, EGF, fibroblast growth factor (FGF), bFGF (FGF-2), FGF-3, FGF-4, FGF-5, FGF-6, FGF-7, insulin-like growth factor1 (IGF-1), insulin-like growth factor 2 (IGF-2); vascular endothelial growth factor (VEGF), IFN-gamma, IFN-alpha, IFN-beta, leukemia inhibitory factor (LIF), ciliary neurotrophic factor (CNTF), oncostatin M, stem cell factor (SCF), TGF-α, and TGF-µ1. The cell line is preferably MHC negative, and can be a tumor cell line.

The combination of the disclosed vaccine with an immune checkpoint can amplify the T-cell response and enhance the efficacy of tumor infiltrating T cells, thus resulting in a more potent antitumor effect compared to a single agent. In some embodiments, the checkpoint inhibitor comprises an anti-PD-1 antibody (e.g., BMS 936558), anti-PD-L1 antibody (e.g., cloneM1H1), anti-CTLA-4 antibody (e.g., Ipilimumab, BMS), or any combination thereof.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
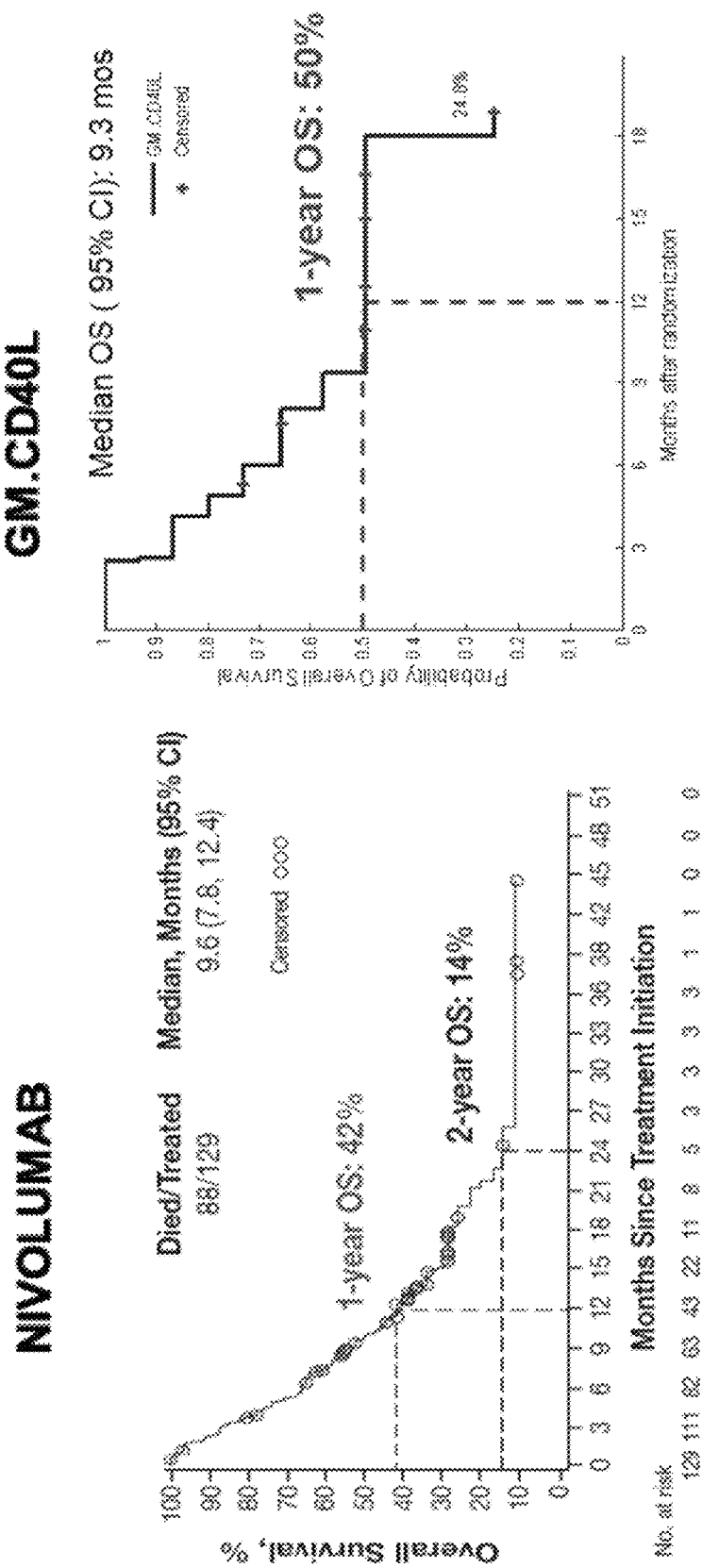
FIG. 1 shows OS curves of single-agent Nivolumab vs. GM.CD40L vaccine in a pretreated population of advanced/metastatic NSCLC and lung adenocarcinoma, respectively.

Tumor vaccines in general have very little single agent activity because even if they are effective in expanding tumor-specific T cells in the lymphoid compartment, these T cells are rendered inactive in the tumor microenvironment due to exposure to PD-L. Therefore it is necessary to combine tumor vaccines with agents that are directed at the tumor microenvironment.

In order to actively drive an antitumor immune response, therapeutic cancer vaccines have been developed. Unlike the prophylactic vaccines that are used preventatively to treat infectious diseases, therapeutic vaccines are designed to treat established cancer by stimulating an immune response against a specific tumor-associated antigen. A number of tumor-associated antigens are known in the art, and methods for detecting them are well known.

In some embodiments the tumor vaccine comprises "gene-modified universal producer cells" that are a source of expressed GM-CSF and CD40 ligand. In some embodiments, the cell line is MHC molecule negative cell line, such as the K562 cell line (available from the American Type Culture Collection, Manassas, Va.)—the use of such cells should reduce the incidence of allogeneic responses to the cells upon introduction into individuals. In some cases, transformed cells express exogenous GM-CSF and CD40 ligand transgenes.

In some embodiments, the "gene-modified universal producer cells" can also contain and express transgenes encoding one or more compounds selected from the group consisting of IL-1, IL-2, IL-3, IL-4, IL-5, IL-6, IL-7, IL-8, IL-9, IL-10, IL-11, IL-15, erythropoietin, G-CSF, M-CSF, platelet derived growth factor (PDGF), MSF, FLT-3 ligand, EGF, fibroblast growth factor (FGF; e.g., aFGF (FGF-1), bFGF (FGF-2), FGF-3, FGF-4, FGF-5, FGF-6, or FGF-7), insulin-like growth factors (e.g., IGF-1, IGF-2); vascular endothelial growth factor (VEGF); interferons (e.g., IFN-gamma, IFN-alpha, IFN-beta); leukemia inhibitory factor (LIF); ciliary neurotrophic factor (CNTF); oncostatin M; stem cell factor (SCF); transforming growth factors (e.g., TGF-a, TGF-~1, TGF-~1, TGF-~1). DNA molecules can encode mammalian, including human or murine, versions of the aforementioned compounds.

In some embodiments, peripheral blood lymphocytes of a individual afflicted with a tumor, cancer, or malignancy are cultured with the antigen presenting cells (e.g., dendritic cells), GM-CSF/CD40L expressing cells (or cells derived from a GM-CSF/CD40L cell line), and optionally apoptotic autologous tumor, cancer, or malignant cells (or antigens derived therefrom). The cultured cells are then re-administered to the patient as a form of autologous therapy (see, for example, U.S. Pat. No. 5,192,537 [hereby incorporated by reference in its entirety]). The methodology is also applicable to patients experiencing a recurrence of a tumor, cancer, or malignancy. In a further embodiment, suppressor T-cells are removed from the individual's peripheral blood lymphocytes and the remaining cells are suspended in a tissue culture medium containing GM-CSF/CD40L expressing cells and irradiated autologous tumor or cancer cells (or the antigens derived therefrom). The cells then are incubated, at temperatures of about 37° C. to about 40° C., for a period of time so that they are activated. Those cells specific for the tumor antigen are clonally expanded and, optionally, treated to re-deplete various kinds of suppressor cells and/or boost their activity.

Activated cells may be co-administered with cells expressing GM-CSF/CD40L and/or with one or more cytokines.

In some cases, the tumor vaccine comprises (1) radiated tumor cells (e.g., autologous tumor cells) providing the source of shared tumor antigens and (2) a bystander cell line (GM.CD40L) engineered to secrete GM-CSF and express CD40 ligand on its surface. GM-CSF secretion at the vaccine site can recruit and differentiate DCs, which will be activated by their encounter with CD40 ligand on the surface of the bystander cells. Apoptotic bodies from the radiated tumor cells will then be processed by the DCs.

Tumor vaccines can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. A list of immune-checkpoint targeting antibodies in clinical trials is provided in Table 2.

TABLE 2

Clinically evaluated immune-checkpoint blocking antibodies

| Target | Antibody |
| --- | --- |
| CTLA-4 | Ipilimumab (MDX-010) |
|  | Tremelimumab (CP-675,206) |
| PD1 | Nivolumab (BMS-936558 or MDX1106) |
|  | CT-011 |
|  | MK-3475 |

TABLE 2-continued

Clinically evaluated immune-checkpoint blocking antibodies

| Target | Antibody |
| --- | --- |
| PDL1 | MDX-1105 (BMS-936559) |
|  | MPDL3280A |
|  | MSB0010718C |
| PDL2 | rHIgM12B7 |
| B7-H3 | MGA271 |
| LAG3 | BMS-986016 |

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MEDI4736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed compositions and methods can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

Numerous anti-cancer drugs are available for combination with the present method and compositions. The following is a non-exhaustive lists of anti-cancer (anti-neoplastic) drugs that can be used in conjunction with irradiation: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil 1131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

The cancer of the disclosed methods can be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer (NSCLC), neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer. For example, Table 3 provides a list of the categories and types of cancers.

TABLE 3

| Cancer Cases |
|---|
| Oral cavity & pharynx |
| Tongue |
| Mouth |
| Pharynx |
| Other oral cavity |
| Digestive system |
| Esophagus |
| Stomach |
| Small intestine |
| Colon |
| Rectum |
| Anus, anal canal, & anorectum |
| Liver & intrahepatic bile duct |
| Gallbladder & other biliary |
| Pancreas |
| Other digestive organs |
| Respiratory system |
| Larynx |
| Lung & bronchus |
| Other respiratory organs |
| Bones & joints |
| Soft tissue (including heart) |
| Skin (excluding basal & squamous) |
| Melanoma-skin |
| Other nonepithelial skin |
| Breast |
| Genital system |
| Uterine cervix |
| Uterine corpus |
| Ovary |
| Vulva |
| Vagina |
| Prostate |
| Testis |
| Penis |
| Urinary system |
| Urinary bladder |
| Kidney & renal pelvis |
| Ureter & other urinary organs |

TABLE 3-continued

Cancer Cases

Eye & orbit
Brain & other nervous system
Endocrine system

Thyroid
Other endocrine
Lymphoma

Hodgkin lymphoma
Non-Hodgkin lymphoma
Myeloma
Leukemia

Acute lymphocytic leukemia
Chronic lymphocytic leukemia
Acute myeloid leukemia
Chronic myeloid leukemia
Other leukemia‡
Other & unspecified primary sites Compositions, Formulations and Methods of Administration In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, or hydrates thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

In one embodiment, the disclosed compositions are administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of compositions are administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

Although the compositions may be administered once or several times a day, and the duration of the treatment may be once per day for a period of about 1, 2, 3, 4, 5, 6, 7 days or more, it is more preferably to administer either a single dose in the form of an individual dosage unit or several smaller dosage units or by multiple administration of subdivided dosages at certain intervals. For instance, a dosage unit can be administered from about 0 hours to about 1 hr, about 1 hr to about 24 hr, about 1 to about 72 hours, about 1 to about 120 hours, or about 24 hours to at least about 120 hours. Alternatively, the dosage unit can be administered from about 0.5, 1, 2, 3, 4, 5, 6, 7, 8, 9, 10, 11, 12, 13, 14, 15, 16, 17, 18, 19, 20, 21, 22, 23, 24, 30, 40, 48, 72, 96, 120 hours. Subsequent dosage units can be administered any time following the initial administration such that a therapeutic effect is achieved. Therapy with the disclosed compositions can instead include a multi-level dosing regimen wherein the composition is administered during two or more time periods, preferably having a combined duration of about 12 hours to about 7 days, including, 1, 2, 3, 4, or 5 days or about 15, 15, 30, 35, 40, 45, 50, 55, 60, 65, 70, 75, 80, 85, 90, 95, 100, 105, 110, 115, 120, 125, 130, 135, 140, or 144 hours or about 1 to 24 hours, about 12 to 36 hours, about 24 to 48 hours, about 36 to 60 hours, about 48 to 72 hours, about 60 to 96 hours, about 72 to 108 hours, about 96 to 120 hours, or about 108 to 136 hours. In one embodiment, the two-level dosing regimen has a combined duration of about 1 day to about 5 days; in other embodiments, the two-level dosing regimen has a combined duration of about 1 day to about 3 days.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Definitions

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder.

In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "hyperplastic cell" or "hyperplasm" refers to a cell undergoing physiological (normal) cell proliferation ("hyperplasia").

The term "neoplastic cell" or "neoplasm" refers to a cell undergoing abnormal cell proliferation ("neoplasia"). The growth of neoplastic cells exceeds and is not coordinated with that of the normal tissues around it. The growth typically persists in the same excessive manner even after cessation of the stimuli, and typically causes formation of a tumor. Neoplasms may be benign, premalignant, or malignant.

The term "cancer" or "malignant neoplasm" refers to a cell that displays uncontrolled growth, invasion upon adjacent tissues, and often metastasis to other locations of the body.

The term "tumor" refers to an abnormal mass of tissue containing neoplastic cells.

The term "metastasis" refers to the spread of malignant tumor cells from one organ or part to another non-adjacent organ or part. Cancer cells can "break away," "leak," or "spill" from a primary tumor, enter lymphatic and blood vessels, circulate through the bloodstream, and settle down to grow within normal tissues elsewhere in the body. When tumor cells metastasize, the new tumor is called a secondary or metastatic cancer or tumor.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

The terms "peptide," "protein," and "polypeptide" are used interchangeably to refer to a natural or synthetic molecule comprising two or more amino acids linked by the carboxyl group of one amino acid to the alpha amino group of another.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The term "tumor infiltrating lymphocyte" or "TIL" refers to white blood cells that have left the bloodstream and migrated into a tumor.

The term "regression" does not necessarily imply 100% or complete regression. Rather, there are varying degrees of regression of which one of ordinary skill in the art recognizes as having a potential benefit or therapeutic effect. The term also encompasses delaying the onset of the disease, or a symptom or condition thereof.

A number of embodiments of the invention have been described. Nevertheless, it will be understood that various modifications may be made without departing from the spirit and scope of the invention. Accordingly, other embodiments are within the scope of the following claims.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

EXAMPLES

Example 1: A Randomized Phase I/II Study of Nivolumab in Combination with GM.CD40L Vaccine in Adenocarcinoma of the Lung The following is a description of phase II trial to establish the efficacy of combining anti-PD-1 therapy with a GM.CD40L tumor vaccine.
Study Synopsis
Background and Rationale It has been shown that cancers have multiple mechanisms of preventing the activation of and evading an immune response. Therefore, a single manipulation such as immunization with a vaccine will not likely be adequate for clinical efficacy. Lung adenocarcinoma is an incurable disease with current therapy producing a survival benefit, although small. Recently, it was demonstrated that anti-PD-1 has significant clinical activity in this disease with an ORR of 26%. While this is remarkable, 74% of patients did not respond. Therefore, going forward it will be important to develop combination therapy to improve the efficacy. A potential class of agents that could be used in combination with anti-PD-1 is the therapeutic tumor vaccines. Because it is likely that combination immunotherapy will need to be developed to produce significant efficacy, we thus propose to perform a randomized study in which the combination is evaluated.

Therapeutic tumor vaccines have not been able to produce significant numbers of tumor regressions in clinical trials, likely in large part due to tumor-associated PD-L1 mediated inhibition of the vaccine-induced effector T cells when they enter the tumor microenvironment.

Anti-PD-1 has significant single-agent activity in lung cancer due to its ability to prevent T cell inhibition, and it is likely that expanding tumor-specific T cells with a tumor vaccine will increase the frequency of clinical responses.[1,2] There have been no tumor vaccines tested in combination with anti-PD-1 in lung cancer patients.

We will conduct a phase II trial to establish the efficacy of the combination and to follow patients for safety. The primary objective will be to determine the standard objective tumor response rates as a measure of efficacy. However, immunotherapeutic strategies can also result in the stabilization of disease; thus, to determine whether disease stabilization is relevant, Progression-free survival, overall survival, and duration of response will also be important secondary clinical endpoints for the study.
Objectives
Phase I—Primary Objective:

Determine the safety, tolerability, and MTD of nivolumab in combination with GM.CD40L vaccine in patients with advanced/metastatic adenocarcinoma of the lung.
Phase II—Primary Objective Determine in a randomized phase II trial the objective tumor response rate to nivolumab alone (Arm A) and nivolumab in combination with a GM.CD40L vaccine (Arm B) in patients with metastatic lung adenocarcinoma
Secondary Objectives Determine the overall survival and progression-free survival of patients treated with nivolumab alone (Arm A) and nivolumab in combination with a GM.CD40L vaccine (Arm B).
Study Design Patients enrolled will be treated with 1 of 2 potential regimens: Phase I and Phase II treatment arm=Patients will receive continuous nivolumab 3 mg/kg IV every 2 weeks with the GM.CD40L given every 2 weeks×4, then every month×4, and then as boosters every 3 months until evidence of progressive disease, patient withdrawal from the study or the treatment, or intolerable toxicity. Phase II control arm=Patients randomized to the nivolumab alone will be treated with nivolumab every 2 weeks until evidence of progressive disease, patient withdrawal from the study or the treatment, or intolerable toxicity.

We will start with the dose planned for the phase II trial with a provision for dose de-escalation in the event of dose-limiting toxicities (DLTs). The 6 patients who we expect to enroll in the phase I part will be observed through a 21-day DLT period before initiating enrollment in the phase II trial. During the phase I portion, a maximum of 2 patients will be enrolled per week.

If there is no more than 1 DLT within a 21-day period, then the phase II portion of the trial will initiate. No dose escalation is planned beyond dose level 1. The recommended Phase II dose will be defined as the highest dose level of GM.CD40L vaccine in combination with nivolumab that induced DLT in fewer than 33% of patients (i.e., one dose level below that which induced DLT in at least two of six patients).

Phase I. Both of the investigational agents that will be used in the phase II trial (GM.CD40L vaccine and nivolumab) have been tested individually as single agents in phase I clinical trials. The combination of the vaccine with anti-PD-1 has not yet been tested; therefore, we will first conduct a phase I trial of this combination. We will start with the dose planned for the phase II trial with a provision for dose de-escalation in the event of dose-limiting toxicities (DLTs). The 6 patients who we expect to enroll in the phase I part will be observed through a 21-day DLT period before initiating enrollment in the phase II trial. During the phase I portion a maximum of 2 patients will be enrolled per week.

If there is no more than 1 DLT within a 21-day period, then the phase II portion of the trial will initiate. No dose escalation is planned beyond dose level 1. If 2 or more patients experience grade 3 hematologic or grade 3 nonhematologic toxicity (DLT is further defined in Section 6.1) in dose level 1, then dose de-escalation will occur. Dose level −1 will follow the same rules.

The recommended Phase II dose will be defined as the highest dose level of GMCD40L vaccine in combination with nivolumab that induced DLT in fewer than 33% of patients (i.e., one dose level below that which induced DLT in at least two of six patients).

Figure 2:
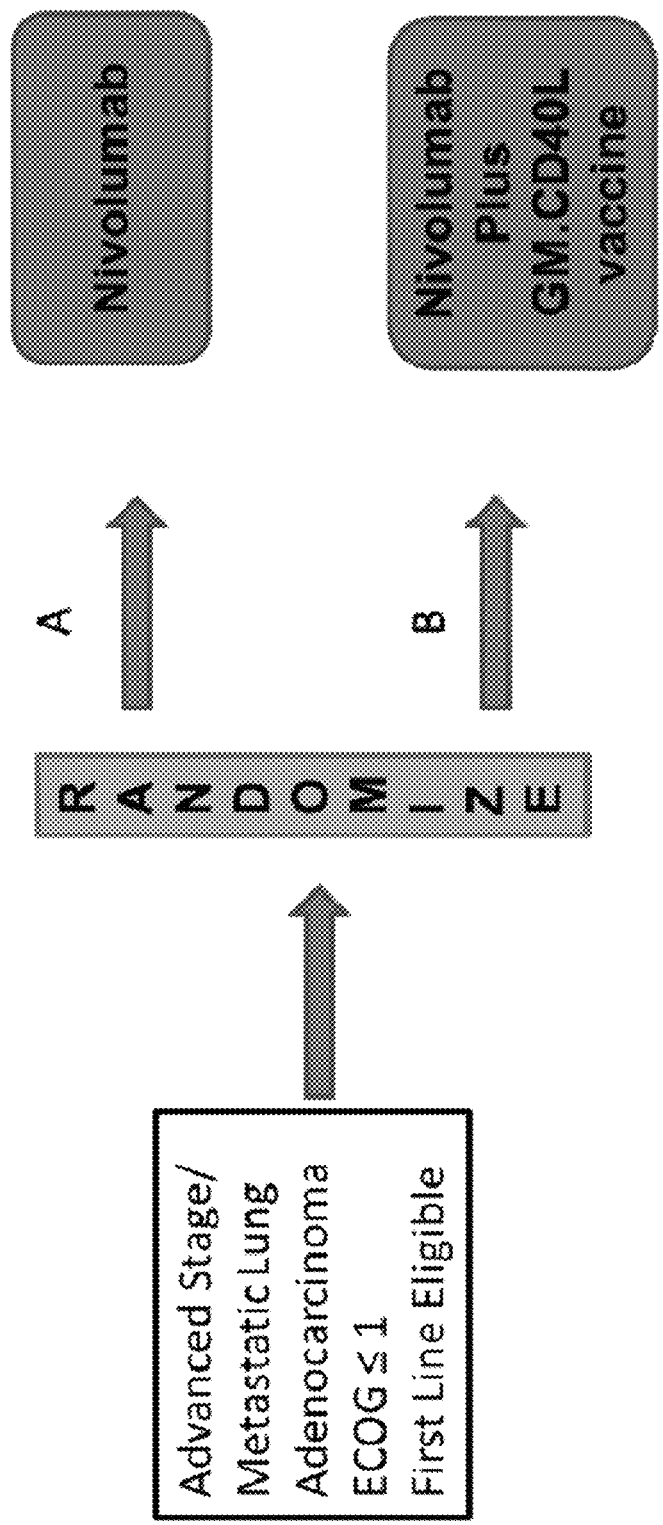
FIG. 2 shows a trial schema.

Randomized phase II trial. The randomized phase II trial will be for first-line advanced-stage/metastatic lung adenocarcinoma patients. As diagrammed in FIG. 2, there will be 2 arms that will differ with respect to the immunotherapy part: patients in Arm A will receive anti-PD-1, and patients in Arm B will receive anti-PD-1 plus vaccines.

Key Inclusion Criteria
1) Histologic or cytologic diagnosis of advanced/metastatic adenocarcinoma of the lung
2) ECOG performance status of 0/1
3) Age greater than 18 years
4) Chemotherapy naïve or have completed adjuvant chemotherapy for NSCLC >6 months prior
5) Adequate bone marrow, renal and hepatic function
6) Patients must have measurable metastatic disease according to RECIST v1.1 criteria
7) Mandatory archival tissue or willingness to undergo a fresh biopsy
8) Life expectancy of greater than 6 months Key Exclusion Criteria
1) Symptomatic brain metastasis or uncontrolled CNS metastasis
2) Pregnancy or breast feeding
3) Serious uncontrolled medical disorder or active infection that would impair the patient's ability to receive study treatment
4) Prior use of a PD1 or PDL1 inhibitor
5) Concurrent use of other anticancer approved or investigational agents is not allowed
6) Autoimmune disorders
7) Prior malignancy in past 2 years
8) Systemic steroids at doses greater than 10 mg/day of prednisone or the equivalent
9) Any other pre-existing immunodeficiency condition (including known HIV infection)

Statistical Plan and Analysis

We expect to enroll a total of 100 patients in order to have 96 enrolled patients to be randomized over a 2-year time period. A Bayesian posterior probability into the two parallel Simon two-stage designs will be used to allow comparing the two treatment arms. Power analysis (the operating characteristics of this design) is also performed by simulations. In summary, this design gives an 84% overall power to claim arm B as the winner when the true probabilities of response with arms A and B are 26% and 46%, respectively. The type I error is controlled at 5% (when both arms have a 26% response rate).

Correlative Biomarkers

Biomarker analyses for PDL1 status will be captured on the patients enrolled and correlated with clinical outcomes. All results will be descriptive in nature.

1 Objectives
1.1. Phase I—Primary Objective
Determine the safety, tolerability, and MTD of nivolumab in combination with GM.CD40L vaccine in patients with advanced/metastatic adenocarcinoma of the lung.
1.2. Phase II—Primary Objective
Determine in a randomized phase II trial the objective tumor response rate to nivolumab alone (Arm A) and nivolumab in combination with a GM.CD40L vaccine (Arm B) in patients with metastatic lung adenocarcinoma
1.3. Secondary Objectives
Determine the overall survival and progression-free survival of patients treated with nivolumab alone (Arm A) and nivolumab in combination with a GM.CD40L vaccine (Arm B).

2 Background
2.1. Study Disease
2.1.1. Lung Adenocarcinoma

Metastatic adenocarcinoma of the lung remains an incurable disease. Standard therapy is carboplatin with either pemetrexed or paclitaxel in combination with bevacizumab, followed by maintenance bevacizumab or pemetrexed. This produces a survival benefit; however, median survival is only 12.3 months[3]. We propose as our primary objective a proof-of-concept trial testing a novel immunotherapy combination: anti-PD1 plus a GM.CD40L vaccine.

2.1.2 Anti-PD-1 has Significant Anti-Tumor Activity in Lung Adenocarcinoma

PD-1 is a T-cell surface receptor that delivers a negative signal to T cells when it engages its ligand PD-L1 expressed on antigen presenting cells and T reg. This is a feedback mechanism whereby immune responses are dampened when no longer needed. This mechanism of control of T cells can be co-opted by tumors to escape rejection by the immune system. Tumor cells can aberrantly express PD-L1, and so tumor antigen-specific T cells activated in tumor draining lymph nodes or by tumor vaccines are shut down when they enter into the tumor microenvironment.

This discovery led to the development of a therapeutic strategy of monoclonal antibodies designed to prevent PD-1 binding to PD-L1. Bristol-Myers Squibb has in clinical development a genetically engineered, fully human IgG4 mAb specific for PD-1 (nivolumab) that we will use in the trial proposed here.[4] Of 129 non-small cell lung cancer patients treated with anti-PD-1 (1, 3, or 10 mg/kg), 22 (17%) had objective tumor responses. Non-squamous patients treated with 3 mg/kg (the dose we will use in the proposed trial) had an overall response rate of 26.3%. The Moffitt Cancer Center has treated over 60 patients with nivolumab and other anti-PD-L1 mAbs.

At the Chicago Multidisciplinary Symposium in Thoracic Oncology in October of 2014, Rizvi et al presented the updated data on first-line nivolumab monotherapy (3 mg/kg IV every 2 weeks.[5] This was based on a September 2014 datalock, which included 52 patients with either squamous cell or non-squamous cell lung cancer. 2/11 squamous cell (15%, [95% CI]) and 9/11 with non-squamous cell (23%, 95% CI, 11,39) patients demonstrated an objective response. 14 (27%) had SD, with 10 lasting ≥21 weeks, including 8 patients (21%) with non-squamous histology. PD was noted in 21/50 (40%) patients. The PFS rates at 24 weeks for the non-squamous and squamous patients were 40% (95% CI: 13.3, 87.3+) and 31% (95% CI: 9, 55), respectively. At the time of the presentation, the median duration of response and the median OS for the non-squamous histology had not been met. ORR was higher in the PD-L1-positive patients than the PD-L1-negative patients, 31% vs 10%. The median OS for the PD-L1-negative patients was 98 weeks, while the median OS for the PD-L1-positive patients was not reached.

Treatment-related AEs were reported in 33 of 52 patients (64%), with 8 (15%) patients who reported treatment-related grade 3/4 AEs. The treatment-related AEs reported in ≥5% of patients, regardless of grade, were fatigue (25%), rash (19%), diarrhea (10%), nausea (10%), pruritus (10%), hypothyroidism (6%), and pneumonitis (6%). Eight (15%) of the patients experienced grade 3-4 treatment-related AEs. Grade 3-4 rash was reported in 2 (4%) patients, and grade 3-4 pneumonitis was reported in 1 (2%) patient. Treatment-related AEs leading to discontinuation of study medication occurred in 5 (10%) patients. No drug-related deaths were reported at the time of this analysis.

2.1.3 Vaccines for NSCLC

Early trials testing immunotherapeutic strategies in lung cancer patients were negative and thus produced pessimism for this approach. However, over the past 2 years, several clinical trials have been conducted that showed that vaccines could produce anti-tumor immune responses in lung cancer patients. The vaccines included WT1 peptide[6], MAGE-3 protein[7], or UBE2V peptide[8] emulsified in immunologic adjuvants; lung tumor cell-[9] or CEA peptide-pulsed DCs[10]; and gene-modified autologous[11,12] or allogeneic tumor cells[13,14] The latter approach involved patients with measurable disease, and tumor regressions were observed. Raez et al treated 19 NSCLC patients (11 with adenocarcinoma) who were HLA A1 or A2 positive with an HLA A1 or A2-expressing allogeneic lung adenocarcinoma cell line that was transfected with the B7-1 gene. Five patients had stable disease and 1 developed a durable partial response[14]. Nemunaitis et al treated 33 advanced stage NSCLC patients with autologous tumor cells that were transfected with the GM-CSF gene. Three of these patients developed durable complete responses[11].

2.14 Tumor Cell Evasion of Mmune-Mediated Rejection

Tumor cells possess multiple means of evading T cell-mediated rejection. Rejection occurs despite the fact that there are tumor-associated antigens (TAAs) expressed by transformed cells but not by most normal cells[15] and despite the fact that T cells specific for TAAs are present within cancer patients 16-1. One mechanism whereby tumors escape immune-mediated destruction is by interfering with dendritic cells (DCs), which are potent antigen-presenting cells whose proper functioning is important in the induction of antigen-specific T cell responses[19]. Tumor-derived VEGF can interfere with the differentiation of DCs[20], as can IL-6 and MCS-F[21] Also, IL-10 is secreted by some tumors[22-24] and this cytokine has been shown to interfere with DC function[25-27]. Tumors are also capable of forcing DCs to undergo apoptosis 28-30

21.5 GM-CSF-Based Vaccines

In addition to the GM-CSF-based vaccine described above for NSCLC, a number of other GM-CSF-based vaccines, designed to enhance DC function at a tumor vaccine site, are currently being tested in clinical trials. With these vaccines autologous tumor cells[31-35], allogeneic tumor cell lines[36], or bystander cell lines[37] are transfected with the human GM-CSF gene. The GM-CSF-producing tumor cells, or bystander cells admixed with tumor cells, are injected into patients as the vaccine. The GM-CSF secreted at the vaccine site results in the recruitment and differentiation of DCs[38,39] and the tumor cells serve as the source of TAAs that are processed by the DCs, which subsequently migrate to lymph nodes where they activate TAA-specific T cells.

2.1.6 GM-CSF Secreting Bystander Cell Line-Based Vaccines

Levitsky and colleagues[37] have described the use of a vaccine in which a universal MHC-negative GM-CSF-producing "bystander cell" is mixed with irradiated tumor cells (antigen source). With the bystander vaccine approach, there is no need to genetically manipulate the autologous tumor cells. The parental cell line chosen for the "bystander cell line" was K562, a human erythroleukemia cell line, because it is MHC negative (potentially decreasing the magnitude of allogeneic responses that could shorten the duration of GM-CSF production on repeated immunization) and it can be grown in suspension cultures (facilitating large-scale production required for clinical testing). This autologous tumor cell/universal bystander cell vaccine, called K562 Bystander GVAX®, is being developed by the Johns Hopkins Cancer Center in collaboration with Cell Genesys, Inc., and is has currently completed clinical testing in phase I/II clinical trials in patients with multiple myeloma and AML. The study results are pending.

2.1.7 GM-CSF and CD40 Ligand-Transduced Tumor Cells Activate an Anti-Tumor Immune Response Chiodoni et al have extended the concept of using GM-CSF-based vaccines by transfecting the gene coding for CD40 ligand into tumor cells along with the GM-CSF gene in a murine model[40]. CD40 ligand is a potent activator of dendritic cells 4 that results in the upregulation of surface T cell costimulatory molecules and the increase in the secretion of cytokines[42,43] When both the GM-CSF and CD40 ligand genes were transfected into tumor cells, more mice transplanted with the tumor cells remained tumor free than mice transplanted with tumor cells that were transfected with the GM-CSF gene alone.

2.1.8 CD40 Ligand-Expressing Bystander Cell Line Based Vaccine

Brenner and colleagues tested a CD40 ligand based tumor vaccine in a murine model of multiple myeloma[44]. They used an approach similar to that of Levitsky and colleagues[45], utilizing a bystander cell strategy. They engineered a bystander cell line to express CD40 ligand and admixed these bystander cells with tumor cells as the source of tumor antigens. They found that this vaccine was very effective in protecting mice from a tumor challenge by recruiting and activating professional antigen-presenting cells at the vaccine site.

2.1.9 Tumor Antigens in Adenocarcinoma of the Lung

Several TAAs over-expressed in NSCLC lines have been identified. These include MAGE-1, 2, and 3, CEA, HER-2/neu, and WT-1[46,47]. Characterization of 31 NSCLC cell lines showed that the majority tested express HER-2/neu (90%) and CEA (58%) on the cell surface. Expression of other TAAs assayed was more sporadic[46]. In the clinical trial that is described in this proposal, we will be using two lung adenocarcinoma cell lines, NCI-H1944 and NCI-H2122, that together express HER-2/neu, CEA, GD-2, WT-1, and MAGE-1, -2, and -3[46].

2.2. Investigational Agents 2.2.1 Nivolumab (Anti-PD-1)

Nivolumab is a fully human, IgG4 (kappa) isotype mAb that binds PD-1[48]. Blockade of the PD-1 pathway by nivolumab was studied using the mixed lymphocyte reaction (MLR). PD-1 blockade resulted in a reproducible enhancement of both proliferation and IFN-7 release in the MLR. The effect of nivolumab on antigen-specific recall response was investigated using a CMV-restimulation assay with human PBMC, and was evaluated by ELISA. These data indicated that nivolumab, versus an isotype-matched control antibody, augmented IFN-γ secretion from CMV-specific memory T cells in a dose-dependent manner. PD-1 blockade by nivolumab has, therefore, been pursued as a promising avenue for immunotherapy of tumors.

The nivolumab dose levels and schedule were chosen for evaluation based on PK modeling, pre-clinical, and clinical data[48]. In CA209003, repeated dosing at 1, 3, and 10 mg/kg every 2 weeks (Q2wks) elicited clinical activity; however, there was no apparent relationship between dose and anti-tumor activity, AE frequency, or pharmacodynamic activity in this dose range. This study will utilize an every 2 week (Q2wk) schedule. Based on the long half-life (20-24 days), PK modeling suggests a Q2wk schedule will result in sustained exposure between treatments.

The starting dose of nivolumab was chosen as 3 mg/kg with de-escalation planned based upon DLTs. The safety data from CA209003 suggest that there may be very little difference in AE rates with nivolumab doses >1 mg/kg. As nivolumab is a fully human monoclonal antibody, it is metabolized by the reticuloendothelial system and not tissue-based CYP enzymes. As such, it is unlikely the combination of nivolumab and the vaccine will lead to direct drug-drug interactions.

Single-agent nivolumab has shown anti-tumor activity with a complete response (CR) or partial response (PR) in subjects with NSCLC, melanoma, and renal cell cancer (RCC).

The overall safety experience with nivolumab, as monotherapy or in combination with other therapeutics, is based on experience in approximately 1,500 subjects treated as of Jul. 21, 2013. For monotherapy, the safety profile is similar across tumor types. The one exception is pulmonary inflammation AEs, which may occur numerically more often in subjects with NSCLC, because in some cases it can be difficult to distinguish between nivolumab-related and unrelated causes of pulmonary symptoms and radiographic changes. There was no pattern in the incidence, severity, or causality of AEs to nivolumab dose level.

In several ongoing clinical studies, the safety of nivolumab in combination with other therapeutics such as ipilimumab, cytotoxic chemotherapy, anti-angiogenics and targeted therapies is being explored. Most studies are ongoing, and the safety profile of nivolumab combinations continues to evolve.

Overall, the safety profile of nivolumab was manageable and generally consistent across completed and ongoing trials with nivolumab monotherapy, with no maximum tolerated dose (MTD) reached at any dose tested up to 10 mg/kg.

Most AEs were low-grade (Grade 1 to Grade 2), with relatively few related high grade (Grade 3 to Grade 4) AEs including acute renal failure, fatigue, diarrhea, pneumonitis, and increased aspartate aminotransferase (AST)/alanine aminotransferase (ALT). Most high-grade events were manageable with use of corticosteroids or hormone replacement therapy (endocrinopathies) as instructed in management guidelines.

As of 18 Mar. 2013, 195 deaths had been reported in study MDX1106-03 during the course of the study or within 30 days of the last dose of study drug. The majority of the deaths were considered secondary to disease progression and malignant disease.

Three subjects died in study MDX1106-03 after developing pneumonitis. A 62-year-old male with NSCLC (adenocarcinoma) in the 1 mg/kg treatment group and a 59-year old male with CRC in the 10 mg/kg treatment group died with Grade 5 sepsis after having developed Grade 4 pneumonitis. Sepsis and pneumonitis were considered related to study drug by the investigator in both of these cases. In addition, a 40-year-old female with NSCLC (adenocarcinoma) in the 1 mg/kg treatment group died due to respiratory failure after having developed Grade 4 pneumonitis and tumor progression. Respiratory failure and penumonitis were considered by the investigator to be related to study drug.

Non-clinical safety findings of adverse pregnancy outcomes and infant losses in the absence of maternal toxicity have been reported. Findings in monkeys suggest a potential risk to human pregnancy if there is continued treatment with nivolumab during pregnancy.[49]

2.2.2 GM.CD40L Vaccine

The GM.CD40L vaccine consists of two components: (1) a mixture of two human lung adenocarcinoma cell lines providing the source of shared tumor antigens and (2) a bystander cell line engineered to secrete GM-CSF and express CD40 ligand on its surface. It is our hypothesis that GM-CSF secretion at the vaccine site will recruit and differentiate DCs, which will be activated by their encounter with CD40 ligand on the surface of the bystander cells. Apoptotic bodies from the radiated tumor cells will be processed by the DCs. Because it was recently demonstrated by Mellman's group that CD40 ligation results in the activation of cross-presentation of exogenous antigens taken up by DCs on MHC class I molecules,[50] we expect that the DCs at the vaccine sites will load shared tumor antigen-derived peptides onto both MHC class I and II molecules. These activated and antigen-loaded DCs will then migrate to the draining lymph nodes and activate tumor antigen-specific T cells (CD4 and CD8). These activated T cells will then recirculate to metastatic sites and kill tumor cells.

2.2.2.1 Clinical Experience with GM.CD40L Vaccine

Dr. Antonia's laboratory at Moffitt Cancer Center has constructed a GM-CSF- and CD40 ligand-expressing cell line and tested it in a pre-clinical model as well as in a phase I clinical trial. We recently completed enrollment to a phase I trial where cancer patients with stage IV disease were treated with a universal GM-CSF-producing and CD40L-expressing bystander cell line (GM.CD40L) and autologous tumor cells. 26 patients were enrolled, and we have treated 21 patients, with no adverse effects (other than mild local inflammation at the site of vaccine injection). (Four patients developed early progression and did not complete their sequence of injections. One patient withdrew consent.) Immunoassays and other correlative studies demonstrated tumor-specific T-cell responses, as well as recruitment and activation of dendritic cells, with evidence of stable disease in some patients, including one lasting up to 24 months.[51] Further, the Moffitt Cancer Center team has completed a Phase II study of an allogeneic GM.CD40L vaccine in combination with ATRA and cytoxan in advanced NSCLC (ATRA helps with DC maturation while cytoxan's role was to inhibit T-regulator cells). The trial enrolled 24 patients and was stopped early as it did not meet its primary endpoint of response rate. Only a few grade 3 events occurred and were limited to 3 subjects with headaches and one patient with diarrhea, nausea, and vomiting. In this heavily pretreated population of patients with NSCLC, we now have 2/24 patients enrolled who are long-term survivors. Upon further review of the data, the median overall survival of the patients was 9 months despite this being a heavily pretreated population. When compared with historical studies such as the Hanna et al study presented in JCO in 2004, our numbers are comparable if not better. On an intent-to-treat basis, the median survival time for pemetrexed was 8.3 months versus 7.9 for docetaxel (HR, 0.99; 95% CI, 0.82 to 1.2; noninferiority P: 0.226), which is similar to our median survival time of 9 months.[52] Furthermore, only one patient out of nearly 570 patients treated in both arms was alive at 20 months; however, in our phase II study, we have 2 out of 24 patients alive at 30+ months. Based on these finding, further evaluation of the vaccine regimen was warranted.[53] Through immune response analyses, we were able to detect good controls and a response in one patient. No substantial changes were detected in the MDSCs before versus after therapy. Based on these variable immune responses and the likely attribution of grade 3 adverse events to the ATRA and cytoxan and not the vaccine, to most optimize efficacy while minimizing toxicity, the plan was to move forward with the GM.CD40L vaccine without the combination of ATRA and cytoxan.

In our most recent phase II trial, which is ongoing, stage IV lung adenocarcinoma patients are randomized to GM.CD40L vaccine plus or minus CCL21 a chemokine. Both vaccine formulations are safe and had similar response rates (Gray et al, ASCO2014. Gray et al, IASLC WCLC 2014).

2.2.2.2 Nivolumab Vs GM.CD40L Vaccine: Similar 1- and 2-Year OS

Although we acknowledge that there exists limitations to performing cross-trial comparisons, we would like to highlight the similar 1-year and 2-year overall survival (OS) data between the 2 treatments as single agents (FIG. 1). Here, we demonstrate side-by-side OS curves from 1) the initial nivolumab trial involving patients with advanced-stage/metastatic, previously treated NSCLC[4] versus 2) interim analysis of our GM.CD40L vaccine in advanced-stage/metastatic previously treated lung adenocarcinoma patients (Gray et al, WCLC 2014). While the addition of CCL21 did not significantly impact the OS curve of the GM.CD40L, the 1-year OS data between GM.CD40L and nivolumab are similar.

2.3. Rationale for the Combination 2.3.1 the Anti-Tumor T-Cell Response Will be Amplified The GM.CD40L vaccine will amplify T cells directed at the tumor cells.

Anti-PD1 will enhance the T cell priming effect of the vaccine.

2.3.2 the Efficacy of Tumor Infiltrating T Cells Will be Enhanced

Anti-PD1 will reduce the inhibitory effect of PD-L1 on T cells in the tumor microenvironment.

2.4. Summary

It has been shown that cancers have multiple mechanisms of preventing the activation of and evading an immune response. Therefore, a single manipulation such as immunization with a vaccine will not likely be adequate for clinical efficacy. Lung adenocarcinoma is an incurable disease with current therapy producing a survival benefit, although small. Recently, it was demonstrated that anti-PD-1 has significant clinical activity in this disease with an ORR of 26%. While this is remarkable, 74% of patients did not respond. Therefore, going forward it will be important to develop combination therapy to improve the efficacy and to discover resistance mechanisms. A potential class of agents that could be used in combination with anti-PD-1 are the therapeutic tumor vaccines. Because it is likely that combination immunotherapy will need to be developed to produce significant efficacy, we thus propose to perform a randomized study in which the combination is evaluated.

Therapeutic tumor vaccines have not been able to produce significant numbers of tumor regressions in clinical trials, likely in large part due to tumor-associated PD-L1 mediated inhibition of the vaccine-induced effector T cells when they enter the tumor microenvironment. Anti-PD-1 has significant single-agent activity in lung cancer due to its ability to prevent T cell inhibition, and it is likely that expanding tumor-specific T cells with a tumor vaccine will increase the frequency of clinical responses.[1,2] There have been no tumor vaccines tested in combination with anti-PD-1 in lung cancer patients.

We will conduct a phase I/II trial to establish the efficacy of the combination and to follow patients for safety. The primary objective will be to determine the standard objective tumor response rates as a measure of efficacy. However, immunotherapeutic strategies can also result in the stabilization of disease; thus, to determine whether disease stabilization is relevant, time to progression will also be an important secondary clinical endpoint for the study.

3 Patient Selection 3.1. Eligibility Criteria

All inclusion and exclusion criteria will be assessed within 30 days before initiation of therapy.

All eligibility criteria must be met prior to enrolling a subject. The study will be conducted in accordance with Good Clinical Practice (GCP), as defined by the International Conference on Harmonisation (ICH), WHO and any local directives and in compliance with the protocol. This clinical protocol, any amendments, and the subject informed consent will require IRB, IBC, OBA, and FDA IND approval/favorable opinion before initiation of the study. Informed consent will be obtained from each patient enrolled onto the study.

3.1.1 Patients must have histologic or cytologic diagnosis of advanced/metastatic adenocarcinoma of the lung. For those with mixed histology, the adenocarcinoma must be the predominant histology.

3.1.2 Patients must have measurable disease, defined as at least one lesion that can be accurately measured in at least one dimension (longest diameter to be recorded for non-nodal lesions and short axis for nodal lesions) as >20 mm with conventional techniques or as >10 mm with spiral CT scan, MRI, or calipers by clinical exam. See Section 8 for the evaluation of measurable disease.

3.1.3 Patients must be chemotherapy-naïve or have completed adjuvant chemotherapy >6 months prior for NSCLC. Patients may have received prior radiation and/or targeted therapy. Patients with EGFR mutation or ALK gene-rearrangement previously treated with a TKI will be allowed to enroll at time of progression. Prior radiotherapy must have been completed at least 1 week prior to starting on treatment.

3.1.4 Age >18 Years.

3.1.5 ECOG performance status <1.

3.1.6 Life Expectancy of Greater than 6 Months.

3.1.7 Screening laboratory values must meet the following criteria and should be obtained within 7 days prior to randomization/registration

WBC ≥2000/μL

Neutrophils ≥500/μL

Platelets ≥100×103/μL

Hemoglobin ≥9.0 g/dL

Serum creatinine ≥1.5 ×ULN or creatinine clearance (CrCl) ≥40 mL/min (if using the Cockcroft-Gault formula below):

Female CrCl=(140−age in years)×weight in kg×0.85

72×serum creatinine in mg/dL

Male CrCl=(140−age in years)×weight in kg×1.00

72×serum creatinine in mg/dL

AST/ALT ≤3×ULN

Total Bilirubin ≤1.5×ULN (except subjects with Gilbert Syndrome, who can have total bilirubin <3.0 mg/dL)

3.1.8 have Archival Tissue Available or be Able to Undergo a Fresh Biopsy where Clinically Feasible after Discussion with the Sponsor.

3.1.9 Women of childbearing potential (WOCBP)*** must use appropriate method(s) of contraception, defined as: hormonal or barrier method of birth control; abstinence. WOCBP should use an adequate method to avoid pregnancy for 23 weeks (30 days plus the time required for nivolumab to undergo five half-lives) after the last dose of investigational drug. Women of childbearing potential must have a negative serum or urine pregnancy test (minimum sensitivity 25 IU/L or equivalent units of HCG) within 24 hours prior to the start of nivolumab. Women must not be breastfeeding.

3.1.10 Men who are sexually active with WOCBP must use any contraceptive method with a failure rate of less than 1% per year. Men receiving nivolumab and who are sexually active with WOCBP will be instructed to adhere to contraception for a period of 31 weeks after the last dose of investigational product Women who are not of childbearing potential (ie, who are postmenopausal or surgically sterile as well as azoospermic men do not require contraception.

3.1.11 Ability to Understand and the Willingness to Sign a Written Informed Consent Document.

For the purpose of this document, a woman is considered of childbearing potential (WOCBP) i.e., fertile, following menarche and until becoming post-menopausal unless permanently sterile. Permanent sterilization methods include hysterectomy, bilateral salpingectomy, and bilateral oophorectomy.

A postmenopausal state is defined as no menses for 12 months without an alternative medical cause. A high follicle stimulating hormone (FSH) level in the postmenopausal range may be used to confirm a post-menopausal state in women not using hormonal contraception or hormonal replacement therapy. However, in the absence of 12 months of amenorrhea, a single FSH measurement is insufficient.

Women of childbearing potential (WOCBP) receiving nivolumab will be instructed to adhere to contraception for a period of 23 weeks after the last dose of investigational product. Men receiving nivolumab and who are sexually active with WOCBP will be instructed to adhere to contraception for a period of 31 weeks after the last dose of investigational product. These durations have been calculated using the upper limit of the half-life for nivolumab (25 days) and are based on the protocol requirement that WOCBP use contraception for 5 half-lives plus 30 days and men who are sexually active with WOCBP use contraception for 5 half-lives plus 90 days.

3.2. Exclusion Criteria 3.2.1 Patients are excluded if they have symptomatic untreated brain metastases or leptomeningeal metastases. Subjects with a prior history of symptomatic brain metastases are eligible if metastases have been treated with external brain irradiation, and there is no magnetic resonance imaging (MRI) evidence of progression for a minimum of 14 days after treatment is complete and within 14 days prior to the first dose of nivolumab administration. There must also be no requirement for immunosuppressive doses of systemic corticosteroids (>10 mg/day prednisone equivalents) for at least 2 weeks prior to study drug administration. Patients with prior radiosurgery may enroll after 3 days as long as all adverse events are ≤grade 1.

3.2.2 Patients Who have had Targeted Therapy (e.g., Erlotinib) within 2 Weeks Prior to Starting on Treatment.

3.2.3 Allergies and Adverse Drug Reaction

History of allergy to study drug components

History of severe hypersensitivity reaction to any monoclonal antibody 3.2.4 Patients Who are Receiving any Other Investigational Agents.

3.2.5 Patients with an active, known, or suspected autoimmune disease within the last 5 years. Subjects are permitted to enroll if they have vitiligo, type I diabetes mellitus, residual hypothyroidism due to autoimmune condition only requiring hormone replacement, psoriasis not requiring systemic treatment, or conditions not expected to recur in the absence of an external trigger.

3.2.6 Patients that have a condition requiring systemic treatment with either corticosteroids (>10 mg daily prednisone equivalents) or other immunosuppressive medications within 14 days of study drug administration. Inhaled or topical steroids and adrenal replacement doses >10 mg daily prednisone equivalents are permitted in the absence of active autoimmune disease. Subjects are permitted to use topical, ocular, intra-articular, intranasal, and inhalational corticosteroids (with minimal systemic absorption). Physiologic replacement doses of systemic corticosteroids are permitted, even if >10 mg/day prednisone equivalents. A brief course (≤28 days) of corticosteroids for prophylaxis (eg, contrast dye allergy) or for treatment of non-autoimmune conditions (eg, delayed-type hypersensitivity reaction caused by contact allergen) is permitted.

3.2.7 Uncontrolled intercurrent illness including but not limited to, ongoing or active infection, symptomatic congestive heart failure, unstable angina pectoris, cardiac arrhythmia, or psychiatric illness/social situations that would limit compliance with study requirements.

3.2.8 Pregnant or Lactating Female.

3.2.9 Patients with known HIV infection, known acquired immunodeficiency syndrome (AIDS), or other conditions known to produce immunodeficiency are excluded due to the fact that the any potential clinical efficacy would require immune responsiveness.

3.2.10 Second Primary Malignancy, Other than In Situ Malignancies or Adequately Treated Basal Cell Carcinoma of the Skin or Other Malignancy Treated at Least 2 Years Previously with No Evidence of Recurrence.

3.2.11 Prior use of a PD1 or PDL1 inhibitor, anti-CTLA 4 antibody or any other antibody or drug that specifically target immune checkpoint pathways or.

3.2.12 Uncontrolled Interstitial Lung Disease 3.2.13 Patients who test positive for hepatitis B virus surface antigen (HBV sAg) or hepatitis C virus ribonucleic acid (HCV antibody) indicating acute or chronic infection. (Subjects who are hepatitis C antibody positive may be enrolled if they are confirmed with negative viral load at screening.)

3.3. Inclusion of Women and Minorities

Both men and women of all races and ethnic groups are eligible for this trial.

4 Treatment Plan 4.1. Randomization Procedure

Patients who successfully complete the screening exams for initial registration will be randomized into one of two study arms. The study Biostatistician will generate a Flow Chart for Randomization. This Flow Chart will be held in confidence by the Biostatistician and the Clinical Trials Coordinator. The individual randomization assignment will be released by the Clinical Trials Coordinator only after the patient signs the informed consent document and successfully completes the screening process.

Treatment of patients on Arm A: Those patients randomized to Arm A will receive nivolumab alone.

Treatment of patients on Arm B: Those patients randomized to Arm B will receive vaccines plus nivolumab.

4.2. Study Design 4.2.1. Phase I Trial

Both of the investigational agents that will be used in the phase II trial (GM.CD40L vaccine and nivolumab) have been tested individually as single agents in phase I clinical trials. The combination of the vaccine with anti-PD-1 has not yet been tested; therefore, we will first conduct a phase I trial of this combination. We will start with the dose planned for the phase II trial with a provision for dose de-escalation in the event of dose-limiting toxicities (DLTs). The 6 patients who we expect to enroll in the phase I part will be observed through a 21-day DLT period before initiating enrollment in the phase II trial. During the phase 1 portion a maximum of 2 patients will be enrolled per week.

Eligible patients are entered in cohorts of six at the first dose level. Doses are not escalated over the course of treatment of an individual patient. If 2 or more patients experience grade 3 hematologic or grade 3 nonhematologic toxicity (DLT is further defined in Section 6.1) in dose level 1, then dose de-escalation will occur. Dose level −1 will follow the same rules.

If there is no more than 1 DLT within a 21-day period, then the phase II portion of the trial will initiate. No dose escalation is planned beyond dose level 1. The recommended Phase II dose will be defined as the highest dose level of GMCD40L vaccine that induced DLT in fewer than 33% of patients (ie, one dose level below that which induced DLT in at least two of six patients).

Due to technical limitations, it is not feasible to escalate the dose of the vaccine beyond 30×10$^6$ cells per injection; therefore, the MTD may not be reached in this study. If this is the case then, the highest dose level will be used in the phase II component.

TABLE 4

Phase I Dose Escalation Table

| Dose level** | Nivolumab IV q 2 weeks | GM.CD40L* |
|---|---|---|
| −1 | 1 mg/kg | 1.0 mL |
| 1 (start) | 3 mg/kg | 1.0 mL |

*q 2 weeks ×4, then monthly ×4, then Q 3 month booster until progression, intolerance, or patient withdrawal.
**Alternate dosing schedules may be explored.
Vaccine contains: 7.5 × 10$^6$ irradiated H1944 tumor cells, 7.5 × 10$^6$ irradiated H2122 cells, and 15 × 10$^6$ GM.CD40L cells (1.1 mL).
Patients will be treated until progression or intolerance.

4.2.2. Randomized Phase I Trial

The randomized phase II trial will be for first-line advanced-stage/metastatic lung adenocarcinoma patients. As diagrammed in FIG. 2, there will be 2 arms that will differ with respect to the immunotherapy part: patients in Arm A will receive anti-PD-1, and patients in Arm B will receive anti-PD-1 plus vaccines.

The primary objective of the trial will be proof-of-concept that expanding the number of tumor-specific T cells with the GM.CD40L vaccine will improve the clinical efficacy of anti-PD-1.

Immunotherapy. After screening and randomization, patients will first be treated with immunotherapy: in Arm A patients will receive 3 mg/kg anti-PD-1 (nivolumab) every 2 weeks. In Arm B (and the Phase I portion), patients will be given the same dose and schedule of anti-PD-1. In addition they will receive GM.CD40L intradermal vaccine injections at four separate sites (bilateral upper arms and bilateral upper thighs) every 2 weeks times 4, followed by every 4 weeks times 4 (Table 4). The rationale for this schedule is based on our prior dosing in our phase I and II studies as well as to stay in line with the every 2-week dosing of nivolumab. The vaccine will consist of GM.CD40L cells admixed with an equivalent number of allogeneic tumor cells.

4.2.3. Randomization Procedure for Phase !

Patients who successfully complete the screening exams for initial registration will be randomized into one of two study arms. Randomization will be accomplished using the Moffitt Cancer Center web-based Subject Registration and Randomization System (SRAR). The SRAR program is accessed using an individual secure identification key that authenticates the user into the Moffitt network 4.2.4. Patient numbering Once a patient is enrolled in the study, he/she will be assigned a simple 3 digit number, with the first patient assigned to 001 and so on. A separate spreadsheet with password protection will be maintained that contains the patient study number along with personally identifiable information. Password protection will be maintained in order to keep patient information strictly confidential. Upon signing the informed consent form, the patient will be assigned a subject number by the investigator or his/her designee. Once assigned to a patient, a subject number will not be reused. If the patient fails to be started on treatment for any reason, the reason will be entered on the Eligibility Tab in OnCore, and his/her demographic information will be entered on the Demography Tab in OnCore. All laboratory, radiologic, and pathologic data collected on trial participants will be assigned the unique treatment number and stored in the OnCore system database.

4.2.5. GM.CD40L Vaccine Production

Moffitt Cancer Center houses a cell therapy core that is experienced in the Cell Bank generation, storage, qualification, characterization, production cultures, product testing, and infection quality controls and testing of the therapeutic entity all under GMP conditions. They have experience in the treatment of over 70 NSCLC patients across 3 clinical trials, all which operate under the governance of an IND, OBA, and RAC oversight.

The details of the vaccine production will be outlined in Section 7. Briefly, vials of the GM.CD40L cell line and the lung adenocarcinoma cell lines will be stored under cGMP conditions, meet all lot release criteria, and are stored in a liquid nitrogen freezer. On the day of immunization a vial of each cell type will be thawed, washed, and combined to create the final vaccine.

4.2.6. Safety Assessments

NCI CTCAE version 4.0 will be used to assess toxicities on all patients in this study. Although the vaccine and anti-PD-1 are each generally well tolerated, toxicities do occur. Careful toxicity assessment will be performed with standard laboratory studies (CBC, BUN, creatinine, electrolytes, and LFTs) before each treatment. In addition, a medical history and physical examination will be performed monthly. Toxicities related to induction of autoimmunity can occur with the anti-PD-1. Careful, frequent clinical evaluation for the development of autoimmunity symptoms will be performed. Detailed plans for management of these toxicities will be present in the clinical protocol. Patients who develop uncontrolled grade 3/4 pneumonitis will permanently discontinue anti-PD-1. Patients will be treated in the Moffitt Clinical Research Unit, which is staffed by nurses experienced in the management of infusion reactions and cytokine release syndrome. Moffitt Cancer Center is also very experienced in managing the toxicities associated with nivolumab, as we have treated over 50 NSCLC patients with nivolumab.

All SAEs with a determination of SAE-relatedness to the investigational therapy will be reported as described in the data and safety monitoring plan detailed in the protocol (See Section 6, Adverse events).

4.2.7. Efficacy Assessments

Radiographic assessments will be performed every 6 weeks and be based on Response Evaluation Criteria in Solid Tumors v1.1 (RECIST v1.1). Patients who are found to have stable disease (SD), partial response (PR), or complete response (CR) at re-staging after the initial vaccines will receive additional vaccines every 3 months until evidence of disease progression. Response rate, overall survival, and progression-free survival will be determined. Subjects with progressive disease by RECIST v1.1 but without rapid clinical deterioration may continue to be treated at the discretion of the investigator.

human serum albumin. The reconstituted vaccine will be drawn up in a 1 cc syringe with an 18G needle. A 0.1 mL aliquot will be dispensed from the syringe for microbiological testing (including Gram stain and sterility culture). All air bubbles will be expressed, and the 18G needle will be replaced with a syringe cap for transport. If the testing reveals an absence of microbial contamination, the vaccine will be considered adequate for clinical use and will then be transported to the Cell Therapy Staging Laboratory at the Moffitt Cancer Center in a thermal insulated cooler (2-8° C.). The vaccine will be transported to the Clinical Research Unit after the label has been verified by two members of the Cell Therapy Facility. This cell suspension will be injected intradermally into four separate injection sites (one intradermal injection in each of four nodal basins; bilateral axillary and bilateral inguinal nodal basins). Each injection will consist of approximately 0.25 ml of cell suspension. Patients will be monitored in the Clinical Research Unit at the Moffitt Cancer Center for acute toxicity for 0.5 hour after the

TABLE 5

Study Calendar*

|  | Screening[A] | C1D1 | C1D15 | C2D1 | C2D15 | C3-6, D1[B] | C3-6, D15 | D30 Follow-up (+/−14 days) |
|---|---|---|---|---|---|---|---|---|
| Vitals, including weight | X | X | X | X | X | X | X | X |
| H&P/ECOG | X | X | X | X |  | X |  | X |
| CBC w/ Diff[C] | X | X | X | X | X | X | X | X |
| CMP[C] | X | X | X | X | X | X | X | X |
| Magnesium[C] | X | X | X | X | X | X | X | X |
| Pregnancy, Urine or serum[D] | X | X |  | X |  | X |  | X |
| TSH/FT4/FT3[C] | X | X | X | X | X | X | X | X |
| Amylase/Lipase[C] | X | X | X | X | X | X | X | X |
| LDH[C] | X | X | X | X | X | X | X | X |
| EKG | X |  |  |  |  |  |  |  |
| Echo/Muga | X |  |  |  |  |  |  |  |
| Tumor Measurement[E] | X |  |  | X | X | X |  |  |
| Toxicity Assessment | X | X | X | X | X |  | X | X |
| Archival tumor collection | X |  |  |  |  |  |  |  |
| Nivolumab (Arms A and B) |  | X | X | X | X | X | X |  |
| GMCD40L (Arm B) |  | X | X | X | X | X | X |  |

*Footnotes:
All tests, visits, and dosing have a window of +/−7 days.
[A]Baseline evaluations, Scans and x-rays must be done 28 days prior to the start of therapy.
[B]Following cycle 6 (Dose 8 of the vaccine), those with SD or better will remain on nivolumab every 2 weeks and receive booster vaccines once every 3 months.
[C]Laboratory testing prior to each dose: Within 72 hrs prior to re-dosing to include CBC w/ differential, LFTs, BUN or serum urea level, creatinine, Ca, Mg, Na, K, Cl, LDH, Glucose, amylase, lipase, TSH (with reflexive Free T4 and Free T3)
[D]A serum or urine pregnancy testing is required within 24 hrs of study enrollment or randomization, then every 4-6 weeks. After discontinuation from nivolumab these should be repeated at approximately 30 days and approximately 70 days.
[E]Tumor measurements will be performed every 6 weeks.

4.3. Agent Administration

Treatment will be administered on an outpatient basis.

Reported adverse events and potential risks are described in Section 6. Appropriate dose modifications are described in Section 5. No investigational or commercial agents or therapies other than those described below may be administered with the intent to treat the patient's malignancy.

4.3.1 GM.CD40L Vaccine: Production and Administration

One vial containing $7.5 \times 10^6$ irradiated H1944 tumor cells, 1 vial containing $7.5 \times 10^6$ irradiated H2122 cells, and 1 vial containing $15 \times 10^6$ radiated GM.CD40L cells will be thawed rapidly by immersion in a 37° C. waterbath, combined, diluted in 10 mL PlasmaLyte A supplemented with 0.1% human serum albumin at 37° C., centrifuged, and resuspended in a final volume of 1.1 mL PlasmaLyteA/0.1% injections. After vaccine #4, observation specifically for the vaccine is not required if no prior reactions have been noted. Potential toxicities include erythema, pain, and edema. Subjects who are not stable to be released at 0.5 hours after infusion should continue to be monitored until stable. Hospital admissions for overnight monitoring will not be considered an SAE unless the event meets criteria for seriousness other than hospitalization.

4.3.2 Nivolumab (Anti-PD-1): Preparation and Infusion

Nivolumab vials must be stored in the refrigerator at 2-8° C., protected from light and freezing. If stored in a glass front refrigerator, vials should be stored in the carton. Recommended safety measures for preparation and handling of nivolumab include laboratory coats and gloves. After nivolumab has been prepared for administration, the total storage time (combination of refrigeration and room temperature) is not to exceed 24 hours. Stability data for nivolumab following dilution and transfer to the IV bag supports 24 hours at 2-8° C. in the refrigerator or up to 6 hours at room temperature/under room light. Nivolumab must be refrigerated beyond 6 hours up to maximum total of 24 hours. Care must be taken to assure sterility of the prepared solution as the product does not contain any anti-microbial preservative or bacteriostatic agent. No incompatibilities between nivolumab and polyolefin bags have been observed.

Nivolumab is to be administered as a 60-minute IV infusion, using a volumetric pump with a 0.2 micron in-line filter at the protocol-specified doses. It is not to be administered as an IV push or bolus injection. At the end of the infusion, flush the line with a sufficient quantity of normal saline.

Subjects will receive treatment with nivolumab as a 60-minute IV infusion on Day 1 and 15 of each 28-day cycle. There will be no dose escalations or reductions allowed. Treatment may be delayed for up to a maximum of 21 days from the scheduled re-treatment date. Subjects may be dosed no less than 12 days from the previous dose. There are no premedications recommended for nivolumab on the first cycle. If an allergic reaction is noted, then acetaminophen 650 mg PO and diphenyhydramine 50 mg PO may be administered prior to nivolumab infusion.

Nivolumab will be given every two weeks at a dose of 3 mg/kg. Patients may be dosed no less than 12 days from the previous dose of drug.

The dosing calculations should be based on the actual body weight. If the subject's weight on the day of dosing differs by >10% from the weight used to calculate the original dose, the dose must be recalculated. All doses should be rounded to the nearest milligram. There will be no dose modifications allowed.

4.3.3. Dose Modifications

Intra-patient dose reductions or dose escalations are not permitted.

4.3.4. Dose Delay Criteria

Because of the potential for clinically meaningful nivolumab-related AEs requiring early recognition and prompt intervention, management algorithms have been developed for suspected AEs of selected categories. [See current Investigator Brochure and Appendix 2 for citation examples].

Dose delay criteria apply for all drug-related adverse events (regardless of whether or not the event is attributed to nivolumab). All study drugs must be delayed until treatment can resume.

Dose delay criteria apply for all drug-related AEs. Nivolumab must be delayed until treatment can resume. Nivolumab Administration should be Delayed for the Following:

Any Grade ≥2 non-skin, drug-related AE, with the following exceptions:
Grade 2 drug-related fatigue or laboratory abnormalities do not require a treatment delay.
Any Grade 3 skin, drug-related AE.
Any Grade 3 drug-related laboratory abnormality, with the following exceptions for lymphopenia, leukopenia, AST, ALT, total bilirubin, or asymptomatic amylase or lipase:
Grade 3 lymphopenia or leukopenia does not require dose delay.
If a subject has a baseline AST, ALT, or total bilirubin that is within normal limits, delay dosing for drug-related Grade Z 2 toxicity.
If a subject has baseline AST, ALT, or total bilirubin within the Grade 1 toxicity range, delay dosing for drug-related Grade Z 3 toxicity.
Any AE, laboratory abnormality, or intercurrent illness that, in the judgment of the investigator, warrants delaying the dose of study medication.

Criteria to Resume Treatment

Subjects may resume treatment with study drug when the drug-related AE(s) resolve to Grade ≤1 or baseline value, with the following exceptions:
Subjects may resume treatment in the presence of Grade 2 fatigue.
Subjects who have not experienced a Grade 3 drug-related skin AE may resume treatment in the presence of Grade 2 skin toxicity.
Subjects with baseline Grade 1 AST/ALT or total bilirubin who require dose delays for reasons other than a 2-grade shift in AST/ALT or total bilirubin may resume treatment in the presence of Grade 2 AST/ALT OR total bilirubin.
Subjects with combined Grade 2 AST/ALT AND total bilirubin values meeting discontinuation parameters should have treatment permanently discontinued.
Drug-related pulmonary toxicity, diarrhea, or colitis must have resolved to baseline before treatment is resumed.
Drug-related endocrinopathies adequately controlled with only physiologic hormone replacement may resume treatment.

If the criteria to resume treatment are met, the subject should restart treatment at the next scheduled timepoint per protocol. However, if the treatment is delayed past the next scheduled timepoint per protocol, the next scheduled timepoint will be delayed until dosing resumes.

If treatment is delayed >6 weeks, the subject must be permanently discontinued from study therapy, except as specified in discontinuation section.

Management Algorithms

Immuno-oncology (I-O) agents are associated with AEs that can differ in severity and duration than AEs caused by other therapeutic classes. Nivolumab is considered an immuno-oncology agent in this protocol. Early recognition and management of AEs associated with immuno-oncology agents may mitigate severe toxicity. Management algorithms have been developed to assist investigators in assessing and managing the following groups of AEs:
Gastrointestinal, Renal, Pulmonary, Hepatic, Endocrinopathies, Skin, Neurological.

For subjects expected to require more than 4 weeks of corticosteroids or other immunosuppressants to manage an AE, consider recommendations provided in the algorithms. These algorithms are found in the Nivolumab IB [and in Appendix 2] of this protocol. The guidance provided in these algorithms should not replace the Investigator's medical judgment but should complement it.

Discontinuation Criteria

Treatment should be permanently discontinued for the following:
Any Grade 2 drug-related uveitis or eye pain or blurred vision that does not respond to topical therapy and does not improve to Grade 1 severity within the re-treatment period OR requires systemic treatment.
Any Grade 3 non-skin, drug-related adverse event lasting >7 days, with the following exceptions for drug-related laboratory abnormalities, uveitis, pneumonitis, bronchospasm, diarrhea, colitis, neurologic adverse event, hypersensitivity reactions, and infusion reactions.

Grade 3 drug-related uveitis, pneumonitis, bronchospasm, diarrhea, colitis, neurologic adverse event, hypersensitivity reaction, or infusion reaction of any duration requires discontinuation.

Grade 3 drug-related laboratory abnormalities do not require treatment discontinuation except those noted below.

Grade 3 drug-related thrombocytopenia >7 days or associated with bleeding requires discontinuation Any drug-related liver function test (LFT) abnormality that meets the following criteria require discontinuation:

AST or ALT >8×ULN

Total bilirubin >5×ULN

Concurrent AST or ALT >3×ULN and total bilirubin >2×ULN

Any Grade 4 drug-related adverse event or laboratory abnormality, except for the following events, which do not require discontinuation:

Isolated Grade 4 amylase or lipase abnormalities that are not associated with symptoms or clinical manifestations of pancreatitis and decrease to <Grade 4 within 1 week of onset.

Isolated Grade 4 electrolyte imbalances/abnormalities that are not associated with clinical sequelae and are corrected with supplementation/appropriate management within 72 hours of their onset.

Any dosing interruption lasting >6 weeks with the following exceptions:

Dosing interruptions to allow for prolonged steroid tapers to manage drug-related adverse events are allowed. Prior to re-initiating treatment in a subject with a dosing interruption lasting >6 weeks, the Investigator must be consulted. Tumor assessments should continue as per protocol even if dosing is interrupted.

Dosing interruptions >6 weeks that occur for non-drug-related reasons may be allowed if approved by the Investigator. Prior to re-initiating treatment in a subject with a dosing interruption lasting >6 weeks, the Investigator must be consulted. Tumor assessments should continue as per protocol even if dosing is interrupted.

Any adverse event, laboratory abnormality, or intercurrent illness which, in the judgment of the Investigator, presents a substantial clinical risk to the subject with continued nivolumab dosing.

Treatment of Nivolumab Related Infusion Reactions

Since nivolumab contains only human immunoglobulin protein sequences, it is unlikely to be immunogenic and induce infusion or hypersensitivity reactions. However, if such a reaction were to occur, it might manifest with fever, chills, rigors, headache, rash, pruritus, arthralgias, hypo- or hypertension, bronchospasm, or other symptoms.

All Grade 3 or 4 infusion reactions should be reported as an SAE if criteria are met. Infusion reactions should be graded according to NCI CTCAE 4.0 guidelines.

Treatment recommendations are provided below and may be modified based on local treatment standards and guidelines as appropriate:

For Grade 1 symptoms: (Mild reaction; infusion interruption not indicated; intervention not indicated)

Remain at bedside and monitor subject until recovery from symptoms. The following prophylactic premedications are recommended for future infusions: diphenhydramine 50 mg (or equivalent) and/or paracetamol 325 to 1000 mg (acetaminophen) at least 30 minutes before additional nivolumab administrations.

For Grade 2 symptoms: (Moderate reaction requires therapy or infusion interruption but responds promptly to symptomatic treatment [eg, antihistamines, non-steroidal anti-inflammatory drugs, narcotics, corticosteroids, bronchodilators, IV fluids]; prophylactic medications indicated for 24 hours).

Stop the nivolumab infusion, begin an IV infusion of normal saline, and treat the subject with diphenhydramine 50 mg IV (or equivalent) and/or paracetamol 325 to 1000 mg (acetaminophen); remain at bedside and monitor subject until resolution of symptoms. Corticosteroid or bronchodilator therapy may also be administered as appropriate. If the infusion is interrupted, then restart the infusion at 50% of the original infusion rate when symptoms resolve; if no further complications ensue after 30 minutes, the rate may be increased to 100% of the original infusion rate. Monitor subject closely. If symptoms recur then no further nivolumab will be administered at that visit. Administer diphenhydramine 50 mg IV, and remain at bedside and monitor the subject until resolution of symptoms. The amount of study drug infused must be recorded on the electronic case report form (eCRF). The following prophylactic premedications are recommended for future infusions: diphenhydramine 50 mg (or equivalent) and/or paracetamol 325 to 1000 mg (acetaminophen) should be administered at least 30 minutes before additional nivolumab administrations. If necessary, corticosteroids (recommended dose: up to 25 mg of IV hydrocortisone or equivalent) may be used.

For Grade 3 or Grade 4 symptoms: (Severe reaction, Grade 3: prolonged [i.e. not rapidly responsive to symptomatic medication and/or brief interruption of infusion]; recurrence of symptoms following initial improvement; hospitalization indicated for other clinical sequelae [eg, renal impairment, pulmonary infiltrates]). Grade 4: (life threatening; pressor or ventilatory support indicated).

Immediately discontinue infusion of nivolumab. Begin an IV infusion of normal saline, and treat the subject as follows. Recommend bronchodilators, epinephrine 0.2 to 1 mg of a 1:1,000 solution for subcutaneous administration or 0.1 to 0.25 mg of a 1:10,000 solution injected slowly for IV administration, and/or diphenhydramine 50 mg IV with methylprednisolone 100 mg IV (or equivalent), as needed. Subject should be monitored until the investigator is comfortable that the symptoms will not recur. Nivolumab will be permanently discontinued. Investigators should follow their institutional guidelines for the treatment of anaphylaxis. Remain at bedside and monitor subject until recovery from symptoms. In the case of late-occurring hypersensitivity symptoms (eg, appearance of a localized or generalized pruritus within 1 week after treatment), symptomatic treatment may be given (eg, oral antihistamine, or corticosteroids).

4.4. General Concomitant Therapy 4.4.1 Permitted Therapies

Subjects are permitted to use topical, ocular, intra-articular, intranasal, and inhalational corticosteroids (with minimal systemic absorption). Physiologic replacement doses of systemic corticosteroids are permitted, even if >10 mg/day prednisone equivalents. A brief course of corticosteroids for prophylaxis (eg, contrast dye allergy) or for treatment of non-autoimmune conditions (eg, delayed-type hypersensitivity reaction caused by contact allergen) is permitted.

Growth factors for neutrophils or RBCs used in accordance with established guidelines are allowed.

Palliative (limited-field) radiation therapy is permitted, if all of the following criteria are met:

1. Repeat imaging demonstrates no new sites of bone metastases.
2. The lesion being considered for palliative radiation is not a target lesion.

4.5. Supportive Care Guidelines

Immune-related adverse events may occur on this trial.

They include renal, hepatic, neurologic, endocrine, GI, pulmonary and skin related toxicity. See Appendix 2 for management algorithms.

4.6. Duration of Therapy 4.6.1 Immunotherapy

Patients will receive continuous nivolumab every 2 weeks with the GM.CD40L given every 2 weeks×4, then every months×4, and then as boosters every 3 months until evidence of progressive disease, patient withdraws from the study or the treatment, or intolerable toxicity.

General Reasons to Discontinue Treatment.

In the absence of treatment delays due to adverse event(s), treatment may continue for the time described above or until one of the following criteria applies:

Disease progression,
Intercurrent illness that prevents further administration of treatment,
Unacceptable adverse event(s),
Patient decides to withdraw from the study, or
General or specific changes in the patient's condition render the patient unacceptable for further treatment in the judgment of the investigator.

4.6. Duration of Follow-Up

Patients will be followed for 30 days after removal from study, initiation of new therapy or until death, whichever occurs first. Patients removed from study for unacceptable adverse event(s) will be followed until resolution or stabilization of the adverse event.

4.7. Criteria for Removal from Study

Patients will be removed from study when any of the criteria listed in Section 4.3 applies. The reason for study removal and the date the patient was removed must be documented into OnCore.

5 Dosing Delays 5.1. GM.CD40L Vaccine

There will be no dose reductions.

5.2. Nivolumab (Anti-PD-1)

There will be no dose reductions. Appendix 2 outlines the management guidelines for the immune related toxicities.

5.2.1. Dermatitis

For any Grade 3 drug-related dermatitis, omit nivolumab until next cycle and resolution to less than Grade 2.

5.2.2. LFT Abnormalities

For any 2-Grade drug-related shift from baseline in AST, ALT, or T. bilirubin, omit nivolumab until next cycle and resolution to less than Grade 2.

5.2.3. Pneumonitis

Grade 1 or 2: When lung parenchymal infiltrates and symptoms resolve after the steroid taper, then resume nivolumab.

Grade 3 or 4: Nivolumab will be permanently discontinued.

5.2.4. Diarrhea and Colitis

Grade 1 or 2: Begin with symptomatic treatment with Imodium. If persistent, then treat with oral corticosteroid therapy. If symptoms persist for greater than 2 weeks or if symptoms worsen, then manage as high-grade event.

Grade 3 or 4: Increase monitoring and institute high-dose corticosteroid therapy, followed by gradual steroid taper over 4 weeks. Hospitalization for intravenous steroids and/or hydration may be necessary. Nivolumab will be held until resolution of symptoms. If symptoms do not respond within 5 days then consider infliximab.

5.2.5. Autoimmune Endocrinopathies

Hold nivolumab until hormone replacement therapy restores physiologic function except for grade 2 or less thyroid dysfunction or asymptomatic thyroid dysfunction.

6 Adverse Events: Description and Reporting Requirements 6.1. Dose-Limiting Toxicity Definition DLT will be defined as an intervention-specific acute toxicity; i.e., occurrence within 28 days of drug administration, that precludes further dose escalation. For the purpose of this investigation, grading of DLTs will be according to the NCI Common Toxicity Criteria for Adverse Events (CTCAE), Version 4:

A DLT will be defined as any Grade 3 or higher treatment-related toxicity (excluding alopecia or fatigue lasting <7 days) that occurs during the DLT evaluation period, including but not limited to:

Any Grade 4 immune-related AE (irAE) regardless of duration.
Any ≥Grade 3 colitis regardless of duration.
Any Grade 3 or Grade 4 non-infectious pneumonitis irrespective of duration.
Any Grade 3 irAE excluding colitis and pneumonitis, that does not downgrade to ≤Grade 2 within 3 days after onset of the event despite maximal supportive care including systemic corticosteroids or downgrade to ≤Grade 1 or baseline within 14 days.
Any Grade 2 pneumonitis that does not resolve to ≤Grade 1 within 3 days of the initiation of maximal supportive care.
Liver transaminase elevation higher than 8×upper limit of normal (ULN) or total bilirubin higher than 5×ULN.
Grade 4 neutropenia and thrombocytopenia that does not resolve to ≤Grade 3 within ≤7 days and Grade 3 thrombocytopenia associated with any clinically important bleeding.

The definition excludes the following conditions:

Grade 3 endocrinopathy that is managed with or without systemic corticosteroid therapy and/or hormone replacement therapy and the subject is asymptomatic.
Grade 3 inflammatory reaction attributed to a local anti-tumor response (eg, inflammatory reaction at sites of metastatic disease, lymph nodes, etc) that resolves to ≤Grade 1 within 30 days.
Concurrent vitiligo or alopecia of any AE grade.

Immune-related AEs are defined as AEs of immune nature (ie, inflammatory) in the absence of a clear alternative etiology. In the absence of clinical abnormality, repeat laboratory testing will be conducted to confirm significant laboratory findings prior to designation as a DLT.

While the rules for adjudicating DLTs in the context of dose escalation are specified above, an AE not listed above may be defined as a DLT after a consultation with the sponsor and investigators, based on the emerging safety profile.

6.2. Adverse Event Definitions

An Adverse Event (AE) is defined as any new untoward medical occurrence or worsening of a preexisting medical condition in a clinical investigation subject administered an investigational (medicinal) product and that does not necessarily have a causal relationship with this treatment. An AE can therefore be any unfavorable and unintended sign (such as an abnormal laboratory finding), symptom, or disease temporally associated with the use of investigational product, whether or not considered related to the investigational product.

The causal relationship to study drug is determined by a physician and should be used to assess all adverse events (AE). The casual relationship can be one of the following:

Related: There is a reasonable causal relationship between study drug administration and the AE.

Not related: There is not a reasonable causal relationship between study drug administration and the AE.

The term "reasonable causal relationship" means there is evidence to suggest a causal relationship.

Adverse events can be spontaneously reported or elicited during open-ended questioning, examination, or evaluation of a subject. (In order to prevent reporting bias, subjects should not be questioned regarding the specific occurrence of one or more AEs.)

A nonserious adverse event is an AE not classified as serious.

6.2.1. Nonserlous Adverse Event Collection and Reporting

The collection of nonserious AE information should begin at initiation of study drug. All nonserious adverse events (not only those deemed to be treatment-related) should be collected continuously during the treatment period and for a minimum of 100 days following the last dose of study treatment.

Adverse events will be assessed according to the Common Toxicity Criteria for Adverse Events (CTCAE) version 4.0. If CTCAE grading does not exist for an adverse event, the severity grades 1-4, will be used. CTCAE grade 5 (death) will not be used in this study; rather, this information will be collected in the End of Treatment or Survival Information CRF page. Adverse event monitoring should be continued for 30 days following the last dose of study treatment.

Adverse events (but not serious adverse events) occurring before starting study treatment but after signing the informed consent form are recorded on the Medical History/Current Medical Conditions Electronic Case Report Form (OnCore).

Abnormal Lab values, vital signs or test results that do not induce clinical signs/symptoms or require therapy, will not be considered clinically significant and will not be reported as Adverse Events. Isolated abnormal laboratory values that are considered clinically significant (e.g., cause study discontinuation or constitutes in and of itself a Serious Adverse Event) should be recorded on the Adverse Events CRF. SAEs occurring after initiation of treatment are recorded on the Adverse Event CRF.

6.2.2. Laboratory Test Abnormalities

The following laboratory abnormalities should be documented and reported appropriately:

Any laboratory test result that is clinically significant or meets the definition of an SAE.

Any laboratory abnormality that required the subject to have study drug discontinued or interrupted.

Any laboratory abnormality that required the subject to receive specific corrective therapy.

6.2.3. Pregnancy

If, following initiation of the investigational product, it is subsequently discovered that a study subject is pregnant or may have been pregnant at the time of investigational product exposure, including during at least 6 half lives after product administration, the investigational product will be permanently discontinued in an appropriate manner (eg, dose tapering if necessary for subject safety).

The investigator must immediately notify Worldwide Safety @BMS of this event via the Pregnancy Surveillance Form in accordance with SAE reporting procedures.

Follow-up information regarding the course of the pregnancy, including perinatal and neonatal outcome and, where applicable, offspring information must be reported on the Pregnancy Surveillance Form [provided upon request from BMS]

Any pregnancy that occurs in a female partner of a male study participant should be reported to BMS. Information on this pregnancy will be collected on the Pregnancy Surveillance Form.

6.2.4. Overdose

An overdose is defined as the accidental or intentional administration of any dose of a product that is considered both excessive and medically important. All occurrences of overdose must be reported as an SAE.

6.2.5. Other Safety Considerations

Any significant worsening noted during interim or final physical examinations, electrocardiograms, x-rays, and any other potential safety assessments, whether or not these procedures are required by the protocol, should also be recorded as a nonserious or serious AE, as appropriate, and reported accordingly.

6.3. Serious, Life-Threatening, or Unexpected Adverse Experience (21 CFR 312.32)

6.3.1. Definition

A Serious Adverse Event (SAE) is any untoward medical occurrence that at any dose:

results in death is life-threatening (defined as an event in which the subject was at risk of death at the time of the event; it does not refer to an event which hypothetically might have caused death if it were more severe)

requires inpatient hospitalization or causes prolongation of existing hospitalization (see NOTE below)

results in persistent or significant disability/incapacity is a congenital anomaly/birth defect is an important medical event (defined as a medical event(s) that may not be immediately life-threatening or result in death or hospitalization but, based upon appropriate medical and scientific judgment, may jeopardize the subject or may require intervention [eg, medical, surgical] to prevent one of the other serious outcomes listed in the definition above). Examples of such events include, but are not limited to, intensive treatment in an emergency room or at home for allergic bronchospasm; blood dyscrasias, or convulsions that do not result in hospitalization.

Potential drug induced liver injury (DILI) is also considered an important medical event.

Suspected transmission of an infectious agent (eg, pathogenic or nonpathogenic) via the study drug is an SAE.

Although pregnancy, overdose, and cancer are not always serious by regulatory definition, these events must be handled as SAEs.

NOTE: The following hospitalizations are not considered SAEs in this clinical study:

a visit to the emergency room or other hospital department <24 hours, that does not result in admission (unless considered an important medical or life-threatening event)

elective surgery, planned prior to signing consent admissions as per protocol for a planned medical/surgical procedure routine health assessment requiring admission for baseline/trending of health status (eg, routine colonoscopy)

Medical/surgical admission other than to remedy ill health and planned prior to entry into the study. Appropriate documentation is required in these cases Admission encountered for another life circumstance that carries no bearing on health status and requires no medical/surgical intervention (eg, lack of housing, economic inadequacy, caregiver respite, family circumstances, administrative reason). Potential Drug-Induced Liver Injury (DILI)

Wherever possible, timely confirmation of initial liver-related laboratory abnormalities should occur prior to the reporting of a potential DILI event. All occurrences of potential DILIs, meeting the defined criteria, must be reported as SAEs. Potential drug induced liver injury is defined as:

1) ALT or AST elevation >3 times upper limit of normal (ULN) AND
2) Total bilirubin >2 times ULN, without initial findings of cholestasis (elevated serum alkaline phosphatase) AND
3) No other immediately apparent possible causes of AST/ALT elevation and hyperbilirubinemia, including, but not limited to, viral hepatitis, pre-existing chronic or acute liver disease, or the administration of other drug(s) known to be hepatotoxic. All SAE's will be reported for 100 days after the last protocol treatment. Any death or other serious adverse event which occurs more than 100 days after protocol treatment has ended but is felt to be treatment related must also be reported.

An unexpected adverse event is any research-related event which, in the opinion of the Principal Investigator was unforeseen at the time of its occurrence and involved risks to participants or others. An unanticipated event may be symptomatically and pathophysiologically related to an event listed in the labeling but differs because of greater specificity or severity.

Following the subject's written consent to participate in the study, all SAEs, whether related or not related to study drug, must be collected, including those thought to be associated with protocol-specified procedures. All SAEs must be collected that occur within 100 days of discontinuation of dosing.

All SAEs must be collected that occur during the screening period. If applicable, SAEs must be collected that relate to any protocol-specified procedure (eg, a follow-up skin biopsy). The investigator should report any SAE that occurs after these time periods that is believed to be related to study drug or protocol-specified procedure.

6.3.2. Serious Adverse Events

All SAE's will be reported for 100 days after the last protocol treatment. Any death or other serious adverse event which occurs more than 100 days after protocol treatment has ended but is felt to be treatment related must also be reported.

An unexpected adverse event is any research-related event which, in the opinion of the Principal Investigator was unforeseen at the time of its occurrence and involved risks to participants or others. An unanticipated event may be symptomatically and pathophysiologically related to an event listed in the labeling but differs because of greater specificity or severity.

Following the subject's written consent to participate in the study, all SAEs, whether related or not related to study drug, must be collected, including those thought to be associated with protocol-specified procedures. All SAEs must be collected that occur within 100 days of discontinuation of dosing.

All SAEs must be collected that occur during the screening period. If applicable, SAEs must be collected that relate to any protocol-specified procedure (eg, a follow-up skin biopsy). The investigator should report any SAE that occurs after these time periods that is believed to be related to study drug or protocol-specified procedure.

6.4. Relationship to Study Drug

The Principal Investigator will evaluate each adverse event to determine what might have caused the event or what interventions or conditions might have been associated with the event. Evaluation of an AE involves assessing the relationship of the event to investigational agents, disease, concomitant medications or other contributing causes. For each adverse event reported, attribution will be assigned using the following criteria:

| Code | Descriptor | Definition |
|---|---|---|
| 5 | Definite | The adverse event is clearly related to the investigational agent |
| 4 | Probable | The adverse event is likely related to the investigational agent |
| 3 | Possible | The adverse event may be related to the investigational agent |
| 2 | Unlikely | The adverse event is doubtfully related to the investigational agent |
| 1 | Unrelated | The adverse event is clearly not related to the investigational agent |

6.5. Procedure for Serious Adverse Event Reporting

The conduct of the study will comply with all FDA and USF institutional safety reporting requirements.

All serious adverse experience reports must include the patient number, age, sex, weight, severity of reaction (mild, moderate, severe), relationship to study drug (definitely related, probably related, possibly related, unlikely related, unrelated), date of administration of test medications and all concomitant medications, and medical treatment provided. A MedWatch Form 3500A will be used. The reports will include the appropriate HLMCC, USF IRB, USF IBC, FDA IND and NIH/OBA protocol reference numbers.

The Principal Investigator is responsible for evaluating all adverse events to determine whether criteria for "serious" and "unexpected" as defined above are present. All Serious Adverse Events regardless of cause will be entered into the H. Lee Moffitt Cancer Center & Research Institute research database (ONCORE) and will be reported to the HLMCC Protocol Monitoring Committee (PMC).

All SAE's will be reported to the following agencies within the timeframes stated (after the Principal Investigator's initial receipt of the information) and via the reporting methods indicated in the Table 6 below.

TABLE 6

Time frame for reporting SAEs

| EVENT | REGULATORY AGENCY | TIME FRAME (business days) | METHOD |
|---|---|---|---|
| All fatal and/or life-threatening events that might be due to administration of the test article | HLMCC PMC | 2 | ONCORE |
|  | USF IRB | 2 | IRB website |
|  | USF IBC | 2 | email |
|  | NIH/OBA | 7 | GeMCRIS |
|  | FDA | 7 | phone/fax + IND Safety Report |
| All other serious and/or unexpected adverse events that might be due to administration of the test article | HLMCC PMC | 5 | ONCORE |
|  | USF IRB | 5 | IRB website |
|  | USF IBC | 5 | email |
|  | NIH/OBA | 15 | GeMCRIS |
|  | FDA | 15 | IND Safety Report |

6.6. National Institutes of Health, Office of Biotechnology Activities, Recombinant DNA Advisory Committee In accordance with the Appendix M-I-C-4-b of the NHI Guidelines for Research Involving Recombinant DNA Molecules (NIH Guidelines), The Office of Biotechnology Activities, Recombinant DNA Advisory Committee will be notified of adverse events by using the GeMCRIS (Genetic Modification Clinical Research Information System) on-line adverse event reporting system.

Any serious adverse event that is fatal or life threatening, that is unexpected and is associated with the use of the gene transfer product must be reported to the NIH OBA as soon as possible, but no later than 7 calendar days after the Principal Investigator's initial receipt of the information.

Serious adverse events that are unexpected and associated with the use of the gene transfer product, but are not fatal or life threatening must be reported to the NIH OBA as soon as possible, but no later than 15 calendar days after the Principal Investigator's initial receipt of the information. (i.e., at the same time the event must be reported to the FDA).

6.7. Adverse Event Follow-Up

Patients will be monitored for adverse events throughout the treatment phase and for a minimum of 30 days after completion of the protocol treatment. Longer follow-up is required if necessary, to document recovery from treatment-related serious adverse events.

No further reporting of new adverse events is required after the initiation of any new treatment or more than 30 days following the last protocol treatment, unless a new SAE occurs that the study treatment was considered to have contributed. All SAE's will be reported for 100 days after the last protocol treatment.

7 Pharmaceutical/Cell Therapy Information

A list of the adverse events and potential risks associated with the investigational or commercial agents administered in this study can be found in Sections 4.3.1 and 4.3.2.

7.1. GM.CD40L (Vaccine)

7.1.1. Description of the GM.CD40L bystander cell

The continuous K562 cell line (ATCC #CCL-243) was established by Lozzio and Lozzio[54] from the pleural effusion of a 53-year old female with chronic myelogenous leukemia in terminal blast crisis. The cell population has been characterized as highly undifferentiated and of the granulocytic series[55]. Studies conducted by Anderson et al.[56] on the surface membrane properties led to the conclusion that the K562 was a human erythroleukemia line. The K562 cell line has attained widespread use as a highly sensitive in vitro target for the natural killer (NK) assay[57]. Cultures from ATCC stock have been shown to exhibit this sensitivity for assessing human NK activity.

Karyological studies on various K561 sublines have been classified into three groups (A, B, C) by Dimery et al[58]. The ATCC strain most closely resembles the B population. Occurrence of the Philadelphia chromosome, however, was of much lower frequency; none was detected in 15 metaphases examined. The stemline chromosome number is triploid with the 2S component occurring at 4.2%. Purified DNA from this line is available from ATCC (Catalog #45506 and 45507, 25 mg and 100 mg respectively).

The K562 cell line has undetectable expression of HLA class I and class II antigens both at rest and after incubation with IFN-$\gamma$[37].

K562 cells are grown in suspension cultures and are maintained at 37° C. in a 5% $CO_2$ humidified environment in Iscove's medium supplemented with 10% fetal calf serum (FCS), 50 U/mL penicillin-streptomycin, 2 mM L-glutamine, and 50 mM 2-mercaptoethanol (complete medium).

The cDNA for human CD40L was first excised from the pcDL-SRalphahCD40L cloning vector (ATCC #79814) using a BamHI restriction digest, and then inserted into the multiple cloning site of the expression vector pNGVL3 (gift of Gary J. Nabel, University of Michigan), which contains the gene for kanamycin resistance. Restriction enzyme digest analysis confirmed appropriate release of the isolated hCD40L cDNA. The correct reading frame was confirmed by in-line sequencing of the hCD40L gene in the pNGVL3 plasmid.

K562 cells were transfected with the pNGVL3hCD40L plasmid by electroporation. Briefly, K562 cells in log phase growth were harvested, washed twice with PBS, resuspended at $1\times10^7$ cells per mL, and transferred to electroporation cuvettes (BTX, Genetronics Inc., Model #640) on ice. Plasmid DNA (40 mcg) was added to the cell suspension and incubated on ice for 5 min. The mixture was then electroporated with 250 volts at a capacitance setting of 960 mF. The cuvettes were kept at room temperature for 5 min, then the transfected cells were diluted 1:20 in nonselective Iscove's complete medium and incubated for culture. Cells were sorted by flow cytometry three times for CD40L expression, followed by cloning by limiting dilution of the cell pool. The final positive clone was grown in culture and frozen for future use.

The singly transduced K562-CD40L cells described above was transfected with the pCEP4hGM-CSF construct (gift of Ivan Borrello, Johns Hopkins University) containing the hGM-CSF gene (505 bp) and the gene for Hygromycin B resistance. Briefly, the plasmid DNA was digested with BlnI and ClaI restriction enzymes overnight at 37° C. and run on a 1% Seakam agarose gel at 100 volts. The linearized band was cut from the gel and purified by the Freeze and Squeeze method. DMRIE-C Reagent (GIBCO, Life Technologies, Cat #10459-014) was used to deliver the linearized plasmid into the K562 and K562-CD40L cells. (This reagent is a 1:1 (M/M) liposome formulation of the cationic lipid DMRIE and cholesterol in membrane-filtered water. The positively charged and neutral lipids form liposomes that can complex with nucleic acids.) Hygromycin B (500 mg/mL) was added to the cultures after 48 hours and resulting colonies were transferred to 96-well tissue culture plates after 10 days. Subsequent clones were grown in 24-well tissue culture plates and tested for GM-CSF production by ELISA. Positive clones were identified, grown in culture, and frozen for future usage. A stable transfected clone was designated K562-GM-CSF-CD40L.

The K562-GM-CSF-CD40L clone used for generation of the Master Cell Bank (clone #1) has been named "GM.CD40L" and will be used and distributed under this name. Once the transfected cell line was established (March 2001), medium in which cells were propagated was converted to AIM-V serum-free medium (Life Technologies, GIBCO BRL, Catalog #12055-091). All subsequent cell passages were carried out in this medium (supplemented with hygromycin B).

7.1.2. General Characteristics of the Cell Line

The GM.CD40L cell line, like the K562 parent cell line from which it is derived, is an MHC-negative cell line that grows as a cell suspension culture. GM.CD40L was selected as a co-transfected clone that secretes human GM-CSF and expresses CD40L on its cell surface.

7.1.3. Generation of the Cell Banks

The Master Cell Bank (MCB) was generated by serial subculture and expansion of the original GM.CD40L clone until $4\times10^8$ cells were available for simultaneous harvest and cryopreservation. This created a uniform population of cells which was divided equally into 19 vials ($2\times10^7$ cells per vial) and stored in the vapor phase of liquid nitrogen.

The Manufacturer's Working Cell Bank (MWCB) was generated from two vials of the MCB. The MCB source cells (p8) were thawed on May 7, 2001, and expanded by serial subculture in AIM-V serum-free medium (Life Technologies, GIBCO BRL, Catalog #12055-091) containing Hygromycin B (500 mcg/mL) until May 15, 2001. At this point, the concentration of Hygromycin B was reduced to 250 mg/mL in order to help improve culture conditions and minimize loss of cell viability. On May 18, 2001, cells were removed from Hygromycin B-containing medium and returned to fresh AIM-V serum-free medium for 48 hours. On May 22, 2001, $19\times10^7$ cells (p13) were harvested and combined into one pool. Final cell viability of these harvested cells, as determined by trypan blue exclusion, was 83%. A fraction of the cells ($9.4 \times 10^8$) was dispensed into 48 individual vials ($2\times10^7$ cells per ampoule), and cryopreserved to form the MWCB. Another fraction of the cells ($4\times10^8$) was irradiated (15,000 rads) and then dispensed into 81 vials ($5\times10^6$ cells per vial), and cryopreserved to form the first lot (L001) of the biological product. All subsequent lots (L002, L003, L004, etc.) will be generated from single vials of the MWCB.

7.1.4. Storage of the Cell Banks

The MCB was frozen in 90% FCS with 10% dimethyl sulfoxide (DMSO); the MWCB was frozen in 70% Plasmalyte with 20% human serum albumin and 10% DMSO. Both the MCB and the MWCB are stored in the vapor phase of liquid nitrogen. All individual vials are clearly and legible labeled with the identity of the cells, the cell number, the freezing medium, and the date of preservation. This information, along with the location of individual vials, is documented and retained according to the Cell Therapy Facility SOP on Record Retention.

The MCB and MWCB are each stored in two separate liquid nitrogen vapor phase tanks within the production facility (Cell Therapy Facility, Room 464C, M2Gen Building, Moffitt Cancer Center). A minimum of two vials from each cell bank are stored in each freezer. Two archival samples of unused vials will be maintained under lock and key in the same location. All raw data and original case report forms generated from the characterization studies performed in the Cell Therapy Facility will be archived according to the Cell Therapy Facility SOP on Record Retention.

7.1.5. Cell Bank Qualfication and Characterization of Therapeutic Entity

Figure 3:
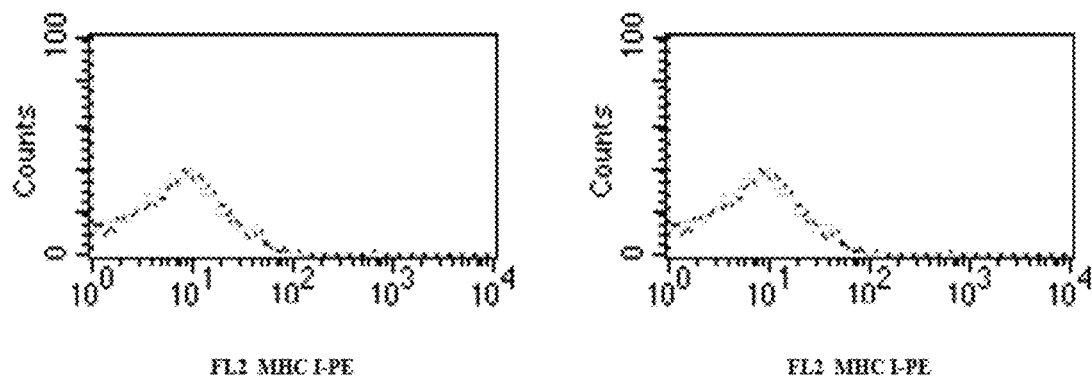
FIG. 3 shows side scatter and forward scatter plots for GM.CD40L cells.
Figure 4:
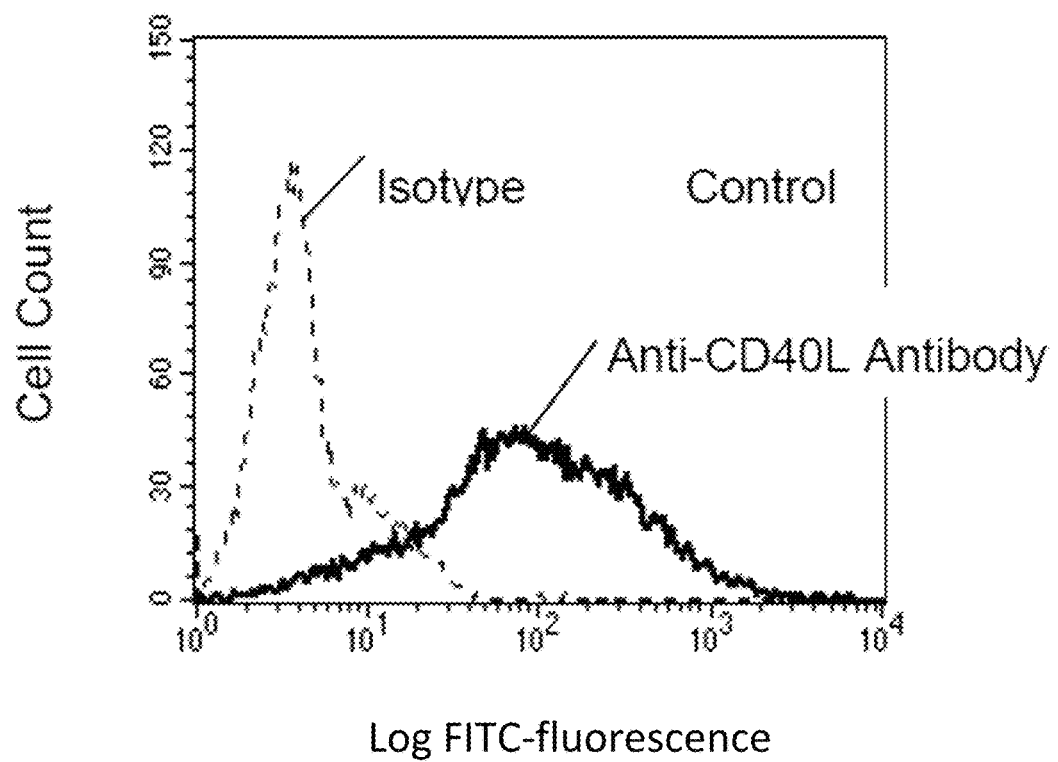
FIG. 4 shows quantification of cells expressing CD40L by flow cytometry using an anti-human CD40L antibody.
Figure 5:
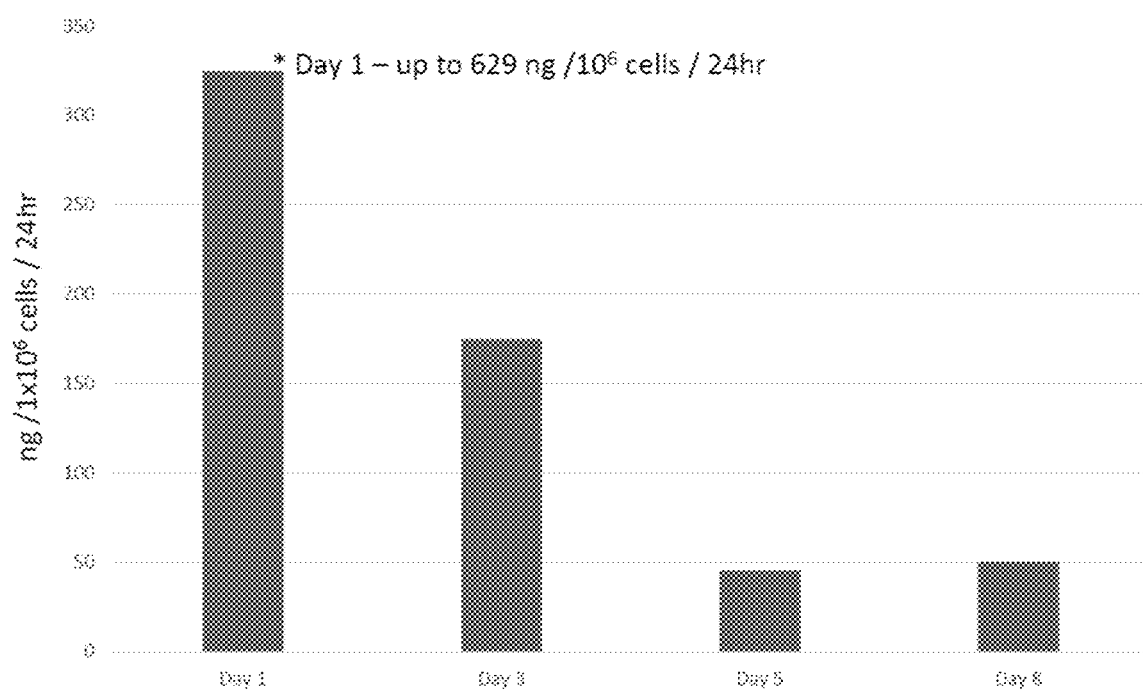
FIG. 5 shows ELISA results for GM-CSF production.
Figure 6:
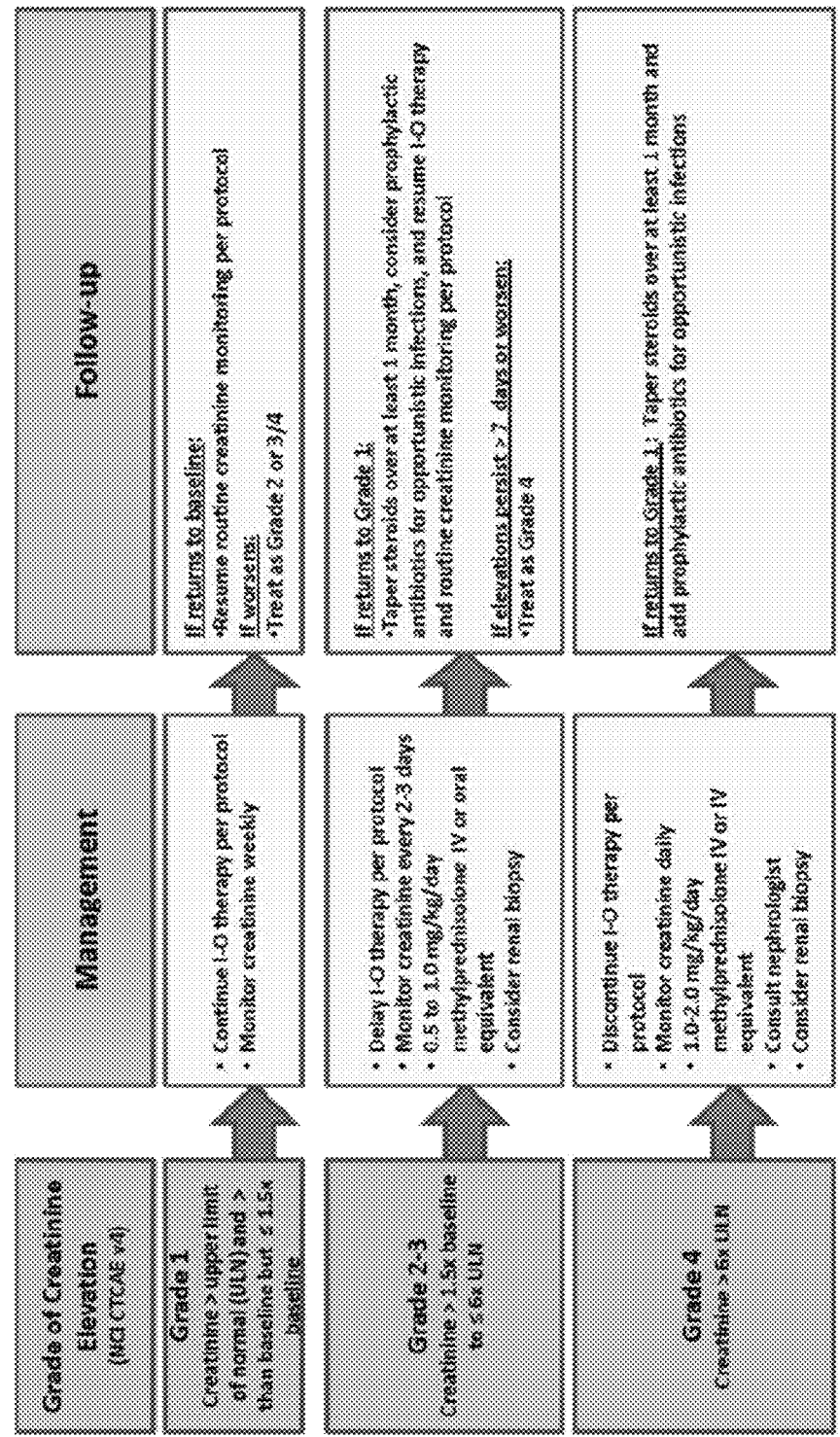
FIG. 6 shows a flow chart for a renal adverse even management algorithm.
Figure 7:
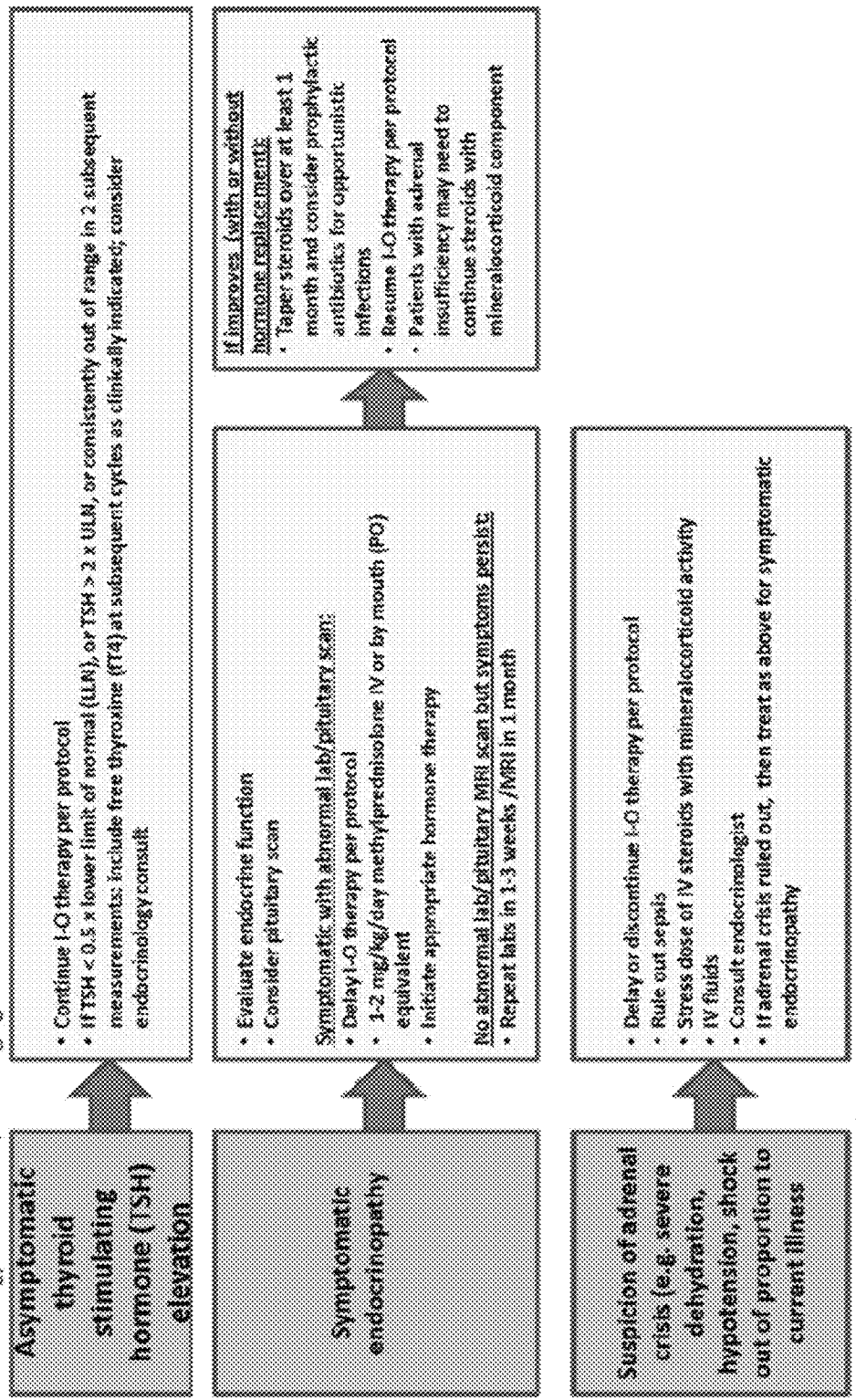
FIG. 7 shows a flow chart for a endocrinopathy management algorithm.
Figure 8:
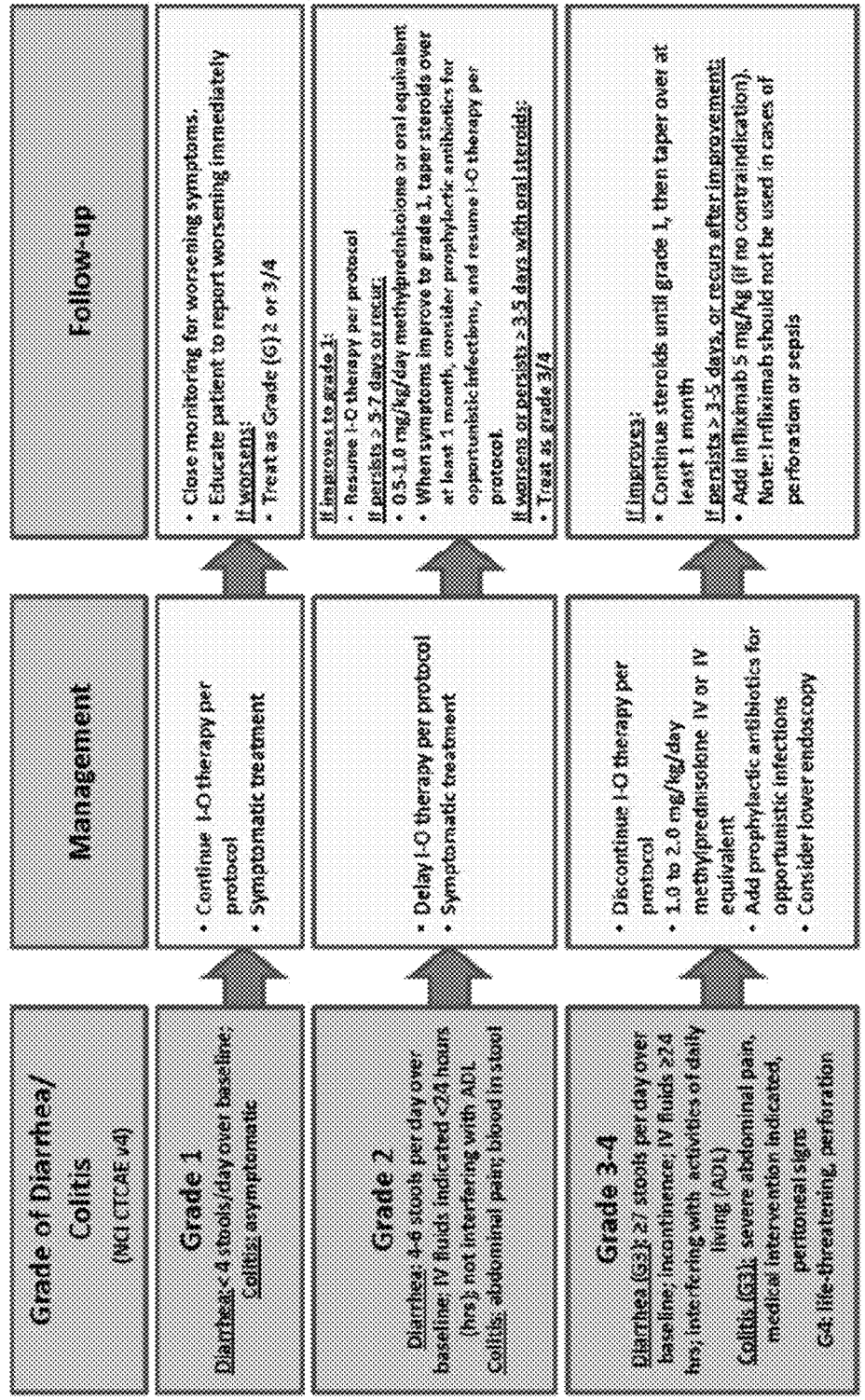
FIG. 8 shows a flow chart for a GI adverse even management algorithm.
Figure 9:
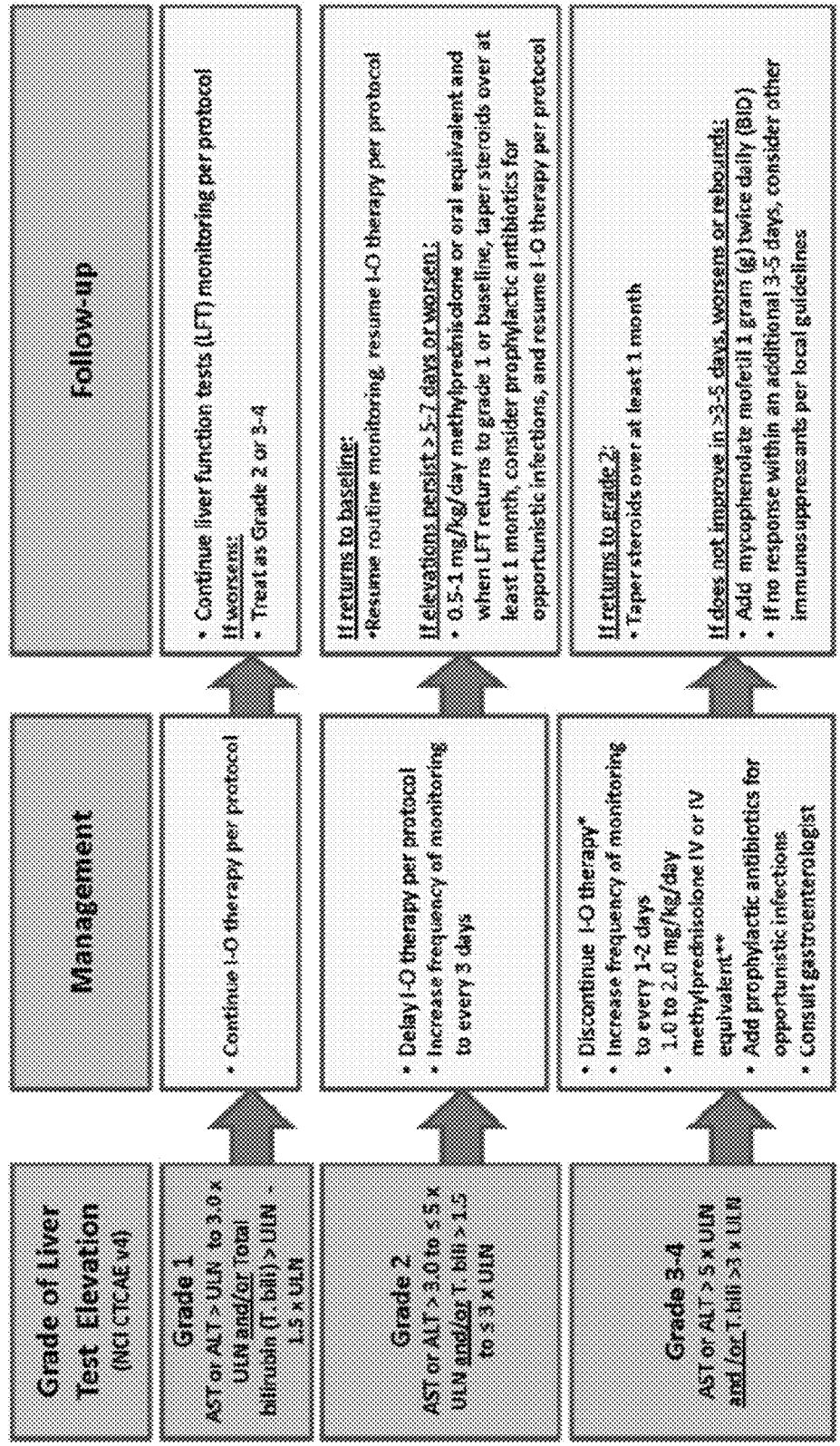
FIG. 9 shows a flow chart for a hepatic adverse even management algorithm.
Figure 10:
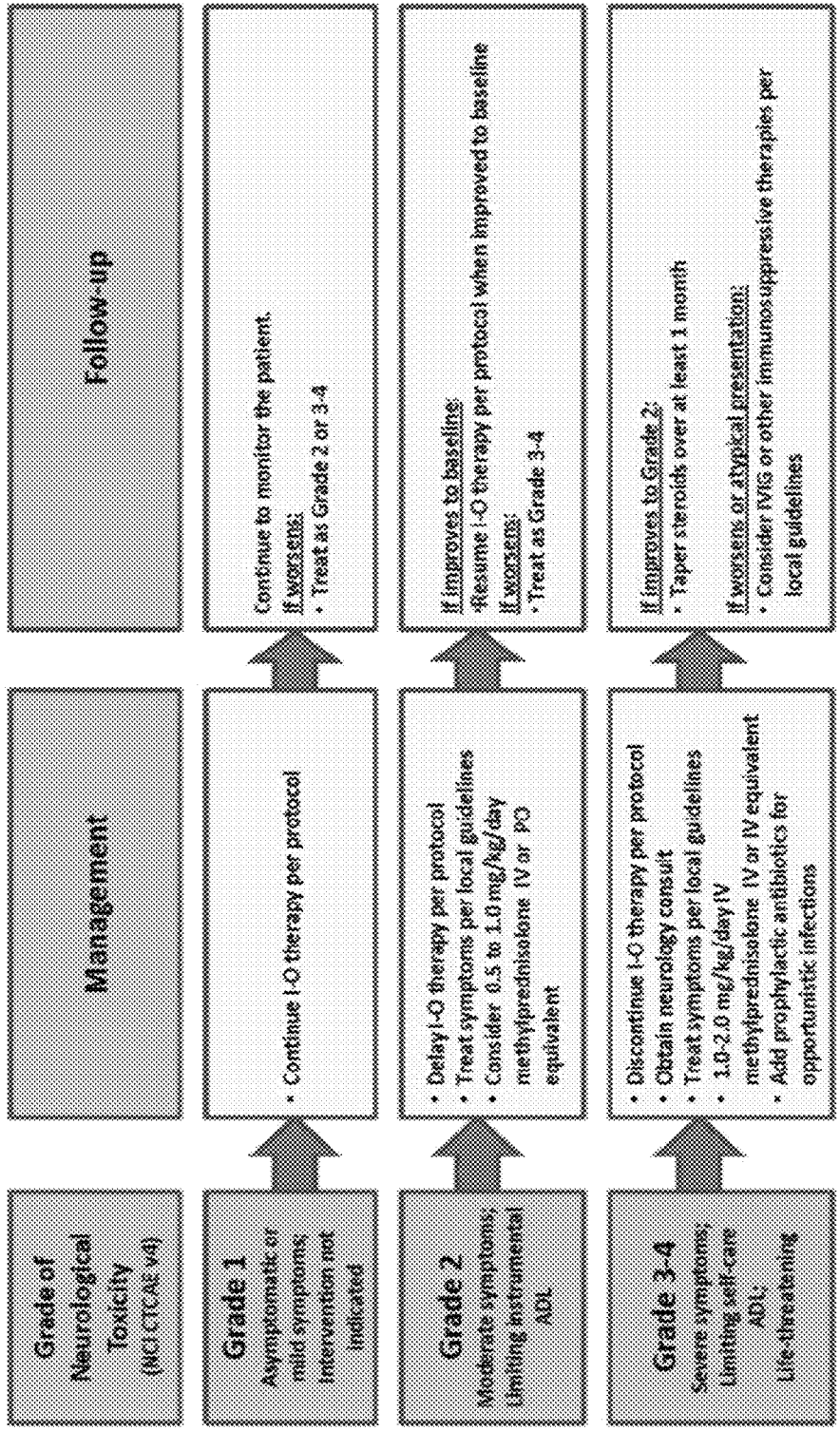
FIG. 10 shows a flow chart for a neurological adverse even management algorithm.
Figure 11:
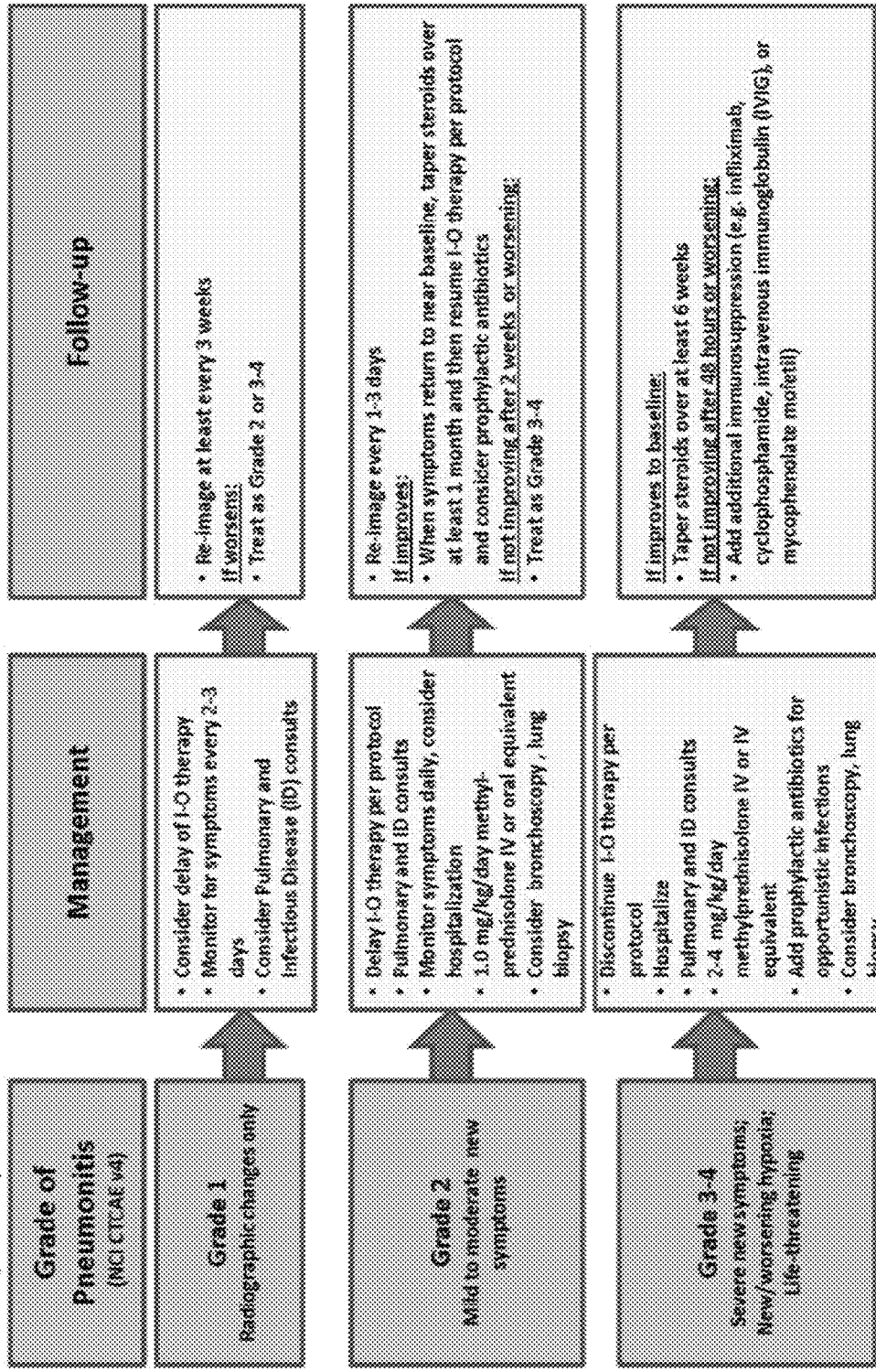
FIG. 11 shows a flow chart for a pulmonary adverse even management algorithm.
Figure 12:
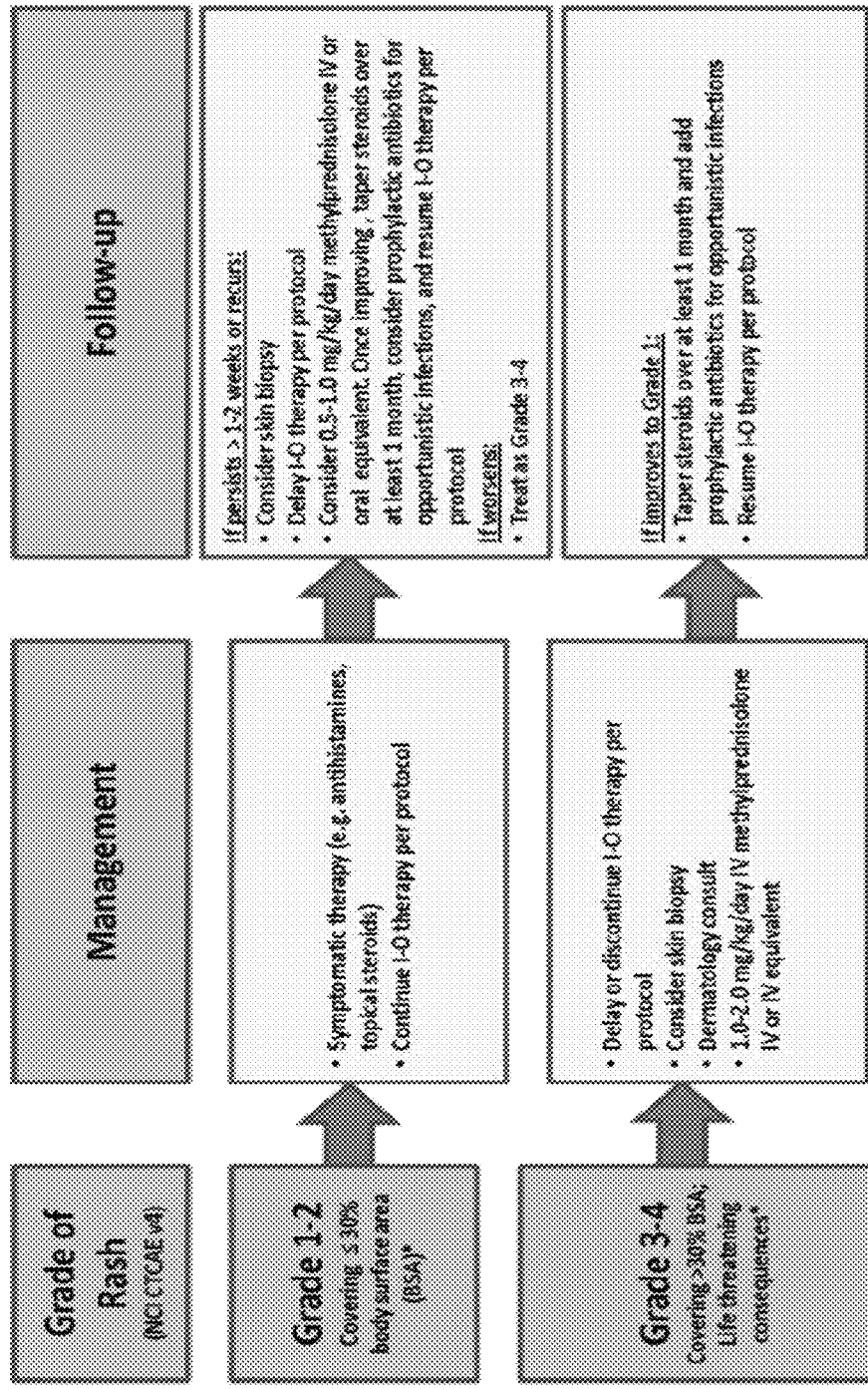
FIG. 12 shows a flow chart for a skin adverse even management algorithm.

The Master Cell Bank. Testing of the MCB was done on cell cultures derived from vials of the MCB. Testing to qualify the MCB includes 1) testing to demonstrate freedom from adventitious agents and 2) identity testing. All testing for adventitious agents (including tests for bacteria, fungi, *mycoplasmas*, and viruses) has been negative. Testing for adventitious viruses (including routine in vivo and cell culture inoculation tests) has also been negative. Extensive identity testing of the MCB has been completed. This includes cytogenetic (karyology) and isoenzyme analysis (carried out by Applied Genetics Laboratories, Inc., Melbourne, Fla.), as well as tests needed to establish all significant properties of the cells (including negative MHC cell surface expression, positive CD40L cell surface expression, and GM-CSF secretion into the local microenvironment) and the stability of these properties throughout the manufacturing process (including irradiation and a freeze/thaw cycle).

a. Absence of MHC expression by the GM.CD40L cell line was confirmed by flow cytometry using pan-antibodies (PE-conjugated murine anti-human HLA-A,B,C [MHC class 1] antibody, Pharmingen Catalog #555553, Clone G46-2.6; FITC-conjugated murine anti-human HLA-DR, DP,DQ [MHC class II] antibody, Pharmingen Catalog #555558, Clone TY39). Cells were gated on side-scatter and forward scatter, and 10,000 viable cells were collected accordingly. Analysis was performed on a FACScan (Becton Dickinson) using Lysis II software (FIG. 3).

b. CD40L expression was quantified by flow cytometry using the mouse FITC-conjugated anti-human CD40L (CD154) monoclonal antibody (Catalog #353-040, Immunology Research Products, Ancell Corp., Bayport, Minn.). Cells were gated on side-scatter and forward scatter, and 10,000 viable cells were collected accordingly. Analysis was performed on a FACScan (Becton Dickinson) using Lysis II software. The fraction of the cell population expressing CD40L, as well as the intensity of CD40L expression, can be used as an indication of gene maintenance within the cell line (FIG. 4).

c. GM-CSF expression was quantified by ELISA. Briefly, $1\times10^6$ cells were grown in 5 mL of AIM-V serum-free medium, and the supernatant was collected 24 hr later. Human GM-CSF was quantified with enzyme-linked immunosorbent assay (ELISA) kits (Catalog #DGM00, R&D Systems, Minneapolis, Minn.) as per the manufacturer's instructions. All samples were tested in duplicate. The level of GM-CSF produced by $1\times10^6$ cells over 24 hours (300-700 ng/$1\times10^6$ cells/24 hrs) can be used as an indication of cell purity over time.

d. Cell viability and stable expression of GM-CSF and CD40L after irradiation and freezing was determined by ELISA and flow cytometry (as described above). Absence of MHC expression was also confirmed. Briefly, GM.CD40L cells were suspended at a concentration of $3.70\times10^6$ cells/mL of partial freezing medium (7 parts Plasmalyte; 2 parts human serum albumin; no DMSO). Cell viability was determined by Trypan Blue exclusion during counting. Cells were irradiated with 15,000 rads from a $^{137}$Cs source discharging 800 rad/min. After irradiation, DMSO was added to the cell suspension to complete the freezing medium (final concentration of DMSO, 10%), and cells were frozen in liquid nitrogen ($5\times10^6$ cells in 1.5 mL of medium per vial). Cells were thawed after one week and evenly distributed in flat-bottomed 24-well tissue culture plates ($10^6$ cells in 2 mL per well) and maintained at 37° C. in a 5% $CO_2$ humidified environment. Cells from 2 wells were collected on Days 0, 3, 5, and 7. Cells from one well were analyzed by flow cytometry for CD40L and MHC expression. Cells from the other well were washed and resuspended in 5 mL of fresh medium; the supernatant was collected after 24 hrs, frozen at −20° C., and analyzed by ELISA for GM-CSF production at the end of the 7 days. The ELISA was carried out on thawed samples as per the manufacturer's instructions (Catalog #DGM00, R&D Systems, Minneapolis, Minn.) (FIG. 5).

7.1.6. The Manufacturer's Working Cell Bank

The MWCB, derived from the MCB and propagated for a maximum of 150 passages in tissue culture, only needs to be spot checked for contaminants that may be introduced from the culture medium. Tests, including testing for sterility, screening for *mycoplasma*, in vitro and in vivo testing for viral contamination, and checking for cell line cross-contamination, have been completed and have shown the MWCB to be free of contaminants.

7.1.7. Stability of the GM.CD40L Cell Line

Stable expression of GM-CSF and CD40L will be determined by ELISA and flow cytometry on cells retrieved from liquid nitrogen at the completion of culturing. The fraction of the cell population expressing CD40L, the intensity of CD40L expression, as well as the level of GM-CSF produced by $1 \times 10^6$ cells over 24 hours, will be used as a measure of cell purity. Absence of MHC expression will also be confirmed by flow cytometry at this time.

7.2. Description of the Human Lung Adenocarcinoma Allogeneic Cell Lines

7.2.1 History of the Cell Lines

The second component of vaccines A and B will consist of a mixture of two human NSCLC cell lines that will serve as the source of lung tumor antigens. These cell lines, NCI-H1944 and NCI-H2122, combined express the following tumor antigens commonly over-expressed in NSCLC: Her-2/neu, CEA, GD-2, WT-1, and MAGE-1, -2 and -3[46]. We have obtained both of these cell lines from the ATCC.

7.2.2 Generation, Storage, Characterization, Production, and Quality Control Testing H1944 and H2122 have been successfully adapted to propagation in serum free medium and the master cell banks, manufacturer working cell banks, and lots have been produced.

The Master Cell Bank for cell lines NCI-H2122 and NCI-H1944 were sent for testing to AppTec where the following tests were performed:

Cell Culture Identification Characterization
Karyology
Bacterial and Fungal Sterility Test
Bacteriostatic/Fungistatic Activity
*Mycoplasma*, cultivable and non cultivable
Detection of Avdentitious Virus (In Vivo)
Detection of Adventitious virus (In Vitro)
Thin Section Electron Microscopy: Cell Morphology and virus detection/Tabulation
Detection of Reverse Transcriptase Activity
Detection of HIV II
Detection of HTLV I/II
Detection of Human Herpesvirus 6 (HHV-6)
Detection of Human Herpesvirus 7 (HHV-7)
Detection of Human Herpesvirus 8 (HHV-8)
Presence of Bovine Viruses
Presence of Porcine Viruses All final test reports reveal human cell lines with no viral, bacterial or fungal contamination.

The Master Cell Banks were also sent to Tampa General Hospital where the following tests were performed with methods validated for the specific matrix:

Detection of Epstein Barr Virus (EBV)
Detection of Cytomegalovirus (CMV)
Detection of Hepatitis C Virus (HCV)
Detection of Hepatitis B Virus (HBV)
Detection of HIV I
Detection of Human Parvovirus B19 (HPB19)

The final test report reveals no detectable nucleic acids from the above-mentioned viruses.

7.3. Production Cultures and Product Testing

7.3.1. Cell Culture Media

Accurate records of the composition and source of the cell culture medium are available. These records and all product information sheets (including certificates of analysis) will be archived for a period of not less than ten years at the Testing Facility (MDC 1046) in a binder labeled Protocol 01-003-A. Since animal serum may produce allergic responses in human subjects, X-VIVO 15 serum-free medium (Catalog #04-418Ω, Lonza Walkersville, Inc., Walkersville, Md.) has been used for the propagation of production cell cultures. Penicillin or other beta-lactam antibiotics have not been used in production cell cultures. Gentamicin sulfate is present at 50 micrograms/mL,) GM.CD40L, like the parental K562 cell line, and H2122 grow in suspension cultures, therefore porcine trypsin is not used in passaging cells. The H1944 cell line can become adherent in the absence of serum. Adherent cells are recovered using TrypLE™ Select (Life Technologies, Grand Island, N.Y.). TrypLE™ Select is free of animal origin.

72.2 Management of Cell Cultures

Lot-to-lot characterization of the cell lines and routine monitoring for adventitious agents will be part of the quality control of the biological product. This will include testing of production cell cultures and unprocessed and processed cell culture fluids. Quality control testing will be performed on each bulk lot. Testing for bacterial and fungal sterility will be performed on the unprocessed bulk lot, the final bulk lot, and the final product. The unprocessed bulk is the pooled harvests of cell culture fluids that constitute a homogeneous mixture for manufacture into a unique lot of product. Routine testing for *mycoplasma* will be performed on every lot using unprocessed bulk fluids. Testing for adventitious agents will be performed prior to further processing such as spinning, washing, and suspension of cells. The final bulk is the concentrated, washed cell suspension prepared for irradiation, distribution into separate vials or aliquots, and final freezing for vaccine purposes. The final bulk will be subjected to a variety of lot release tests which will include sterility testing. The final product—cells that have been irradiated, frozen, and thawed—will be tested for sterility and endotoxin. Viability and enumeration (by Trypan blue) of the final product will be assessed for all cell lines to confirm irradiation of the cell lines. Additionally, all lots of GM.CD40L will require testing to confirm negative MHC cell surface expression (flow cytometry), positive CD40L cell surface expression (also by flow cytometry), and GM-CSF secretion into the local microenvironment (by ELISA).

72.3 Quality Control Testing

7.3.3.1 Tests for the Presence of Bacteria and Fungi

The sterility of each lot of vaccine product was demonstrated by performance of the required tests described in 21 CFR 610.12. Specimens from the MCB were submitted to Charles River Laboratories (Malvern, Pa.) for testing. Sterility testing of lots is performed by the Moffitt Cancer Center Clinical Laboratory.

7.3.3.2 Tests for the Presence of *Mycoplasma*

Tests for the presence of *mycoplasma* contamination of cultures were carried out by Focus so Technologies (Cypress, Calif.). Tests include #51002 (*Mycoplasma* culture, fastedious pathogens), #41333 (*Mycoplasma* speciation PCR, cell culture screen), and #46300 (*Mycoplasma pneumoniae* DNA, PCR assay). The MCB has been tested according to the "1993 Points to Consider *Mycoplasma* Assay" by Charles River Laboratories (Malvern, Pa.). *Mycoplasma* testing on each lot is performed using the PCR-based Venor™GeM *Mycoplasma* Detection Kit (Catalog #MP0025, Sigma-Aldrich, St. Louis, Mo.).

7.3.3.3 Tests for the Presence of Viruses a. Routine Tests for Adventitious Viruses. Specimens from the MCB were submitted to Charles River Laboratories (Malvem, Pa.) for testing. Cell cultures were observed at the end of the production period for viral cytopathic effects and tested for hemadsorbing viruses. At the time of production of each unprocessed bulk pool, a. proportion of the pool was inoculated into cell cultures (MRC-5, a human diploid lung cell line; Vero, an African green monkey kidney cell line; HeLa, a human epithelioid carcinoma cell line), embryonated hen eggs, and suckling mice. Samples were also collected for bovine and porcine virus assays. All results have been negative.

b. Selected Tests for Adventitious Viruses. Specimens from the MCB were submitted to Focus Technologies (Cypress, Calif.) for testing for the following human virus pathogens: Epstein-Barr virus (EBV), cytomegalovirus (CMV), hepatitis B and C (HBV, HCB), HIV-1 and -2, and HHV-6 using appropriate in vitro PCR techniques. Specimens were sent to BioReliance (Rockville, Md.) for testing of B19 virus. All results have been negative.

c. Tests for Retroviruses. Specimens from the MCB were submitted to Charles River Laboratories (Malvern, Pa.) and BioReliance (Rockville, Md.) for examination for the presence of retroviruses utilizing transmission electron microscopy and reverse transcriptase assays. All results have been negative.

7.4 Summary of Vaccine Preparation

GM.CD40L cell line is maintained in a Manufacturer's Working Cell Bank (MWCB). Individual lots of GM.CD40L are created by thawing an MWCB vial, containing $10^7$ cells, and placing in X-VIVO-15 serum free culture medium in a T75 tissue culture flask at a concentration of $0.2$-$0.4 \times 10^6$ cells/ml. Cells are grown with once or twice per week medium supplementation, based on visual observation of cell density and expenditure of growth medium. As the cell population increases, cells are split into more and larger tissue culture flasks, until approximately $1 \times 10^9$ cells are available. The cell suspension is irradiated at 150 Gy using the X-RAD 160 X-Ray Irradiator (Precision X-Ray, Inc., North Branford, Conn.). The cell suspension is combined at a 1:1 ratio with freeze medium (Plasmalyte A, 10% human serum albumin, 20% DMSO; final DMSO concentration is 10%), at 1.5 ml per vial. A minimum of 10% of the vials are held aside and are tested for bacteria and fungi using microbial culture and for endotoxin by limulus amoebocyte lysate assay. Viabilities and cell counts are performed to confirm irradiation of the cell line. Testing is also performed to confirm expression of CD40L and the absence of MHC I and MHC II (by flow cytometry) and secretion of GM-CSF (by ELISA). The remaining vials are maintained in the gas phase over liquid nitrogen until required for use.

H2122 cell line is maintained in a MWCB. Individual lots are produced following methods used for the GM.CD40L cell line and cultured until approximately $5 \times 10^8$ cells are available. Cells are irradiated, frozen, and tested to confirm sterility and irradiation as described for the GM.CD40L cell line.

H1944 cell line is maintained in a MWCB. Individual lots are produced following methods used for the GM.CD40L cell line and cultured until approximately $5 \times 10^8$ cells are available. Clumping and adherence can occur in H1944 cells cultured in the absence of serum. In this case, medium is be collected from flasks, TrypLE™ Select is added to flasks for the recommended time frame, and cells are collected, the TrypLE™ Select is diluted and cells are centrifuged. If cells are clumping, pelleted cells are suspended in TrypLE™ Select and then diluted and the centrifuged. Cells are irradiated, frozen and tested to confirm sterility and irradiation as described for the GM.CD40L cell line.

7.5. Nivolumab (Anti-PD-1) Product Information

Nivolumab is a fully human monoclonal immunoglobulin G4 (IgG4) antibody (HuMAb) that targets the programmed death-1 (PD-1, cell differentiation 279 [CD279]) cell surface membrane receptor. Nivolumab is a soluble protein consisting of 4 polypeptide chains, 2 identical heavy chains and 2 identical light chains. The physical and chemical properties of nivolumab drug substance are: MW 143,599 Da; Clear to opalescent, colorless to pale yellow liquid. May contain particles; with solution pH 5.5-6.5.

7.5.1. Drug Ordering and Accountability:

BMS is supplying study drug, information in this section may include how to order study drug from BMS or from the Investigator pharmacy. Or this information may be included in a pharmacy manual.

Please see Appendix 1 for information on provisions for ordering study drug from BMS.

It is possible that sites may have more than one clinical study on the same drug ongoing at the same time. It is imperative that only drug product designated for this protocol be used for this study The investigator is responsible for ensuring that the investigational product is stored under the appropriate environmental conditions (temperature, light, and humidity)

If concerns regarding the quality or appearance of the investigational product arise, do not dispense the investigational product, and contact BMS immediately. If commercial investigational product is used, it should be stored in accordance with the appropriate local labeling If the study drug(s) are to be destroyed on site, it is the investigator's responsibility to ensure that arrangements have been made for disposal, and that procedures for proper disposal have been established according to applicable regulations, guidelines, and institutional procedures 7.5.2. Product Description and Dosage Form Please provide information on the product as shown in the sample table below.

PRODUCT INFORMATION TABLE: Please also see Drug Information Appendix 1

| Product Descripton: Other names = MDX-1106 ONO-4538, anti-PD-1 | | | | | |
| --- | --- | --- | --- | --- | --- |
| Product Description and Dosage Form | Potency | Primary Packaging (Volume)/ Label Type | Secondary Packaging (Qty)/Label Type | Appearance | Storage: Conditions per label) |
| Nivolumab BMS-936558-01)* Injection drug product is a | 100 mg/Vial (10 mg/mL). | Carton of 5 or 10 vials | 10-cc Type 1 flint glass vials stoppered with butyl stoppers and sealed | Clear to opalescent, colorless to pale yellow liquid. May contain | BMS-936558-01 Injection must be stored at 2 to 8 degrees C. (36 to 46 degrees F.) and |

-continued

| Product Description and Dosage Form | Potency | Primary Packaging (Volume)/ Label Type | Secondary Packaging (Qty)/Label Type | Appearance | Storage: Conditions per label) |
|---|---|---|---|---|---|
| sterile, non-pyrogenic, single-use, isotonic aqueous solution formulated at 10 mg/mL | | | with aluminum seals | particles | protected from light and freezing |

*Nivolumab may be labeled as BMS-936558-01 Solution for Injection

If stored in a glass front refrigerator, vials should be stored in the carton. Recommended safety measures for preparation and handling of nivolumab include laboratory coats and gloves.

For additional details on prepared drug storage and use time of nivolumab under room temperature/light and refrigeration, please refer to the BMS-936558 (nivolumab) Investigator Brochure section for "Recommended Storage and Use Conditions".

7.5.3. Handling and Dispensing

The investigator should ensure that the study drug is stored in accordance with the environmental conditions (temperature, light, and humidity) as per product information and the Investigator Brochure and per local regulations. It is the responsibility of the investigator to ensure that investigational product is only dispensed to study subjects. The investigational product must be dispensed only from official study sites by authorized personnel according to local regulations. If concerns regarding the quality or appearance of the study drug arise, the study drug should not be dispensed and contact BMS immediately.

Please refer to the current version of the Investigator Brochure and/or shipment reference sheets for additional information on storage, handling, dispensing, and infusion information for nivolumab.

7.5.4. Destruction

Sponsor/Investigator drug destruction is allowed provided the following minimal standards are met:
1. On-site disposal practices must not expose humans to risks from the drug.
2. On-site disposal practices and procedures are in agreement with applicable laws and regulations, including any special requirements for controlled or hazardous substances.
3. Witten procedures for on-site disposal are available and followed. The procedures must be filed with the Sponsor SOPs and a copy provided to BMS upon request.
4. Records are maintained that allow for traceability of each container, including the date disposed of, quantity disposed, and identification of the person disposing the containers. The method of disposal, ie, incinerator, licensed sanitary landfill, or licensed waste disposal vendor must be documented.
5. Accountability and disposal records are complete, up-to-date, and available for BMS to review throughout the clinical trial period as per the study agreement.
6. If conditions for destruction cannot be met, please contact BMS.
7. It is the Sponsor Investigator's responsibility to arrange for disposal of all empty containers, provided that procedures for proper disposal have been established according to applicable federal, state, local, and institutional guidelines and procedures, and provided that appropriate records of disposal are kept.

8 Measurement of Effect 8.1. Antitumor Effect—Solid Tumors

Response and progression will be evaluated in this study using RECIST v 1.1 criteria[59,60].

For the purposes of this study, patients will be re-evaluated for response every 6 weeks (see study calendar). In addition to a baseline scan, confirmatory scans will also be obtained 4 weeks following initial documentation of objective response.

8.1.1. Definitions

Evaluable for toxicity. All patients will be evaluable for toxicity from the time of their first treatment with either nivolumab or the GM.CD40L vaccine.

Evaluable for objective response. Only those patients who have measurable disease present at baseline, have received at least one dose of nivolumab vaccine, where appropriate, and have had their disease re-evaluated will be considered evaluable for response. These patients will have their response classified according to the definitions stated below. Note: Patients who exhibit objective disease progression prior to the end of cycle 1 will also be considered evaluable.

Evaluable Non-Target Disease Response. Patients who have lesions present at baseline that are evaluable but do not meet the definitions of measurable disease, have received at least one dose of nivolumab vaccine, where appropriate, and have had their disease re-evaluated will be considered evaluable for non-target disease. The response assessment is based on the presence, absence, or unequivocal progression of the lesions.

8.1.2. Definitions of Measurable/Non-Measurable Lesions

All measurable and non-measurable lesions should be assessed at Screening and at the defined tumor assessment time points. Additional assessments may be performed, as clinically indicated for suspicion of progression. The Investigator will base response to treatment using the RECIST v1.1.

Measurable Lesions. Target lesions that can be measured accurately in at least one dimension (longest diameter to be recorded) as ≥20 mm with conventional techniques, or as ≥10 mm with spiral (helical) computed tomography (CT) scan or two (2) times the reconstruction interval (RI) when using spiral (helical) or multidetector CT, but not less than 10 mm. Note: Tumor lesions that are situated in a previously irradiated area might or might not be considered measurable. If the investigator thinks it appropriate to include them, only lesions that have clearly shown disease progression since prior irradiation will be considered or allowed.

Malignant lymph nodes. To be considered pathologically enlarged and measurable, a lymph node must be >15 mm in short axis when assessed by CT scan (CT scan slice thickness recommended to be no greater than 5 mm). At baseline and in follow-up, only the short axis will be measured and followed.

Non-Measurable Lesions. Non-target lesions not classified as measurable lesions (longest diameter <20 mm with conventional techniques or <10 mm with spiral CT scan) and truly nonmeasurable lesions. These include bone lesions, effusions, and leptomeningeal disease. Any measurable lesions that were not classified as target lesions will be classified as nontarget lesions.

All measurements should be taken and recorded in metric notation using a ruler or calipers. All baseline evaluations should be performed as closely as possible to the beginning of treatment and never more than 4 weeks before the beginning of the treatment.

The same method of assessment and the same technique should be used to characterize each identified and reported lesion at baseline and during follow-up. Imaging-based evaluation is preferred to evaluation by clinical examination unless the lesion(s) being followed cannot be imaged but are assessable by clinical exam.

Clinical lesions: Clinical lesions will only be considered measurable when they are superficial (e.g., skin nodules and palpable lymph nodes) and ≥10 mm diameter as assessed using calipers (e.g., skin nodules). In the case of skin lesions, documentation by color photography, including a ruler to estimate the size of the lesion, is recommended.
  Chest x-ray: Lesions on chest x-ray are acceptable as measurable lesions when they are clearly defined and surrounded by aerated lung. However, CT is preferable.
  Conventional CT and MRI: This guideline has defined measurability of lesions on CT scan based on the assumption that CT slice thickness is 5 mm or less. If CT scans have slice thickness greater than 5 mm, the minimum size for a measurable lesion should be twice the slice thickness. MRI is also acceptable in certain situations (e.g., for body scans). Use of MRI remains a complex issue. MRI has excellent contrast, spatial, and temporal resolution; however, there are many image acquisition variables involved in MRI that greatly impact image quality, lesion conspicuity, and measurement. Furthermore, the availability of MRI is variable globally. As with CT, if an MRI is performed, the technical specifications of the scanning sequences used should be optimized for the evaluation of the type and site of disease. Furthermore, as with CT, the modality used at follow-up should be the same as was used at baseline and the lesions should be measured/assessed on the same pulse sequence. It is beyond the scope of the RECIST guidelines to prescribe specific MRI pulse sequence parameters for all scanners, body parts, and diseases. Ideally, the same type of scanner should be used and the image acquisition protocol should be followed as closely as possible to prior scans. Body scans should be performed with breath-hold scanning techniques, if possible.

8.1.3. Definitions of Target/Non-Target Lesions

Target lesions. All measurable lesions up to a maximum of 2 lesions per organ and 5 lesions in total, representative of all involved organs, should be identified as target lesions and recorded and measured at baseline. Target lesions should be selected on the basis of their size (lesions with the longest diameter), be representative of all involved organs, but in addition should be those that lend themselves to reproducible repeated measurements. It may be the case that, on occasion, the largest lesion does not lend itself to reproducible measurement in which circumstance the next largest lesion which can be measured reproducibly should be selected. A sum of the diameters (longest for non-nodal lesions, short axis for nodal lesions) for all target lesions will be calculated and reported as the baseline sum diameters. If lymph nodes are to be included in the sum, then only the short axis is added into the sum. The baseline sum diameters will be used as reference to further characterize any objective tumor regression in the measurable dimension of the disease.

Non-target lesions. All other lesions (or disease sites) including any measurable lesions over the 5 target lesions, should be identified as non-target lesions and should also be recorded at baseline.

Measurements of these lesions are not required, but the presence, absence, or in rare cases unequivocal progression of each should be noted throughout follow-up.

8.1.5. Definition of Target Lesion Response

Complete Response (CR): Disappearance of all target lesions. Any pathological lymph nodes (whether target or non-target) must have reduction in short axis to <10 mm.
  Partial Response (PR): At least a 30% decrease in the sum of the diameters of target lesions, taking as reference the baseline sum diameters.
  Progressive Disease (PD): At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progressions).
  Stable Disease (SD): Neither sufficient shrinkage to qualify for PR nor sufficient increase to qualify for PD, taking as reference the smallest sum diameters while on study.

8.1.6. Definition of Non-Index Lesion Response

Complete Response (CR): Disappearance of all non-target lesions and normalization of tumor marker level. All lymph nodes must be non-pathological in size (<10 mm short axis). Note: If tumor markers are initially above the upper normal limit, they must normalize for a patient to be considered in complete clinical response.
  Non-CR/Non-PD: Persistence of one or more non-target lesion(s) and/or maintenance of tumor marker level above the normal limits.
  Progressive Disease (PD): Appearance of one or more new lesions and/or unequivocal progression of existing non-target lesions. Unequivocal progression should not normally trump target lesion status. It must be representative of overall disease status change, not a single lesion increase.
  Although a clear progression of "non-target" lesions only is exceptional, the opinion of the treating physician should prevail in such circumstances, and the progression status should be confirmed at a later time by the review panel (or Principal Investigator).

Note:

Impact of New Lesions on RECIST v1.1

New lesions alone do not qualify as progressive disease unless deemed to be clinically significant by the investigator Therefore, new non-measurable lesions alone will not discontinue any subject from the study.

8.1.7. Definition of Overall Response Using RECIST v1.1 Will be Based on the Following Criteria The best overall response is the best response recorded from the start of the treatment until disease progression/recurrence (taking as reference for progressive disease the smallest measurements recorded since the treatment started). The patient's best response assignment will depend on the achievement of both measurement and confirmation criteria.

TABLE 7

For Patients with Measurable Disease (i.e., Target Disease)

| Target Lesions | Non-Target Lesions | New Lesions | Overall Response | Best Overall Response when Confirmation is Required* |
|---|---|---|---|---|
| CR | CR | No | CR | >4 wks. Confirmation** |
| CR | Non-CR/Non-PD | No | PR | >4 wks. |
| CR | Not evaluated | No | PR | Confirmation** |
| PR | Non-CR/Non-PD/ not evaluated | No | PR | |
| SD | Non-CR/Non-PD/ not evaluated | No | SD | documented at least once >4 wks. from baseline** |
| PD | Any | Yes or No | PD | no prior SD, PR or CR |
| Any | PD*** | Yes or No | PD | |
| Any | Any | Yes | PD | |

*See RECIST 1.1 manuscript for further details on what is evidence of a new lesion.
**Only for non-randomized trials with response as primary endpoint.
***In exceptional circumstances, unequivocal progression in non-target lesions may be accepted as disease progression.
Note:
Patients with a global deterioration of health status requiring discontinuation of treatment without objective evidence of disease progression at that time should be reported as "symptomatic deterioration." Every effort should be made to document the objective progression even after discontinuation of treatment.

TABLE 8

For Patients with Non-Measurable Disease (i.e., Non-Target Disease)

| Non-Target Lesions | New Lesions | Overall Response |
|---|---|---|
| CR | No | CR |
| Non-CR/non-PD | No | Non-CR/non-PD* |
| Not all evaluated | No | not evaluated |
| Unequivocal PD | Yes or No | PD |
| Any | Yes | PD |

*'Non-CR/non-PD' is preferred over 'stable disease' for non-target disease since SD is increasingly used as an endpoint for assessment of efficacy in some trials so to assign this category when no lesions can be measured is not advised

8.1.8. Duration of Response

Duration of overall response: The duration of overall response is measured from the time measurement criteria are met for CR or PR (whichever is first recorded) until the first date that recurrent or progressive disease is objectively documented (taking as reference for progressive disease the smallest measurements recorded since the treatment started including the baseline measurements). A patient is considered "censored" if the patient is lost follow-up or no-recurrence or progression-free at the end of study.

The duration of overall CR is measured from the time measurement criteria are first met for CR until the first date that progressive disease is objectively documented.

Duration of stable disease: Stable disease is measured from the start of the treatment until the criteria for progression are met, taking as reference the smallest measurements recorded since the treatment started, including the baseline measurements.

Overall survival (OS): determined from the start of treatment to the time of death due to any cause. Patient is considered "censored" if the patient is lost follow-up or alive at the end of study.

Progression-free survival (PFS): defined as the duration of time from start of treatment to time of progression or death, whichever occurs first. Patient is considered "censored" if the patient is lost follow-up or progression-free at the end of study.

Objective response rate (ORR): determined by radiographic disease assessments per RECIST (v1.1).

8.2. Treatment Beyond Progression

Accumulating evidence indicates a minority of subjects treated with immunotherapy may derive clinical benefit despite initial evidence of PD.

Subjects Will be Permitted to Continue Treatment Beyond Initial RECIST v1.1 Defined PD as Long as they Meet the Following Criteria:

Investigator-assessed clinical benefit and subject is tolerating study drug.

No evidence of significant clinical decline.

9 Statistical Considerations

9.1. Study Design/Endpoints/Data Analysis

Phase I Part:

Design: Eligible patients are entered in cohorts of six at the first dose level. Doses are not escalated over the course of treatment of an individual patient. If 2 or more patients experience DLT in dose level 1, then dose de-escalation will occur. Dose level −1 will follow the same rules. If there are no more than 1 DLT, then the phase II portion of the trial will initiate. No Dose escalation is planned beyond dose level 1. The recommended Phase II dose will be defined as the highest dose level of GMCD40L vaccine in combination with nivolumab that induced DLT in fewer than 33% of patients. A total of 6 to 12 patients will be enrolled and evaluated, depending upon the number of patients enrolled in dose escalation phase. Data will be summarized overall using descriptive statistics.

Phase II Part:

This is a 2 arm randomized phase I/II trial design to test the hypothesis that the treatment in Arm B will produce clinically superior results to Arm A. The primary endpoint will be the tumor response rate. The secondary endpoints will be PFS duration of response and OS.

Patients will be randomized to one of the 2 arms described above (ratio is 1:1) at the time of registration. The Randomization Procedure is described in Section 4.1. All data will be documented in CRFs, entered into Excel spreadsheets designed for this purpose by the study co-chairs with the collaboration of the study biostatistician. Data checking programs, designed to look for data that are out of range or inconsistent will be run. Problems will be communicated to the co-chairs for resolution. All data, with names expunged, will be password protected and backed up daily by our computer support staff. They will reside on computers that are protected by anti-virus software and a firewall.

Data Analysis Plan: Statistical Plan for the Primary Objective.

We expect to find that the best overall tumor response rate during the immunotherapy will be observed in Arm B, the combination immunotherapy arm. The primary objective is to evaluate the efficacy of the two experimental regimens. If nivolumab plus vaccines produces a synergistic effect and produces an ORR of ≥46%, it will be brought forward for a subsequent phase III trial, which will be designed to compare the experimental regimen to a standard regimen with overall survival as the primary endpoint.

Study Design:

A "pick-the-winner" design for the randomized phase II clinical trial is proposed by employing Simon minimax two-stage design and Bayesian posterior probability. Specifically, a Simon minimax two-stage design will be used for each experimental arm[61]. If both arms fail at the first or second stage, the trial will stop. No winner will be claimed. If only one arm pass the second stage, the arm will be the winner. If both arms pass the second stage, we will use a Bayesian posterior probability, $r_{B>A}$, (probability of the response rate in arm B higher than in arm A) to select the winner. Table 9 lists the rule to claim a winner. The operating characteristics of this design are detailed in the sample size calculation.

TABLE 9

|  |  | Arm B | | |
| --- | --- | --- | --- | --- |
|  |  | fail in stage 1 | fail stage 2 | pass 2nd stage |
| Arm A | fail in stage 1 | both losers | both losers | Arm B winner |
|  | fail in stage 2 | both losers | both losers | Arm B winner |
|  | pass 2nd stage | Arm A winner | Arm A winner | Arm B winner if $r_{B>A} > 80\%$ |
|  |  |  |  | Arm A winner if $r_{B>A} < 20\%$ |

$r_{B>A}$: posterior probability of the response rate in arm B higher than in arm A This design has several features: (1) Randomization reduces selection bias and allows a greater degree of comparability, (2) The Simon two-stage design will allow for termination of an ineffective regimen earlier when compared to historical control data, and (3) The Bayesian posterior probability provides additional power to detect a definitive differential treatment effect. This trial design will allow us to more accurately determine if it is worthwhile to conduct a large phase III trial.

Descriptive statistics. For each arm, summaries of the primary endpoint (response rate) and important descriptors (e.g., age, gender) will be produced using descriptive statistics such as mean and standard deviation for measured continuous variables and marginal distributions for categorical variables. We will also use histograms and box-plots to understand aspects of data quality and overall characteristics of the data. All patients enrolled in the study will be included in the analysis (intent-to-treat analysis). No adjustments to the data are intended for dealing with missing values or patients who withdraw prior to completing the study. Objective tumor response rates will be calculated with a 2-sided 95% CI. Exploratory analysis with Chi-square tests to examine the relationship between clinical responses and treatment will be performed.

Analysis for ORR: The pick-the-winner strategy in Table 9 will be used to analyze ORR. Specifically, if both arms fail at the first or second stage, the trial will stop. No winner will be claimed. If only one arm pass the second stage, the arm will be the winner. If both arms pass the $2^{nd}$ stage, the posterior probability of the response rate in arm B higher than in arm A will be calculated to determine the winner. The corresponding posterior mean, median, and the credable confidence interval will be computed. A minimally informative beta distribution will be used as prior distribution with parameters a=1 and b=1.

Statistical Considerations for the Secondary Objectives #1.

Final data will depend on the following scenarios by the two parallel Simon two-stage design: (a) both arms complete the $2^{nd}$ stage (n=42 per arm), (b) arm B completes the $2^{nd}$ stage (n=42) but arm A stop at the $1^{st}$ stage (n=17), (c) both arms stop at the $1^{st}$ stage (n=17 per arm). Overall survival analysis and progression-free survival analysis (below) will be performed for each scenario.

Overall survival analysis (OS). The median OS of treated stage IV lung adenocarcinoma patients is 12.3 months. The median OS for patients treated with anti-PD-1 as first-line therapy followed by pemetrexed/carboplatin/bevacizumab is unknown, but hypothesized to be greater than that of patients treated with chemotherapy alone. We will be able to estimate whether or not this is true by comparing the median OS of patients in Arm A with the historical control value of 12.3 months. Furthermore, we hypothesize that the addition of vaccines to anti-PD-1 in Arm B will be more efficacious, so we hypothesize that the OS of patients in Arm B will be longer than that of patients in Arm A. The Kaplan-Meier method with log-rank test will be used to compare OS curves between the 2 arms.

Progression-free survival analysis (PFS). We hypothesize that the addition of vaccines to anti-PD-1 in Arm B will be more efficacious, so we hypothesize that the PFS of patients in Arm B will be longer than that of patients in patients treated with anti-PD-1 (Arm A). The Kaplan-Meier method with log-rank test will be used to compare PFS curves between the 2 arms.

Duration of response analysis. We hypothesize that the addition of vaccines to anti-PD-1 in Arm B will be more efficacious, so we hypothesize that the duration of response of patients in Arm B will be longer than that of patients in patients treated with anti-PD-1 (Arm A). The Kaplan-Meier method with log-rank test will be used to compare duration of response between the 2 arms.

9.2. Sample Size

Phase I Part:

A total of 6 to 12 patients will be enrolled and evaluated, depending upon the number of patients enrolled in the dose escalation phase.

Phase II Part:

N: Expect to enroll a total of 110 patients in order to have 96 enrolled patients to be randomized.

For all Phase I patients and all Phase II patients randomized to the combination arm who have received at least 1 dose of the nivolumab as well as 1 vaccine administration will be included in the efficacy and toxicity assessments. This includes subjects who do not complete Cycle #1. For those patients enrolled on Phase I or randomized to the combination arm and only receive either one dose of the vaccine or one dose of the nivolumab, they will be included in the toxicity assessments only, and the patient will need to be replaced for efficacy assessments. For those patients randomized to the Phase II single agent nivolumab arm, they must have received at least 1 dose of the nivolumab to be included in the efficacy as well as the toxicity assessments.

The Primary Objective (Tumor Response)

From historical data, we will consider 26% response rate as not warranting further study. We will use 46% response rate as a promising result to pursue further study. In other words, we are interested in at least 20% (46% vs. 26%) improvement in treatment efficacy for Arms B versus A. For each Arm, using a Simon minimax two-stage design with 3% type I error rate and 15% type II error rate, 37 patients will be enrolled in the first stage of the trial. If 10 or fewer patients respond, the treatment will be stopped. If 11 or more patients show a response, 11 additional patients (a total of 48 patients per group) will be enrolled. If the total number responding is 18 or less, we will conclude that the treatment is not effective. We plan to enroll a maximum of 100 patients in order to have 96% of the enrolled patients remain on the trial if both arms finish the 2nd stage. If both arms fail at the first or second stage, the trial will stop. No winner will be claimed. The sample size will be 74 if both arms fail at the first stage and 85 if only one arm fails at the first stage. If only one arm pass the second stage, the arm will be the winner. If both arms pass the second stage, we will use the posterior probability, $r_{B>A}$, (probability of the response rate in arm B higher than in arm A) to select the winner. A non-informative prior of beta distribution with parameters of a=1 and b=1 (equivalent of a uniform distribution ranged from 0 and 1) will be used to calculate the posterior probability. Arm B will be claimed as the winner if $r_{B>A}$>80% (about a 10% difference of response rate) and Arm A will be claimed as the winner if $r_{B>A}$<20%.

The operating characteristics of the two parallel Simon minimax two stage design is evaluated by simulation (100,000 times) using R software with "clinfun" package. In particular, we are interested in the probability of (correctly) selecting an arm as superior to the other arm if it is truly superior, and conversely, the probability of (incorrectly) selecting an arm that is no better than the other arm. Assuming that the true probabilities of response with arms A and B are 26% and 46%, respectively (scenario 1), the overall probability of (correctly) choosing arm B as superior, on the basis of superiority shown at the end of the trial, is 84% (power). The probability of (incorrectly) selecting arm A as superior is 0%. The probability of stopping arm A early and declaring arm B superior at the end of the trial is 83%, whereas the probability of arm A as the winner and early termination of arm B is 0%. There are 2% for both arms passing the second stage with 1% of Arm B claimed as the winner by the posterior probability ($r_{B>A}$) >80%. In scenario 2 (null scenario for type I error) of true response rate of 26% for both arms, there are 95% for both arms failed at the 1st or 2nd stage (i.e., 5% type I error). In scenario 3 of true response rate of 30% in arm A and 46% in arm B, power to claim arm B as the winner is 79%. The probability of stopping arm A early and declaring arm B superior at the end of the trial is 76%. There are 9% for both arms to pass the second stage with 2% of Arm B claimed as the winner by the posterior probability ($r_{B>A}$) >80%. In scenario 4 of true response rate of 36% in arm A and 46% in arm B (a 10% difference of response rate), power to claim arm B as the winner is 62%. The probability of stopping arm A early and declaring arm B superior at the end of the trial is 55%. The probability of both arms to pass the second stage increases to 30%. There are 7% of Arm B claimed as the winner by the posterior probability ($r_{B>A}$)>80%, while only 0% for arm A as the winner.

In summary, this design will have an 84% overall power to claim arm B as the winner when the true probabilities of response with arms A and B are 26% and 46%, respectively.

The power slightly deceases to 79% when the response rate is 30% in arm A with 46% in arm B. The power is 62% when there is only 10% difference of response rate (arm A: 36%; arm B: 46%). The type I error is reasonable at 5%.

Operating Characteristics:

| Scenario 1: Arm A = 26%; Arm B = 46% (Power* = 84%) | | | |
|---|---|---|---|
| | B.fail.stage1 | B.fail.stage2 | B.pass |
| A.fail.stage1 | 0.01 | 0.09 | 0.55 |
| A.fail.stage2 | 0.00 | 0.04 | 0.28 |
| A.pass | 0.00 | 0.00 | 0.02 (1% of arm B as winner) |

*Power is defined as the proportion of arm B passes the $2^{nd}$ stage and (a) arm A fails in the $1^{st}$ or $2^{nd}$ stage (55% + 28%) or (b) arm A pass the $2^{nd}$ stage, but the posterior probability, $r_{B>A}$, >80% (1%).

| Scenario 2 : Arm A = 26%; Arm B = 26% (Type I error = 5%) | | | |
|---|---|---|---|
| | B.fail.stage1 | B.fail.stage2 | B.pass |
| A.fail.stage1 | 0.41 | 0.21 | 0.02 |
| A.fail.stage2 | 0.21 | 0.11 | 0.01 |
| A.pass | 0.02 | 0.01 | 0.00 (0% of arm B as winner) |

| Scenario 3 : Arm A = 30%; Arm B = 46% Power = 79%) | | | |
|---|---|---|---|
| | B.fail.stage1 | B.fail.stage2 | B.pass |
| A.fail.stage1 | 0.01 | 0.06 | 0.36 |
| A.fail.stage2 | 0.01 | 0.07 | 0.40 |
| A.pass | 0.00 | 0.01 | 0.09 (2% of arm B as winner) |

| Scenario 4 : Arm A = 36%; Arm B = 46% Power = 62%) | | | |
|---|---|---|---|
| | B.fail.stage1 | B.fail.stage2 | B.pass |
| A.fail.stage1 | 0.00 | 0.02 | 0.14 |
| A.fail.stage2 | 0.01 | 0.06 | 0.41 |
| A.pass | 0.01 | 0.05 | 0.30 (7% of arm B as winner) |

The Secondary Objective (OS/PFS)

There are at least three scenarios by the two parallel Simon two-stage design: (a) both arms complete the $2^{nd}$ stage (n=42 per arm), (b) arm B completes the $2^{nd}$ stage (n=42) but arm A stop at the $1^{st}$ stage (n=17), (c) both arms stop at the $1^{st}$ stage (n=17 per arm).

Power analysis (Table 10) is performed based on the three scenarios using two-sided log-rank test at 20%/type I error and an accrual time of 18 months and follow-up time of 42 months. For OS, with the sample size of 42 per arm, it will give 82% power to detect a hazard ratio (HR) of 0.6 or a difference of median survival time (20 months in Arm B versus 12 months in Arm A). The power is 65% for a sample size of 17 in arm A and 42 in arm B. When each of both arms ends with 17 patients, the power decreases to 55%. For PFS, the sample size of 42 per arm, it will give 83% power to detect a hazard ratio (HR) of 0.6 or a difference of median survival time (13.3 months in Arm B versus 8 months in Arm A). The power is 66% for a sample size of 17 in arm A and 42 in arm B. When each of both arms ends with 17 patients, the power decreases to 57%.

TABLE 10

Power analysis for the secondary objective (OS/PFS)

| | Median survival time: Arm A | Median survival time: Arm B | HR | Sample size for Arm A | Sample size for Arm B | Power |
|---|---|---|---|---|---|---|
| OS | 12 | 16 | 0.75 | 42 | 42 | 0.50 |
| | 12 | 18 | 0.67 | 42 | 42 | 0.68 |
| | 12 | 20 | 0.60 | 42 | 42 | 0.82 |
| | 12 | 20 | 0.60 | 17 | 42 | 0.65 |
| | 12 | 20 | 0.60 | 17 | 17 | 0.55 |
| PFS | 8 | 13.3 | 0.60 | 42 | 42 | 0.83 |
| | 8 | 13.3 | 0.60 | 17 | 42 | 0.66 |
| | 8 | 13.3 | 0.60 | 17 | 17 | 0.57 |

Two-sided log-rank test with 20% type I error
Assume 18-month accrual time with 42 months of follow-up 10 Other and Administrative Considerations
10.1. Correlative Biomarkers
10.1.1 Collection of Pharmacodynamic Markers Archival tumor specimens will be collected on all patients. Where sufficient archival tissue does not exist, patients will undergo a fresh biopsy. These samples will be used to evaluate potentially predictive biomarkers and complete other correlative studies. Approximately 125 µL of tumor sample is required for this purpose. Fresh tumor specimens will be collected by image-guided biopsy for those without available archival tissue. The biopsies will be performed under image guidance (including but not limited to CT or ultrasound-guided core biopsies) as determined by the location of tumor and risks associated with each procedure. Fresh tumor biopsies, on-site evaluations for tissue quality will be performed by the cytotechnologist to ensure viable tissue and for collection of adequate tumor sample. Four to 6 core biopsy samples will be collected. At a minimum, 2 will be placed in neutral-buffered formalin and embedded in paraffin wax and two core needle samples will be snap frozen and stored in liquid nitrogen. The tumor collected through these methods will be analyzed to explore whether positive vs negative biomarkers could predict response and resistance to the treatment.

10.1.2 Molecular Methods:

PD-L1 expression will be measured using the IHC assay based on the anti-PD-L1 monoclonal antibody (most likely the DAKO clone 28-8 but others may be explores). Positive staining with this assay is currently defined as tumor cell membrane staining at any intensity, analyzed with a cut-off value of ≥5% in a minimum number of 100 evaluable cells. Baseline tumor PD-L1 expression was evaluated for potential association with ORR, PFS, and overall survival (OS).

Further, exploratory correlative studies may be completed based on the additional data obtained including utilization of an advanced DNA platform or additional immune based biomarker analyses. These results would also be correlated with patient outcomes and potentially help to address some of the critical barriers for effective personalized treatment.

10.1.3 Molecular Analyses:

These correlates will be analyzed using descriptive statistics to compare disease outcome in biomarker positive and negative subsets. In addition, univariate and multivariate analyses will be performed to see whether the markers described above (both as continuous or dichotomous variable) predict for disease outcome (i.e., disease control rate, response and PFS after appropriate adjustment for other prognostic variables).

10.2 Thoracic Program Overview

The Department of Thoracic Oncology at Moffitt Cancer Center sees nearly ~1300 new cases of lung cancer each year and has eight dedicated thoracic medical oncologists. We have conducted six phase I/II trials in similar patient populations as single-institution trials during the 5 past years[62-65]. Members of this research team have a successful track record of completion of trials with biomarker collection and analyses in advanced lung cancer[66,67] as well as successful collaborations and development of grant applications. We would like to emphasize that trial published in JCO and Cancer involved a dedicated collection of a histological tumor specimen for molecular analysis for all patients. Together, these trials included the use of novel agents that required close monitoring, biomarker assessment, data collection and management, and tumor biopsies, testifying to our ability to successfully execute and publish such trial.

10.3. Reporting and Exclusions
10.3.1 Evaluation of Toxicity

All patients will be evaluable for toxicity from the time of their first treatment.

10.3.2 Evaluation of Response

All patients included in the study must be assessed for response to treatment, even if there are major protocol treatment deviations or if they are ineligible. Each patient will be assigned one of the following categories: 1) complete response, 2) partial response, 3) stable disease, 4) progressive disease, 5) early death from malignant disease, 6) early death from toxicity, 7) early death because of other cause, or 9) unknown (not assessable, insufficient data). [Note: By arbitrary convention, category 9 usually designates the "unknown" status of any type of data in a clinical database.]

All of the patients who met the eligibility criteria (with the possible exception of those who received no study medication) should be included in the main analysis of the response rate. Patients in response categories 4-9 should be considered to have a treatment failure (disease progression). Thus, an incorrect treatment schedule or drug administration does not result in exclusion from the analysis of the response rate.

All conclusions will be based on all eligible patients. Subanalyses may then be performed on the basis of a subset of patients, excluding those for whom major protocol deviations have been identified (e.g., early death due to other reasons, early discontinuation of treatment, major protocol violations, etc.). However, these subanalyses may not serve as the basis for drawing conclusions concerning treatment efficacy, and the reasons for excluding patients from the analysis will be clearly reported. The 95% confidence intervals will also be provided.

11 Data Safety Monitoring Plan
11.1. Risk to Subjects
11.1.1. Human Subject Involvement and Characteristics Human subjects who have the diagnosis of advanced NSCLC are eligible to participate in the clinical trial described in this proposal. The risk to subjects will be outlined clearly and in detail in the informed consent. Women who are pregnant are not eligible.

11.2. Recruitment and Informed Consent

Patients who present to the Thoracic Oncology Program at the Moffitt Cancer Center who have advanced NSCLC are offered participation in the clinical trial described in this proposal. The trial is explained in detail to the patients by one of the investigators on the trial. The patients are given the opportunity to read the informed consent document and are given a chance to ask questions. If they wish to participate the patient will then sign the informed consent document in the presence of a witness. The study team member who participates in the informed consent process also documents, in a clinic note, the nature of the consent process that occurred.

11.3. Protection Against Risk

To protect participants from excess risk, the above-mentioned study procedures and dose-escalation scheme were instituted. Additional protection is provided through the data safety and monitoring plan described below. The complete care of each patient, including the clinical management of all toxicities, is provided to the patient by physicians at the Moffitt Cancer Center. The clinical data are kept in the patient's individual Moffitt Cancer Center electronic hospital record. Research study documentation charts are kept in a locked room within the Thoracic department office area in FOB1 w/limited access and through Oncore (a Web-based, password-protected database), with privacy protected to the full extent of the law. Authorized research investigators, the Department of Health and Human Services, and the USF Institutional Review Board may inspect the records. Final protocol and ICF approvals will be obtained from the IRB.

Additional protection is provided through the data safety and monitoring plan described below.

11.4. Importance of the Knowledge to be Gained

The development of a well-tolerated and effective regimen in a disease could potentially at worst add to the armamentarium of available regimens and at best change standard of care. Specific strategies to improve the care of patients relapsing following chemotherapy for lung cancer are direly needed.

11.5. Data Safety and Monitoring Plan

The Data Safety & Monitoring Plan (DSMP) will ensure that this trial is well designed, responsibly managed, appropriately reported, and that it protects the rights and welfare of patients. The following internal and external review and monitoring processes provide oversight and active monitoring of this trial:

The Principal Investigators (PI)
The Clinical Trials Office (CTO)
The Scientific Review Committee (SRC)
The Protocol Monitoring Committee (PMC);
The Research Compliance Division (RCD) of the Cancer Center's Compliance Office;
Institutional Review Board (IRB).

The protocol includes a section that specifies the following with respect to Adverse Event reporting: what constitutes an adverse event (versus what is a serious adverse event), the entities to which adverse events should be reported, the timing of this reporting, and the person or persons responsible for reporting. This includes prompt (within one day of knowledge of the event) reporting to the IRB for unanticipated risks to subjects and reporting in writing within five working days to the IRB and sponsor.

11.6. Scientific Review Committee (SRC)

The two Therapeutic boards of the SRC meet every other week one on the first Wednesday and the second one meets on the third Thursday of every month.

Each SRC conducts a formal internal peer review of all clinical protocols and general scientific oversight of interventional clinical research. Protocols are reviewed for scientific merit, adequate study design, safety, availability of targeted study population, and feasibility of timely completion of all proposed research projects to be conducted by its assigned programs at the Cancer Center. The SRC is responsible for evaluating the risk/benefit assessment and corresponding data and safety monitoring plan as part of the scientific review and approval process.

11.7. PI Responsibility

The PI of each study is ultimately responsible for every aspect of the design, conduct and actions of all members of the research team. This includes the final analysis of the protocol.

All protocols include a DSMP and procedures for its implementation commensurate with the risk and complexity of the study. The DSMP must include a structured adverse event determination, monitoring and reporting system, including standardized forms and procedures for referring and/or treating subjects experiencing adverse events. The plan must include data and safety-monitoring procedures for subjects enrolled who may be receiving a part of their protocol-required treatment at community sites.

In all cases, the PI of the study will have primary responsibility for ensuring that the protocol is conducted as approved by the SRC and IRB. The PI will ensure that the monitoring plan is followed, that all data required for oversight of monitoring are accurately reported to a DSMB and/or to the PMC and IRB as required, that all adverse events are reported according to protocol guidelines, and that any adverse actions reflecting patient safety concerns are appropriately reported.

11.8. The Protocol Monitoring Committee (PMC)

The PMC meets once a month. The PMC reviews and evaluates safety and/or efficacy data for all physician authored clinical intervention trials. The PMC ensures the safety of patients and the validity and integrity of data. PMC reviews SAEs, deviations, Interim analysis, interim and final reports from the external Data Monitoring Committee (DMC) as well as audits both internally and externally. The PMC can make the following determinations, Accepted, Acceptable with Corrective Action and Tabled.

Investigators of studies, which are designated to be reviewed by the PMC for data and safety monitoring, shall provide an interim analysis report of the study's progress and summary of adverse events and deviations based on the phase of the study and the associated risk of the study or more often if applicable. The external DSMB (if applicable) shall forward its report for high-risk studies designated for external review at least annually or more often if applicable.

11.9. Suspension/Termination

The PMC and/or the IRB may vote to suspend or terminate approval of a research study not being conducted in accordance with the IRB, the Cancer Center and/or regulatory requirements or that has been associated with unexpected problems or serious harm to subjects. The PMC/IRB will notify the PI in writing of such suspension or terminations. It is the responsibility of the PMC/IRB Chairperson to ensure prompt written notification of any suspensions or terminations of PMC/IRB approval to the relevant Federal Agencies, including OHRP, FDA, the study sponsor/funding source and if applicable, the Affiliate Program.

11.10. Trial Discontinuation

For reasonable cause the Investigator and/or sponsor may terminate this study prematurely. Conditions that may warrant termination include, but are not limited to: the discovery of an unexpected, significant, or unacceptable risk to the patients enrolled in the study or if the accrual goals are met. A written notification of termination will be issued.

11.11. Monitoring of the Study and Regulatory Compliance

The Principal Investigator and the Clinical Research Coordinator assigned to the case will be primarily responsible for maintaining all study related documents including the clinical research forms. Oncore is the database of record for all CRF entries and will be verified with source documentation. The review of medical records within PowerChart will be done in a manner to assure that patient confidentiality is maintained.

11.12. Internal Monitoring Plan

Data will be captured in Oncore, Moffitt's Clinical Trials Database.

Regulatory documents and case report forms will be reviewed routinely for accuracy, completeness and source verification of data entry, validation of appropriate informed consent process, adherence to study procedures, and reporting of SAEs and protocol deviations according to Moffitt's Monitoring Policies.

11.13. Protocol Modifications

No modifications will be made to the protocol without the agreement of the investigators. Changes that significantly affect the safety of the patients, the scope of the investigation, or the scientific quality of the study will require Scientific Review Committee and Institutional Review Board approval prior to implementation, except where the modification is necessary to eliminate apparent immediate hazard to human subjects. Any departures from the protocol must be fully documented in the case report form and the source documentation.

REFERENCES

1. Pardoll D M. The blockade of immune checkpoints in cancer immunotherapy. Nat Rev Cancer 2012; 12:252-64.
2. Aerts J G, Hegmans J P. Tumor-specific cytotoxic T cells are crucial for efficacy of immunomodulatory antibodies in patients with lung cancer. Cancer Res 2013; 73:2381-8.
3. Sandler A, Gray R, Perry M C, et al. Paclitaxel-carboplatin alone or with bevacizumab for non-small-cell lung cancer. The New England journal of medicine 2006; 355:2542-50.
4. Topalian S L, Hodi F S, Brahmer J R, et al. Safety, activity, and immune correlates of anti-PD-1 antibody in cancer. N Engl J Med 2012; 366:2443-54.
5. Rizvi N A, Shepherd F A, Antonia S J, et al. First-line monotherapy with nivolumab (anti-PD-1; BMS-936558, ONO-4538) in advanced non-small cell lung cancer (NSCLC): safety, efficacy, and correlation of outcomes with PD-L1 status. Chicago Multidisciplinary Symposium in Thoracic Oncology 2014 Annual Meeting; October 30-November 1; Chicago, Ill.
6. Tsuboi A, Oka Y, Osaki T, et al. WT1 peptide-based immunotherapy for patients with lung cancer: report of two cases. Microbiol Immunol 2004; 48:175-84.
7. Atanackovic D, Altorki N K, Stockert E, et al. Vaccine-induced CD4+ T cell responses to MAGE-3 protein in lung cancer patients. J Immunol 2004; 172:3289-96.
8. Harada M, Gohara R, Matsueda S, et al. In vivo evidence that peptide vaccination can induce HLA-DR-restricted CD4+ T cells reactive to a class I tumor peptide. J Immunol 2004; 172:2659-67.
9. Hirschowitz E A, Foody T, Kryscio R, Dickson L, Sturgill J, Yannelli J. Autologous dendritic cell vaccines for non-small-cell lung cancer. J Clin Oncol 2004; 22:2808-15.
10. Ueda Y, Itoh T, Nukaya I, et al. Dendritic cell-based immunotherapy of cancer with carcinoembryonic antigen-derived, HLA-A24-restricted CTL epitope: Clinical outcomes of 18 patients with metastatic gastrointestinal or lung adenocarcinomas. Int J Oncol 2004; 24:909-17.
11. Nemunaitis J, Sterman D, Jablons D, et al. Granulocyte-macrophage colony-stimulating factor gene-modified autologous tumor vaccines in non-small-cell lung cancer. J Natl Cancer Inst 2004; 96:326-31.
12. Salgia R, Lynch T, Skarin A, et al. Vaccination with irradiated autologous tumor cells engineered to secrete granulocyte-macrophage colony-stimulating factor augments antitumor immunity in some patients with metastatic non-small-cell lung carcinoma. J Clin Oncol 2003; 21:624-30.
13. Raez L E, Cassileth P A, Schlesselman J J, et al. Induction of CD8 T-cell-Ifn-gamma response and positive clinical outcome after immunization with gene-modified allogeneic tumor cells in advanced non-small-cell lung carcinoma. Cancer Gene Ther 2003; 10:850-8.
14. Raez L E, Cassileth P A, Schlesselman J J, et al. Allogeneic vaccination with a B7.1 HLA-A gene-modified adenocarcinoma cell line in patients with advanced non-small-cell lung cancer. J Clin Oncol 2004; 22:2800-7.
15. Rosenberg S A. Identification of cancer antigens: impact on development of cancer immunotherapies. Cancer J Sci Am 2000; 6 Suppl 3:S200-7.
16. Pittet M J, Valmori D, Dunbar P R, et al. High frequencies of naive Melan-A/MART-1-specific CD8(+) T cells in a large proportion of human histocompatibility leukocyte antigen (HLA)-A2 individuals. J Exp Med 1999; 190:705-15.
17. Anichini A, Molla A, Mortarini R, et al. An expanded peripheral T cell population to a cytotoxic T lymphocyte (CTL)-defined, melanocyte-specific antigen in metastatic melanoma patients impacts on generation of peptide-specific CTLs but does not overcome tumor escape from immune surveillance in metastatic lesions. J Exp Med 1999; 190:651-67.
18. Jager E, Nagata Y, Gnjatic S, et al. Monitoring CD8 T cell responses to NY-ESO-1: correlation of humoral and cellular immune responses. Proc Natl Acad Sci USA 2000; 97:4760-5.
19. Banchereau J, Steinman R M. Dendritic cells and the control of immunity. Nature 1998; 392:245-52.
20. Gabrilovich D I, Chen H L, Girgis K R, et al. Production of vascular endothelial growth factor by human tumors inhibits the functional maturation of dendritic cells. Nat Med 1996; 2:1096-103.
21. Menetrier-Caux C, Montmain G, Dieu M C, et al. Inhibition of the differentiation of dendritic cells from CD34(+) progenitors by tumor cells: role of interleukin-6 and macrophage colony-stimulating factor. Blood 1998; 92:4778-91.
22. Chen Q, Daniel V, Maher D W, Hersey P. Production of IL-10 by melanoma cells: examination of its role in immunosuppression mediated by melanoma. Int J Cancer 1994; 56:755-60.
23. Smith D R, Kunkel S L, Burdick M D, et al. Production of interleukin-10 by human bronchogenic carcinoma. Am J Pathol 1994; 145:18-25.
24. Huang M, Wang J, Lee P, et al. Human non-small cell lung cancer cells express a type 2 cytokine pattern. Cancer Res 1995; 55:3847-53.
25. Steinbrink K, Wolfr M, Jonuleit H, Knop J, Enk A H. Induction of tolerance by IL-10-treated dendritic cells. J Immunol 1997; 159:4772-80.
26. Koch F, Stanzl U, Jennewein P, et al. High level IL-12 production by murine dendritic cells: upregulation via MHC class II and CD40 molecules and downregulation by IL-4 and IL-10. J Exp Med 1996; 184:741-6.
27. Steinbrink K, Jonuleit H, Muller G, Schuler G, Knop J, Enk A H. Interleukin-10-treated human dendritic cells induce a melanoma-antigen-specific anergy in CD8(+) T cells resulting in a failure to lyse tumor cells. Blood 1999; 93:1634-42.

28. Pirtskhalaishvili G, Shurin G V, Esche C, et al. Cytokine-mediated protection of human dendritic cells from prostate cancer-induced apoptosis is regulated by the Bcl-2 family of proteins. Br J Cancer 2000; 83:506-13.
29. Esche C, Shurin G V, Kirkwood J M, et al. Tumor necrosis factor-alpha-promoted expression of Bcl-2 and inhibition of mitochondrial cytochrome c release mediate resistance of mature dendritic cells to melanoma-induced apoptosis. Clin Cancer Res 2001; 7:974s-9s.
30. Kiertscher S M, Luo J, Dubinett S M, Roth M D. Tumors promote altered maturation and early apoptosis of monocyte-derived dendritic cells. J Immunol 2000; 164:1269-76.
31. Simons J W, Jaffee E M, Weber C E, et al. Bioactivity of autologous irradiated renal cell carcinoma vaccines generated by ex vivo granulocyte-macrophage colony-stimulating factor gene transfer. Cancer Res 1997; 57:1537-46.
32. Chang A E, Li Q, Bishop D K, Normolle D P, Redman B D, Nickoloff B J.
Immunogenetic therapy of human melanoma utilizing autologous tumor cells transduced to secrete granulocyte-macrophage colony-stimulating factor. Hum Gene Ther 2000; 11:839-50.
33. Simons J W, Mikhak B, Chang J F, et al. Induction of immunity to prostate cancer antigens: results of a clinical trial of vaccination with irradiated autologous prostate tumor cells engineered to secrete granulocyte-macrophage colony-stimulating factor using ex vivo gene transfer. Cancer Res 1999; 59:5160-8.
34. Soiffer R, Lynch T, Mihm M, et al. Vaccination with irradiated autologous melanoma cells engineered to secrete human granulocyte-macrophage colony-stimulating factor generates potent antitumor immunity in patients with metastatic melanoma. Proc Natl Acad Sci USA 1998; 95:13141-6.
35. Kusumoto M, Umeda S, Ikubo A, et al. Phase 1 clinical trial of irradiated autologous melanoma cells adenovirally transduced with human GM-CSF gene. Cancer Immunol Immunother 2001; 50:373-81.
36. Jaffee E M, Hruban R H, Biedrzycki B, et al. Novel allogeneic granulocyte-macrophage colony-stimulating factor-secreting tumor vaccine for pancreatic cancer a phase i trial of safety and immune activation. J Clin Oncol 2001; 19:145-56.
37. Borrello I, Sotomayor E M, Cooke S, Levitsky H I. A universal granulocyte-macrophage colony-stimulating factor-producing bystander cell line for use in the formulation of autologous tumor cell-based vaccines. Hum Gene Ther 1999; 10:1983-91.
38. Mach N, Dranoff G. Cytokine-secreting tumor cell vaccines [In Process Citation]. Curr Opin Immunol 2000; 12:571-5.
39. Nelson W G, Simons J W, Mikhak B, et al. Cancer cells engineered to secrete granulocyte-macrophage colony-stimulating factor using ex vivo gene transfer as vaccines for the treatment of genitourinary malignancies. Cancer Chemother Pharmacol 2000; 46:S67-72.
40. Chiodoni C, Paglia P, Stoppacciaro A, Rodolfo M, Parenza M, Colombo M P. Dendritic cells infiltrating tumors cotransduced with granulocytelmacrophage colony-stimulating factor (GM-CSF) and CD40 ligand genes take up and present endogenous tumor-associated antigens, and prime naive mice for a cytotoxic T lymphocyte response. J Exp Med 1999; 190:125-33.
41. Cella M, Scheidegger D, Palmer-Lehmann K, Lane P, Lanzavecchia A, Alber G. Ligation of CD40 on dendritic cells triggers production of high levels of interleukin-12 and enhances T cell stimulatory capacity: T-T help via APC activation. J Exp Med 1996; 184:747-52.
42. Peguet-Navarro J, Dalbiez-Gauthier C, Rattis F M, Van Kooten C, Banchereau J, Schmitt
D. Functional expression of CD40 antigen on human epidermal Langerhans cells. J Immunol 1995; 155:4241-7.
43. Caux C, Massacrier C, Vanbervliet B, et al. Activation of human dendritic cells through CD40 cross-linking. J Exp Med 1994; 180:1263-72.
44. Dotti G, Savoldo B, Yotnda P, Rill D, Brenner M K. Transgenic expression of CD40 ligand produces an in vivo antitumor immune response against both CD40(+) and CD40(−) plasmacytoma cells. Blood 2002; 100:200-7.
45. Borrello I, et al., A universal granulocyte-macrophage colony-stimulating factor-producing bystander cell line for use in the formulation of autologous tumor cell-based vaccines.
Hum Gene Ther, 1999; 10:1983-91.
46. Wroblewski J M, Bixby D L, Borowski C, Yannelli J R. Characterization of human non-small cell lung cancer (NSCLC) cell lines for expression of MHC, co-stimulatory molecules and tumor-associated antigens. Lung Cancer 2001; 33:181-94.
47. Jang S J, Sora J C, Wang L, et al. Activation of melanoma antigen tumor antigens occurs early in lung carcinogenesis. Cancer Res 2001; 61:7959-63.
48. Brahmer J R, Drake C G, Wollner, et al. Phase I study of single-agent anti-programmed death-1 (MDX-1106) in refractory solid tumors: safety, clinical activity, pharmacodynamics, and immunologic correlates. J Clin Oncol 2010; 28:3167-75.
49. Bristol-Myers Squibb. BMS-936558 (nivolumab) Investigator Brochure, Version
13. Princeton, N.J.: Bristol-Myers Squibb.; 28 Jul. 2014.
50. Delamarre L, Holcombe H, Mellman. Presentation of exogenous antigens on major histocompatibility complex (MHC) class I and MHC class II molecules is differentially regulated during dendritic cell maturation. J Exp Med 2003; 198:111-22.
51. Dessureault S, Noyes D, Lee D, et al. A phase-I trial using a universal GM-CSF-producing and CD40L-expressing bystander cell line (GM.CD40L) in the formulation of autologous tumor cell-based vaccines for cancer patients with stage IV disease. Ann Surg Oncol 2007; 14:869-84.
52. Hanna N, Shepherd F A, Fossella F V, et al. Randomized phase III trial of pemetrexed versus docetaxel in patients with non-small-cell lung cancer previously treated with chemotherapy. J Clin Oncol 2004; 22:1589-97.
53. Creelan B C, Antonia S, Noyes D, et al. Phase II trial of a GM-CSF-producing and CD40L-expressing bystander cell line combined with an allogeneic tumor cell-based vaccine for refractory lung adenocarcinoma. J Immunother 2013; 36:442-50.
54. Lozzio B B, Lozzio C B. Properties and usefulness of the original K-562 human myelogenous leukemia cell line. Leuk Res 1979; 3:363-70.
55. Lozzio C B, Lozzio B B. Human chronic myelogenous leukemia cell-line with positive Philadelphia chromosome. Blood 1975; 45:321-34.
56. Andersson L C, Nilsson K, Gahmberg C G. K562-a human erythroleukemic cell line. Int J Cancer 1979; 23:143-7.
57. Ortaldo J R, Oldham R K, Cannon G C, Herberman R B. Specificity of natural cytotoxic reactivity of normal human lymphocytes against a myeloid leukemia cell line. J Natl Cancer Inst 1977; 59:77-82.
58. Dimery I W, Ross D D, Testa J R, et al. Variation amongst K562 cell cultures. Exp Hematol 1983; 11:601-10.
59. Eisenhauer E A, Therasse P, Bogaerts J, et al. New response evaluation criteria in solid tumours: revised RECIST guideline (version 1.1). Eur J Cancer 2009; 45:228-47.
60. Schwartz L H, Bogaerts J, Ford R, et al. Evaluation of lymph nodes with RECIST 1.1. Eur J Cancer 2009; 45:261-7.
61. Simon R. Optimal two-stage designs for phase II clinical trials. Control Clin Trials 1989; 10:1-10.
62. Chiappori A, Simon G, Williams C, et al. Phase II study of first-line sequential chemotherapy with gemcitabine-carboplatin followed by docetaxel in patients with advanced non-small cell lung cancer. Oncology 2005; 68:382-90.
63. Simon G, Sharma A, Li X, et al. Feasibility and efficacy of molecular analysis-directed individualized therapy in advanced non-small-cell lung cancer. J Clin Oncol 2007; 25:2741-6.
64. Simon G R, Extermann M, Chiappori A, et al. Phase 2 trial of docetaxel and gefitinib in the first-line treatment of patients with advanced nonsmall-cell lung cancer (NSCLC) who are 70 years of age or older. Cancer 2008; 112:2021-9.
65. Chiappori A A, Haura E, Rodriguez F A, et al. Phase I/II study of atrasentan, an endothelin A receptor antagonist, in combination with paclitaxel and carboplatin as first-line therapy in advanced non-small cell lung cancer. Clin Cancer Res 2008; 14:1464-9.
66. Haura E B, Tanvetyanon T, Chiappori A, et al. Phase I/II study of the Src inhibitor dasatinib in combination with erlotinib in advanced non-small-cell lung cancer. J Clin Oncol 2010; 28:1387-94.
67. Gray J, Haura E B, Chiappori A, et al. A phase I, pharmacokinetic and pharmacodynamic study of panobinostat, an HDAC inhibitor, combined with erlotinib in patients with advanced aerodigestive tract tumors. Clinical Cancer Research 2014; Published OnlineFirst Jan. 15, 2014; doi: 10.1158/1078-0432.CCR-13-2235

APPENDIX 1. SAMPLE OF DRUG ORDERING AND PHARMACY REFERENCE MATERIAL

Nivolumab (BMS-936558) Pharmacy Reference Material
   Nivolumab has a concentration of 10 mg/mL and is provided in a 10 mL vial. Ten or five vials are provided in a carton.
Preparation and Administration:
1. Visually inspect the drug product solution for particulate matter and discoloration prior to administration. Discard if solution is cloudy, if there is pronounced discoloration (solution may have a pale-yellow color), or if there is foreign particulate matter other than a few translucent-to-white, amorphous particles.
Note: Mix by gently inverting several times. Do not shake.
2. Aseptically withdraw the required volume of nivolumab solution into a syringe, and dispense into an IV. bag. If multiple vials are needed for a subject, it is important to use a separate sterile syringe and needle for each vial to prevent problems such as dulling of needle tip, stopper coring, repeated friction of plunger against syringe barrel wall. Do not enter into each vial more than once. Do not administer study drug as an IV push or bolus injection
3. Add the appropriate volume of 0.9% Sodium Chloride Injection solution or 5% Dextrose Injection solution. It is acceptable to add nivolumab solution from the vials into an appropriate pre-filled bag of diluent.
Note: Nivolumab infusion concentration must be at or above the minimum allowable concentration of 1 mg/mL.
   Note: It is not recommended that so-called "channel" or tube systems are used to transport prepared infusions of nivolumab.
4. Attach the IV bag containing the nivolumab solution to the infusion set and filter.
5. At the end of the infusion period, flush the line with a sufficient quantity of approved diluents.
Example Dose Calculation [at 3 mg/kg]
Total dose should be calculated as follows (assuming total dose volume of 210 mL, 70 kg pt, dose of 3 mg/kg):
   Subject body weight in kg×3 mg (for the 3 mg/kg cohort)= total dose (mg) 70 kg×3 mg/kg=210 mg
   Total dose (mg)÷10 mg/mL=Amount of solution to be withdrawn from vials 210 mg÷10 mg/mL=21 mL
Example of Total Volume of Solution to Infuse (mL) for a Minimum Conc Solution.–Volume of 10 mg/mL Solution (mL)=Volume of Diluent (mL) to Add
210 mL-21 mL=189 mL
   Please note it is perfectly acceptable to dose Nivolumab at a higher drug concentrations, as long as the total volume of diluted solution is at or above the minimum allowable concentration of 1 mg/mL, below is the calculation based on the above example. Please double check.
   Total dose in mg÷Total volume to infuse in mL=Overall drug concentration, mg/mL 210 mg÷210 mL=1 mg/mL
   FIGS. 6-12 show management algorithms.
   What is claimed is:
   1. A method for treating a cancer in a subject in need thereof, comprising administering to the subject a composition comprising a therapeutically effective amount of an immune checkpoint inhibitor and a therapeutically effective amount of a MHC negative cell line engineered to express GM-CSF and CD40 ligand; and wherein the checkpoint inhibitor comprises an anti-PD-1 antibody wherein the anti-PD-1 antibody comprises nivolumab; wherein the MHC negative cell line comprises K562 cells; and wherein the cancer comprises melanoma, renal cancer, Hodgkin lymphoma, head and neck cancer, colon cancer, liver cancer, or lung cancer.
   2. The method of claim 1, wherein the cancer comprises a non-small cell lung cancer.
   3. The method of claim 1, wherein the method further comprises administering to the subject radiated autologous tumor cells.
   4. The method of claim 1, wherein the K562 cell line is further engineered to express one more factors selected from the group consisting of IL-1, IL-2, IL-3, IL-4, IL-5, IL-6, IL-7, IL-8, IL-9, IL-10, IL-11, IL-15, erythropoietin, GCSF, M-CSF, platelet derived growth factor (PDGF), MSF, FLT-3 ligand, EGF, fibroblast growth factor (FGF), bFGF, (FGF-2), FGF-3, FGF-4, FGF-5, FGF-6, FGF-7, insulin-like growth factor 1 (IGF-1), insulin-like growth factor 2 (IGF-2); vascular endothelial growth factor (VEGF), IFN-gamma, IFN-alpha, IFN-beta, leukemia inhibitory factor (LIF), ciliary neurotrophic factor (CNTF), onocostatin M, stem cell factor (SCF), TGF-α, and TGF-βI.

* * * * *